United States Patent
Tearney et al.

(10) Patent No.: US 10,426,548 B2
(45) Date of Patent: *Oct. 1, 2019

(54) METHODS AND SYSTEMS FOR PROVIDING ELECTROMAGNETIC RADIATION TO AT LEAST ONE PORTION OF A SAMPLE USING CONFORMAL LASER THERAPY PROCEDURES

(75) Inventors: Guillermo J. Tearney, Cambridge, MA (US); Milen Shishkov, Watertown, MA (US); Brett Eugene Bouma, Quincy, MA (US); Benjamin J. Vakoc, Cambridge, MA (US)

(73) Assignee: The General Hosppital Corporation, Boston, MA (US)

( * ) Notice: Subject to any disclaimer, the term of this patent is extended or adjusted under 35 U.S.C. 154(b) by 3262 days.

This patent is subject to a terminal disclaimer.

(21) Appl. No.: 11/670,043

(22) Filed: Feb. 1, 2007

(65) Prior Publication Data

US 2007/0282403 A1 Dec. 6, 2007

Related U.S. Application Data

(60) Provisional application No. 60/764,622, filed on Feb. 1, 2006, provisional application No. 60/810,869, filed on Jun. 1, 2006.

(51) Int. Cl.
*A61B 5/00* (2006.01)
*A61B 18/22* (2006.01)
(Continued)

(52) U.S. Cl.
CPC ............ *A61B 18/24* (2013.01); *A61B 5/0066* (2013.01); *A61B 2017/00066* (2013.01); *A61B 2017/22051* (2013.01); *A61B 2018/2272* (2013.01)

(58) Field of Classification Search
CPC .......... A61B 18/24; A61B 2017/00066; A61B 2017/22051; A61B 2018/2272; A61B 5/0066
See application file for complete search history.

(56) References Cited

U.S. PATENT DOCUMENTS 2,339,754 A 1/1944 Brace
3,090,753 A 5/1963 Matuszak et al.
(Continued)

FOREIGN PATENT DOCUMENTS

CN 1550203 12/2004
DE 4105221 9/1991
(Continued)

OTHER PUBLICATIONS

Boppart et al., "Interventional optical coherence tomography for surgical guidance",Lasers and Electro-Optics, 1998. CLEO 98. Technical Digest. pp. 123-124 Summaries of papers presented at the Conference on May 3-8, 1998, Conference Location : San Francisco, CA, USA.*
(Continued)

*Primary Examiner* — Boniface N Nganga
(74) *Attorney, Agent, or Firm* — Quarles & Brady LLP

(57) ABSTRACT

According one exemplary embodiment of the present invention, method and system can be provided for applying a laser radiation to at least one portion of a biological structure. For example, a beam of the laser radiation can be provided to the portion, whereas a cross-sectional area of the beam is at most about ⅒th of an entire area of the at least one portion. The beam can be applied to the portion (a) based on a predetermined pattern, (b) while modulating a wavelength of the laser radiation, and/or (c) while monitoring a depth of the application of the laser radiation.

21 Claims, 18 Drawing Sheets

US 10,426,548 B2
Page 2

(51) Int. Cl.
*A61B 18/24* (2006.01)
*A61B 17/00* (2006.01)
*A61B 17/22* (2006.01)

(56) References Cited

U.S. PATENT DOCUMENTS

| | | | |
|---|---|---|---|
| 3,601,480 A | 8/1971 | Sexton |
| 3,856,000 A | 12/1974 | Chikama |
| 3,872,407 A | 3/1975 | Hughes |
| 3,941,121 A | 3/1976 | Olinger |
| 3,973,219 A | 8/1976 | Tang et al. |
| 3,983,507 A | 9/1976 | Tang et al. |
| 4,030,827 A | 6/1977 | Delhaye et al. |
| 4,030,831 A | 6/1977 | Gowrinathan |
| 4,140,364 A | 2/1979 | Yamashita et al. |
| 4,141,362 A | 2/1979 | Wurster |
| 4,224,929 A | 9/1980 | Furihata |
| 4,295,738 A | 10/1981 | Meltz et al. |
| 4,300,816 A | 11/1981 | Snitzer et al. |
| 4,303,300 A | 12/1981 | Pressiat et al. |
| 4,428,643 A | 1/1984 | Kay |
| 4,479,499 A | 10/1984 | Alfano et al. |
| 4,533,247 A | 8/1985 | Epworth |
| 4,585,349 A | 4/1986 | Gross et al. |
| 4,601,036 A | 7/1986 | Faxvog et al. |
| 4,607,622 A | 8/1986 | Fritch et al. |
| 4,631,498 A | 12/1986 | Cutler |
| 4,639,999 A | 2/1987 | Daniele |
| 4,650,327 A | 3/1987 | Ogi |
| 4,734,578 A | 3/1988 | Horikawa |
| 4,744,656 A | 5/1988 | Moran et al. |
| 4,751,706 A | 6/1988 | Rohde et al. |
| 4,763,977 A | 8/1988 | Kawasaki et al. |
| 4,770,492 A | 9/1988 | Levin et al. |
| 4,827,907 A | 5/1989 | Tashiro et al. |
| 4,834,111 A | 5/1989 | Khanna et al. |
| 4,868,834 A | 9/1989 | Fox et al. |
| 4,890,901 A | 1/1990 | Cross, Jr. |
| 4,892,406 A | 1/1990 | Waters |
| 4,905,169 A | 2/1990 | Buican et al. |
| 4,909,631 A | 3/1990 | Tan et al. |
| 4,925,302 A | 5/1990 | Cutler |
| 4,928,005 A | 5/1990 | Lefevre et al. |
| 4,940,328 A | 7/1990 | Hartman |
| 4,965,441 A | 10/1990 | Picard |
| 4,965,599 A | 10/1990 | Roddy et al. |
| 4,966,589 A | 10/1990 | Kaufman |
| 4,984,888 A | 1/1991 | Tobias et al. |
| 4,993,834 A | 2/1991 | Carlhoff et al. |
| 4,998,972 A | 3/1991 | Chin et al. |
| 5,039,193 A | 8/1991 | Snow et al. |
| 5,040,889 A | 8/1991 | Keane |
| 5,045,936 A | 9/1991 | Lobb et al. |
| 5,046,501 A | 9/1991 | Crilly |
| 5,065,331 A | 11/1991 | Vachon et al. |
| 5,085,496 A | 2/1992 | Yoshida et al. |
| 5,120,953 A | 6/1992 | Harris |
| 5,121,983 A | 6/1992 | Lee |
| 5,127,730 A | 7/1992 | Brelje et al. |
| 5,177,488 A | 1/1993 | Wang et al. |
| 5,197,470 A | 3/1993 | Helfer et al. |
| 5,202,745 A | 4/1993 | Sorin et al. |
| 5,202,931 A | 4/1993 | Bacus et al. |
| 5,208,651 A | 5/1993 | Buican |
| 5,212,667 A | 5/1993 | Tomlinson et al. |
| 5,214,538 A | 5/1993 | Lobb |
| 5,217,456 A | 6/1993 | Narciso, Jr. |
| 5,228,001 A | 7/1993 | Birge et al. |
| 5,241,364 A | 8/1993 | Kimura et al. |
| 5,248,876 A | 9/1993 | Kerstens et al. |
| 5,250,186 A | 10/1993 | Dollinger et al. |
| 5,251,009 A | 10/1993 | Bruno |
| 5,262,644 A | 11/1993 | Maguire |
| 5,275,594 A | 1/1994 | Baker |
| 5,281,811 A | 1/1994 | Lewis |
| 5,283,795 A | 2/1994 | Fink |
| 5,290,277 A * | 3/1994 | Vercimak et al. ............. 606/15 |
| 5,291,885 A | 3/1994 | Taniji et al. |
| 5,293,872 A | 3/1994 | Alfano et al. |
| 5,293,873 A | 3/1994 | Fang |
| 5,302,025 A | 4/1994 | Kleinerman |
| 5,304,173 A | 4/1994 | Kittrell et al. |
| 5,304,810 A | 4/1994 | Amos |
| 5,305,759 A | 4/1994 | Kaneko et al. |
| 5,317,389 A | 5/1994 | Hochberg et al. |
| 5,318,024 A | 6/1994 | Kittrell et al. |
| 5,321,501 A | 6/1994 | Swanson et al. |
| 5,333,144 A | 7/1994 | Liedenbaum et al. |
| 5,348,003 A | 9/1994 | Caro |
| 5,353,790 A | 10/1994 | Jacques et al. |
| 5,383,467 A | 1/1995 | Auer et al. |
| 5,394,235 A | 2/1995 | Takeuchi et al. |
| 5,400,771 A | 3/1995 | Pirak et al. |
| 5,404,415 A | 4/1995 | Mori et al. |
| 5,411,016 A | 5/1995 | Kume et al. |
| 5,414,509 A | 5/1995 | Veligdan |
| 5,419,323 A | 5/1995 | Kittrell et al. |
| 5,424,827 A | 6/1995 | Horwitz et al. |
| 5,439,000 A | 8/1995 | Gunderson et al. |
| 5,441,053 A | 8/1995 | Lodder et al. |
| 5,450,203 A | 9/1995 | Penkethman |
| 5,454,807 A | 10/1995 | Lennox et al. |
| 5,459,325 A | 10/1995 | Hueton et al. |
| 5,459,570 A | 10/1995 | Swanson et al. |
| 5,465,147 A | 11/1995 | Swanson |
| 5,479,928 A | 1/1996 | Cathignol et al. |
| 5,486,701 A | 1/1996 | Norton et al. |
| 5,491,524 A | 2/1996 | Hellmuth et al. |
| 5,491,552 A | 2/1996 | Kittrell |
| 5,522,004 A | 5/1996 | Djupsjobacka et al. |
| 5,526,338 A | 6/1996 | Hasman et al. |
| 5,555,087 A | 9/1996 | Miyagawa et al. |
| 5,562,100 A | 10/1996 | Kittrell et al. |
| 5,565,983 A | 10/1996 | Barnard et al. |
| 5,565,986 A | 10/1996 | Knüttel |
| 5,566,267 A | 10/1996 | Neuberger |
| 5,583,342 A | 12/1996 | Ichie |
| 5,590,660 A | 1/1997 | MacAulay et al. |
| 5,600,486 A | 2/1997 | Gal et al. |
| 5,601,087 A | 2/1997 | Richards-Kortum et al. |
| 5,621,830 A | 4/1997 | Lucey et al. |
| 5,623,336 A | 4/1997 | Raab et al. |
| 5,628,313 A | 5/1997 | Webster, Jr. |
| 5,635,830 A | 6/1997 | Itoh |
| 5,649,924 A | 7/1997 | Everett et al. |
| 5,697,373 A | 12/1997 | Gunderson et al. |
| 5,698,397 A | 12/1997 | Zarling et al. |
| 5,701,155 A | 12/1997 | Welch et al. |
| 5,710,630 A | 1/1998 | Essenpreis et al. |
| 5,716,324 A | 2/1998 | Toida |
| 5,719,399 A | 2/1998 | Alfano et al. |
| 5,730,731 A | 3/1998 | Mollenauer et al. |
| 5,735,276 A | 4/1998 | Lemelson |
| 5,740,808 A | 4/1998 | Panescu et al. |
| 5,748,318 A * | 5/1998 | Maris et al. ................ 356/630 |
| 5,748,598 A | 5/1998 | Swanson et al. |
| 5,752,518 A | 5/1998 | McGee et al. |
| 5,784,352 A | 7/1998 | Swanson et al. |
| 5,785,651 A | 7/1998 | Kuhn et al. |
| 5,795,295 A | 8/1998 | Hellmuth et al. |
| 5,801,826 A | 9/1998 | Williams |
| 5,801,831 A | 9/1998 | Sargoytchev et al. |
| 5,803,082 A | 9/1998 | Stapleton et al. |
| 5,807,261 A | 9/1998 | Benaron et al. |
| 5,810,719 A | 9/1998 | Toida |
| 5,817,144 A | 10/1998 | Gregory |
| 5,829,439 A | 11/1998 | Yokosawa et al. |
| 5,836,877 A | 11/1998 | Zavislan et al. |
| 5,840,023 A | 11/1998 | Oraevsky et al. |
| 5,840,031 A | 11/1998 | Crowley |
| 5,840,075 A | 11/1998 | Mueller et al. |
| 5,842,995 A | 12/1998 | Mahadevan-Jansen et al. |
| 5,843,000 A | 12/1998 | Nishioka et al. |
| 5,843,052 A | 12/1998 | Benja-Athon |

(56) References Cited

U.S. PATENT DOCUMENTS

| | | | |
|---|---|---|---|
| 5,847,827 A | 12/1998 | Fercher | |
| 5,862,273 A | 1/1999 | Pelletier | |
| 5,865,754 A | 2/1999 | Sevick-Muraca et al. | |
| 5,867,268 A | 2/1999 | Gelikonov et al. | |
| 5,868,731 A | 2/1999 | Budnik et al. | |
| 5,871,449 A | 2/1999 | Brown | |
| 5,872,879 A | 2/1999 | Hamm | |
| 5,877,856 A | 3/1999 | Fercher | |
| 5,887,009 A | 3/1999 | Mandella et al. | |
| 5,892,583 A | 4/1999 | Li | |
| 5,910,839 A | 6/1999 | Erskine et al. | |
| 5,912,764 A | 6/1999 | Togino | |
| 5,920,373 A | 7/1999 | Bille | |
| 5,920,390 A | 7/1999 | Farahi et al. | |
| 5,921,926 A | 7/1999 | Rolland et al. | |
| 5,926,592 A | 7/1999 | De Boer et al. | |
| 5,949,929 A | 9/1999 | Hamm | |
| 5,951,482 A | 9/1999 | Winston et al. | |
| 5,955,737 A | 9/1999 | Hallidy et al. | |
| 5,956,355 A | 9/1999 | Swanson et al. | |
| 5,964,749 A * | 10/1999 | Eckhouse et al. | 606/9 |
| 5,968,064 A | 10/1999 | Selmon et al. | |
| 5,975,697 A | 11/1999 | Hellmuth et al. | |
| 5,983,125 A | 11/1999 | Alfano et al. | |
| 5,984,916 A * | 11/1999 | Lai | 606/11 |
| 5,987,346 A | 11/1999 | Benaron et al. | |
| 5,991,697 A | 11/1999 | Nelson et al. | |
| 5,994,690 A | 11/1999 | Kulkarni et al. | |
| 5,995,223 A | 11/1999 | Power | |
| 6,002,480 A | 12/1999 | Izatt et al. | |
| 6,004,314 A | 12/1999 | Wei et al. | |
| 6,006,128 A | 12/1999 | Izatt et al. | |
| 6,007,996 A | 12/1999 | McNamara et al. | |
| 6,010,449 A | 1/2000 | Selmon et al. | |
| 6,014,214 A | 1/2000 | Li | |
| 6,016,197 A | 1/2000 | Krivoshlykov | |
| 6,020,963 A | 2/2000 | Dimarzio et al. | |
| 6,025,956 A | 2/2000 | Nagano et al. | |
| 6,033,721 A | 3/2000 | Nassuphis | |
| 6,037,579 A | 3/2000 | Chan et al. | |
| 6,044,288 A | 3/2000 | Wake et al. | |
| 6,045,511 A | 4/2000 | Lutz et al. | |
| 6,048,742 A | 4/2000 | Weyburne et al. | |
| 6,052,186 A | 4/2000 | Tsai | |
| 6,053,613 A | 4/2000 | Wei et al. | |
| 6,069,698 A | 5/2000 | Ozawa et al. | |
| 6,078,047 A | 6/2000 | Mittleman et al. | |
| 6,091,496 A | 7/2000 | Hill | |
| 6,091,984 A | 7/2000 | Perelman et al. | |
| 6,094,274 A | 7/2000 | Yokoi | |
| 6,107,048 A | 8/2000 | Goldenring et al. | |
| 6,111,645 A | 8/2000 | Tearney | |
| 6,117,128 A | 9/2000 | Gregory | |
| 6,120,516 A | 9/2000 | Selmon et al. | |
| 6,134,003 A | 10/2000 | Tearney et al. | |
| 6,134,010 A | 10/2000 | Zavislan | |
| 6,134,033 A | 10/2000 | Bergano et al. | |
| 6,141,577 A | 10/2000 | Rolland et al. | |
| 6,151,522 A | 11/2000 | Alfano et al. | |
| 6,159,445 A | 12/2000 | Klaveness et al. | |
| 6,160,826 A | 12/2000 | Swanson et al. | |
| 6,161,031 A | 12/2000 | Hochman et al. | |
| 6,162,210 A * | 12/2000 | Shadduck | 606/5 |
| 6,166,373 A | 12/2000 | Mao | |
| 6,174,291 B1 | 1/2001 | McMahon et al. | |
| 6,175,669 B1 | 1/2001 | Colston et al. | |
| 6,185,271 B1 | 2/2001 | Kinsinger | |
| 6,191,862 B1 | 2/2001 | Swanson et al. | |
| 6,193,676 B1 | 2/2001 | Winston et al. | |
| 6,198,956 B1 | 3/2001 | Dunne | |
| 6,201,989 B1 | 3/2001 | Whitehead et al. | |
| 6,208,415 B1 | 3/2001 | De Boer et al. | |
| 6,208,887 B1 | 3/2001 | Clarke | |
| 6,245,026 B1 | 6/2001 | Campbell et al. | |
| 6,249,349 B1 | 6/2001 | Lauer | |
| 6,249,381 B1 | 6/2001 | Suganuma | |
| 6,249,630 B1 | 6/2001 | Stock et al. | |
| 6,263,234 B1 | 7/2001 | Engelhardt et al. | |
| 6,264,610 B1 | 7/2001 | Zhu | |
| 6,272,268 B1 | 8/2001 | Miller et al. | |
| 6,272,376 B1 | 8/2001 | Marcu et al. | |
| 6,274,871 B1 | 8/2001 | Dukor et al. | |
| 6,282,011 B1 | 8/2001 | Tearney et al. | |
| 6,297,018 B1 | 10/2001 | French et al. | |
| 6,301,048 B1 | 10/2001 | Cao et al. | |
| 6,308,092 B1 | 10/2001 | Hoyns | |
| 6,324,419 B1 | 11/2001 | Guzelsu et al. | |
| 6,341,036 B1 | 1/2002 | Tearney et al. | |
| 6,353,693 B1 | 3/2002 | Kano et al. | |
| 6,359,692 B1 | 3/2002 | Groot | |
| 6,374,128 B1 | 4/2002 | Toida et al. | |
| 6,377,349 B1 | 4/2002 | Fercher | |
| 6,384,915 B1 | 5/2002 | Everett et al. | |
| 6,391,021 B1 * | 5/2002 | Mueller et al. | 606/7 |
| 6,393,312 B1 | 5/2002 | Hoyns | |
| 6,394,964 B1 | 5/2002 | Sievert, Jr. et al. | |
| 6,396,941 B1 | 5/2002 | Bacus et al. | |
| 6,413,253 B1 * | 7/2002 | Koop et al. | 606/27 |
| 6,413,268 B1 * | 7/2002 | Hartman | 607/94 |
| 6,421,164 B2 | 7/2002 | Tearney et al. | |
| 6,432,101 B1 * | 8/2002 | Weber et al. | 606/2 |
| 6,437,867 B2 | 8/2002 | Zeylikovich et al. | |
| 6,441,892 B2 | 8/2002 | Xiao et al. | |
| 6,441,959 B1 | 8/2002 | Yang et al. | |
| 6,445,485 B1 | 9/2002 | Frigo et al. | |
| 6,445,939 B1 | 9/2002 | Swanson et al. | |
| 6,445,944 B1 | 9/2002 | Ostrovsky | |
| 6,447,503 B1 | 9/2002 | Wynne et al. | |
| 6,459,487 B1 | 10/2002 | Chen et al. | |
| 6,463,313 B1 | 10/2002 | Winston et al. | |
| 6,469,846 B2 | 10/2002 | Ebizuka et al. | |
| 6,475,159 B1 | 11/2002 | Casscells et al. | |
| 6,475,210 B1 | 11/2002 | Phelps et al. | |
| 6,477,403 B1 | 11/2002 | Eguchi et al. | |
| 6,485,413 B1 | 11/2002 | Boppart et al. | |
| 6,485,482 B1 | 11/2002 | Belef | |
| 6,501,551 B1 * | 12/2002 | Tearney | A61B 1/00096 356/477 |
| 6,501,878 B2 | 12/2002 | Hughes et al. | |
| 6,516,014 B1 | 2/2003 | Sellin et al. | |
| 6,517,532 B1 | 2/2003 | Altshuler et al. | |
| 6,538,817 B1 | 3/2003 | Farmer et al. | |
| 6,540,391 B2 | 4/2003 | Lanzetta et al. | |
| 6,549,801 B1 | 4/2003 | Chen et al. | |
| 6,552,796 B2 | 4/2003 | Magnin et al. | |
| 6,556,305 B1 | 4/2003 | Aziz et al. | |
| 6,556,853 B1 | 4/2003 | Cabib et al. | |
| 6,558,324 B1 | 5/2003 | Von Behren et al. | |
| 6,560,259 B1 | 5/2003 | Hwang et al. | |
| 6,564,087 B1 | 5/2003 | Pitris et al. | |
| 6,564,089 B2 | 5/2003 | Izatt et al. | |
| 6,567,585 B2 | 5/2003 | De Boer et al. | |
| 6,593,101 B2 | 7/2003 | Richards-Kortum et al. | |
| 6,611,833 B1 | 8/2003 | Johnson et al. | |
| 6,615,071 B1 | 9/2003 | Casscells, III et al. | |
| 6,622,732 B2 | 9/2003 | Constantz | |
| 6,654,127 B2 | 11/2003 | Everett et al. | |
| 6,657,730 B2 | 12/2003 | Pfau et al. | |
| 6,658,278 B2 | 12/2003 | Gruhl | |
| 6,680,780 B1 | 1/2004 | Fee | |
| 6,685,885 B2 | 2/2004 | Nolte et al. | |
| 6,687,007 B1 | 2/2004 | Meigs | |
| 6,687,010 B1 | 2/2004 | Horii et al. | |
| 6,687,036 B2 | 2/2004 | Riza | |
| 6,692,430 B2 | 2/2004 | Adler | |
| 6,701,181 B2 | 3/2004 | Tang et al. | |
| 6,721,094 B1 | 4/2004 | Sinclair et al. | |
| 6,725,073 B1 | 4/2004 | Motamedi et al. | |
| 6,738,144 B1 | 5/2004 | Dogariu et al. | |
| 6,741,355 B2 | 5/2004 | Drabarek | |
| 6,741,884 B1 | 5/2004 | Freeman et al. | |
| 6,757,467 B1 | 6/2004 | Rogers | |
| 6,790,175 B1 | 9/2004 | Furusawa et al. | |
| 6,806,963 B1 | 10/2004 | Wälti et al. | |

(56) References Cited

U.S. PATENT DOCUMENTS

| | | | |
|---|---|---|---|
| 6,816,743 B2 | 11/2004 | Moreno et al. |
| 6,831,781 B2 | 12/2004 | Tearney et al. |
| 6,839,496 B1 | 1/2005 | Mills et al. |
| 6,882,432 B2 | 4/2005 | Deck |
| 6,900,899 B2 | 5/2005 | Nevis |
| 6,903,820 B2 | 6/2005 | Wang |
| 6,909,105 B1 | 6/2005 | Heintzmann et al. |
| 6,949,072 B2 | 9/2005 | Furnish et al. |
| 6,961,123 B1 | 11/2005 | Wang et al. |
| 6,980,299 B1 | 12/2005 | de Boer |
| 6,996,549 B2 | 2/2006 | Zhang et al. |
| 7,006,231 B2 | 2/2006 | Ostrovsky et al. |
| 7,006,232 B2 | 2/2006 | Rollins et al. |
| 7,019,838 B2 | 3/2006 | Izatt et al. |
| 7,027,633 B2 | 4/2006 | Foran et al. |
| 7,061,622 B2 | 6/2006 | Rollins et al. |
| 7,072,047 B2 | 7/2006 | Westphal et al. |
| 7,075,658 B2 | 7/2006 | Izatt et al. |
| 7,099,358 B1 | 8/2006 | Chong et al. |
| 7,113,288 B2 | 9/2006 | Fercher |
| 7,113,625 B2 | 9/2006 | Watson et al. |
| 7,130,320 B2 | 10/2006 | Tobiason et al. |
| 7,139,598 B2 | 11/2006 | Hull et al. |
| 7,142,835 B2 | 11/2006 | Paulus |
| 7,148,970 B2 | 12/2006 | De Boer |
| 7,177,027 B2 | 2/2007 | Hirasawa et al. |
| 7,190,464 B2 | 3/2007 | Alphonse |
| 7,230,708 B2 | 6/2007 | Lapotko et al. |
| 7,231,243 B2 | 6/2007 | Tearney et al. |
| 7,236,637 B2 | 6/2007 | Sirohey et al. |
| 7,242,480 B2 | 7/2007 | Alphonse |
| 7,267,494 B2 | 9/2007 | Deng et al. |
| 7,272,252 B2 | 9/2007 | De La Torre-Bueno et al. |
| 7,304,798 B2 | 12/2007 | Izumi et al. |
| 7,310,150 B2 | 12/2007 | Tearney et al. |
| 7,330,270 B2 | 2/2008 | O'Hara et al. |
| 7,336,366 B2 | 2/2008 | Choma et al. |
| 7,342,659 B2 | 3/2008 | Horn et al. |
| 7,355,716 B2 | 4/2008 | De Boer et al. |
| 7,355,721 B2 | 4/2008 | Quadling et al. |
| 7,359,062 B2 | 4/2008 | Chen et al. |
| 7,365,858 B2 | 4/2008 | Fang-Yen et al. |
| 7,366,376 B2 | 4/2008 | Shishkov et al. |
| 7,382,809 B2 | 6/2008 | Chong et al. |
| 7,382,949 B2 | 6/2008 | Bouma et al. |
| 7,391,520 B2 | 6/2008 | Zhou et al. |
| 7,458,683 B2 | 12/2008 | Chernyak et al. |
| 7,530,948 B2 | 5/2009 | Seibel et al. |
| 7,538,859 B2 * | 5/2009 | Tearney et al. ............... 356/35.5 |
| 7,539,530 B2 | 5/2009 | Caplan et al. |
| 7,609,391 B2 | 10/2009 | Betzig |
| 7,630,083 B2 | 12/2009 | de Boer et al. |
| 7,643,152 B2 | 1/2010 | de Boer et al. |
| 7,643,153 B2 | 1/2010 | de Boer et al. |
| 7,646,905 B2 | 1/2010 | Guittet et al. |
| 7,649,160 B2 | 1/2010 | Colomb et al. |
| 7,664,300 B2 | 2/2010 | Lange et al. |
| 7,733,497 B2 | 6/2010 | Yun et al. |
| 7,782,464 B2 | 8/2010 | Mujat et al. |
| 7,799,558 B1 | 9/2010 | Dultz |
| 7,805,034 B2 | 9/2010 | Kato et al. |
| 7,911,621 B2 | 3/2011 | Motaghiannezam et al. |
| 7,969,578 B2 | 6/2011 | Yun et al. |
| 7,973,936 B2 | 7/2011 | Dantus |
| 8,315,282 B2 | 11/2012 | Huber et al. |
| 2001/0020126 A1 | 9/2001 | Khoury |
| 2001/0036002 A1 | 11/2001 | Tearney et al. |
| 2001/0047137 A1 | 11/2001 | Moreno et al. |
| 2001/0055462 A1 | 12/2001 | Seibel |
| 2002/0016533 A1 | 2/2002 | Marchitto et al. |
| 2002/0024015 A1 | 2/2002 | Hoffmann et al. |
| 2002/0037252 A1 | 3/2002 | Toida et al. |
| 2002/0048025 A1 | 4/2002 | Takaoka |
| 2002/0048026 A1 | 4/2002 | Isshiki et al. |
| 2002/0052547 A1 | 5/2002 | Toida |
| 2002/0057431 A1 | 5/2002 | Fateley et al. |
| 2002/0064341 A1 | 5/2002 | Fauver et al. |
| 2002/0076152 A1 | 6/2002 | Hughes et al. |
| 2002/0085209 A1 | 7/2002 | Mittleman et al. |
| 2002/0086347 A1 | 7/2002 | Johnson et al. |
| 2002/0091322 A1 | 7/2002 | Chaiken et al. |
| 2002/0093662 A1 | 7/2002 | Chen et al. |
| 2002/0109851 A1 | 8/2002 | Deck |
| 2002/0113965 A1 | 8/2002 | Yun |
| 2002/0122182 A1 | 9/2002 | Everett et al. |
| 2002/0122246 A1 | 9/2002 | Tearney et al. |
| 2002/0140942 A1 | 10/2002 | Fee et al. |
| 2002/0158211 A1 | 10/2002 | Gillispie |
| 2002/0161357 A1 | 10/2002 | Rox et al. |
| 2002/0163622 A1 | 11/2002 | Magnin et al. |
| 2002/0166946 A1 | 11/2002 | Iizuka et al. |
| 2002/0168158 A1 | 11/2002 | Furusawa et al. |
| 2002/0172485 A1 | 11/2002 | Keaton et al. |
| 2002/0183623 A1 | 12/2002 | Tang et al. |
| 2002/0188204 A1 | 12/2002 | McNamara et al. |
| 2002/0196446 A1 | 12/2002 | Roth et al. |
| 2002/0198457 A1 | 12/2002 | Tearney et al. |
| 2003/0001071 A1 | 1/2003 | Mandella et al. |
| 2003/0013973 A1 | 1/2003 | Georgakoudi et al. |
| 2003/0023153 A1 | 1/2003 | Izatt et al. |
| 2003/0025917 A1 | 2/2003 | Suhami |
| 2003/0026735 A1 | 2/2003 | Nolte et al. |
| 2003/0028114 A1 | 2/2003 | Casscells, III et al. |
| 2003/0030816 A1 | 2/2003 | Eom et al. |
| 2003/0043381 A1 | 3/2003 | Fercher |
| 2003/0053673 A1 | 3/2003 | Dewaele et al. |
| 2003/0067607 A1 | 4/2003 | Wolleschensky et al. |
| 2003/0082105 A1 | 5/2003 | Fischman et al. |
| 2003/0097048 A1 | 5/2003 | Ryan et al. |
| 2003/0103212 A1 | 6/2003 | Westphal et al. |
| 2003/0108911 A1 | 6/2003 | Klimant et al. |
| 2003/0120137 A1 | 6/2003 | Pawluczyk et al. |
| 2003/0135101 A1 | 7/2003 | Webler |
| 2003/0137669 A1 | 7/2003 | Rollins et al. |
| 2003/0164952 A1 | 9/2003 | Deichmann et al. |
| 2003/0165263 A1 | 9/2003 | Hamer et al. |
| 2003/0171691 A1 | 9/2003 | Casscells, III et al. |
| 2003/0174339 A1 | 9/2003 | Feldchtein et al. |
| 2003/0191392 A1 | 10/2003 | Haldeman |
| 2003/0199769 A1 | 10/2003 | Podoleanu et al. |
| 2003/0216719 A1 | 11/2003 | Debenedictis et al. |
| 2003/0218756 A1 | 11/2003 | Chen et al. |
| 2003/0220749 A1 | 11/2003 | Chen et al. |
| 2003/0236443 A1 | 12/2003 | Cespedes et al. |
| 2004/0002650 A1 | 1/2004 | Mandrusov et al. |
| 2004/0039252 A1 | 2/2004 | Koch |
| 2004/0039298 A1 | 2/2004 | Abreu |
| 2004/0054268 A1 | 3/2004 | Esenaliev et al. |
| 2004/0072200 A1 | 4/2004 | Rigler et al. |
| 2004/0075841 A1 | 4/2004 | Van Neste et al. |
| 2004/0076940 A1 | 4/2004 | Alexander et al. |
| 2004/0077949 A1 | 4/2004 | Blofgett et al. |
| 2004/0085540 A1 | 5/2004 | Lapotko et al. |
| 2004/0086245 A1 | 5/2004 | Farroni et al. |
| 2004/0095464 A1 | 5/2004 | Miyagi et al. |
| 2004/0100631 A1 | 5/2004 | Bashkansky et al. |
| 2004/0100681 A1 | 5/2004 | Bjarklev et al. |
| 2004/0110206 A1 | 6/2004 | Wong et al. |
| 2004/0126048 A1 | 7/2004 | Dave et al. |
| 2004/0126120 A1 | 7/2004 | Cohen et al. |
| 2004/0133191 A1 | 7/2004 | Momiuchi et al. |
| 2004/0150829 A1 | 8/2004 | Koch et al. |
| 2004/0150830 A1 | 8/2004 | Chan |
| 2004/0152989 A1 | 8/2004 | Puttappa et al. |
| 2004/0165184 A1 | 8/2004 | Mizuno |
| 2004/0166593 A1 | 8/2004 | Nolte et al. |
| 2004/0188148 A1 | 9/2004 | Chen et al. |
| 2004/0189999 A1 | 9/2004 | De Groot et al. |
| 2004/0204651 A1 | 10/2004 | Freeman et al. |
| 2004/0212808 A1 | 10/2004 | Okawa et al. |
| 2004/0231682 A1 | 11/2004 | Stoltz et al. |
| 2004/0239938 A1 | 12/2004 | Izatt et al. |
| 2004/0246490 A1 | 12/2004 | Wang |
| 2004/0246583 A1 | 12/2004 | Mueller et al. |

(56) References Cited

U.S. PATENT DOCUMENTS

| | | |
|---|---|---|
| 2004/0247268 A1 | 12/2004 | Ishihara et al. |
| 2004/0254474 A1* | 12/2004 | Seibel ............... A61B 5/0062 600/473 |
| 2004/0258106 A1 | 12/2004 | Araujo et al. |
| 2004/0263843 A1 | 12/2004 | Knopp et al. |
| 2005/0004453 A1 | 1/2005 | Tearney et al. |
| 2005/0018133 A1 | 1/2005 | Huang et al. |
| 2005/0018200 A1 | 1/2005 | Guillermo et al. |
| 2005/0018201 A1 | 1/2005 | De Boer et al. |
| 2005/0035295 A1 | 2/2005 | Bouma et al. |
| 2005/0036150 A1 | 2/2005 | Izatt et al. |
| 2005/0046837 A1 | 3/2005 | Izumi et al. |
| 2005/0049488 A1 | 3/2005 | Homan |
| 2005/0057680 A1 | 3/2005 | Agan |
| 2005/0057756 A1 | 3/2005 | Fang-Yen et al. |
| 2005/0059894 A1 | 3/2005 | Zeng et al. |
| 2005/0065421 A1 | 3/2005 | Burckhardt et al. |
| 2005/0075547 A1 | 4/2005 | Wang |
| 2005/0083534 A1 | 4/2005 | Riza et al. |
| 2005/0119567 A1 | 6/2005 | Choi et al. |
| 2005/0119643 A1* | 6/2005 | Sobol et al. ............. 606/9 |
| 2005/0128488 A1 | 6/2005 | Yelin et al. |
| 2005/0165303 A1 | 7/2005 | Kleen et al. |
| 2005/0171438 A1 | 8/2005 | Chen et al. |
| 2005/0190372 A1 | 9/2005 | Dogariu et al. |
| 2005/0197530 A1 | 9/2005 | Daniel et al. |
| 2005/0221270 A1 | 10/2005 | Connelly et al. |
| 2005/0254059 A1 | 11/2005 | Alphonse |
| 2005/0254061 A1 | 11/2005 | Alphonse et al. |
| 2006/0020172 A1 | 1/2006 | Luerssen et al. |
| 2006/0033923 A1 | 2/2006 | Hirasawa et al. |
| 2006/0039004 A1 | 2/2006 | De Boer et al. |
| 2006/0093276 A1 | 5/2006 | Bouma et al. |
| 2006/0103850 A1 | 5/2006 | Alphonse et al. |
| 2006/0106375 A1 | 5/2006 | Werneth et al. |
| 2006/0146339 A1 | 7/2006 | Fujita et al. |
| 2006/0155193 A1 | 7/2006 | Leonardi et al. |
| 2006/0164639 A1 | 7/2006 | Horn et al. |
| 2006/0167363 A1 | 7/2006 | Bernstein et al. |
| 2006/0171503 A1 | 8/2006 | O'Hara et al. |
| 2006/0184048 A1 | 8/2006 | Saadat et al. |
| 2006/0189928 A1 | 8/2006 | Camus et al. |
| 2006/0193352 A1 | 8/2006 | Chong et al. |
| 2006/0224053 A1 | 10/2006 | Black et al. |
| 2006/0244973 A1 | 11/2006 | Yun et al. |
| 2006/0279742 A1 | 12/2006 | Tearney |
| 2007/0002435 A1 | 1/2007 | Ye et al. |
| 2007/0019208 A1 | 1/2007 | Toida et al. |
| 2007/0024860 A1 | 2/2007 | Tobiason et al. |
| 2007/0035743 A1 | 2/2007 | Vakoc et al. |
| 2007/0038040 A1 | 2/2007 | Cense et al. |
| 2007/0048818 A1 | 3/2007 | Rosen et al. |
| 2007/0070496 A1 | 3/2007 | Gweon et al. |
| 2007/0076217 A1 | 4/2007 | Baker et al. |
| 2007/0086013 A1 | 4/2007 | De Lega et al. |
| 2007/0086017 A1 | 4/2007 | Buckland et al. |
| 2007/0091317 A1 | 4/2007 | Freischlad et al. |
| 2007/0133002 A1 | 6/2007 | Wax et al. |
| 2007/0188855 A1 | 8/2007 | Shishkov et al. |
| 2007/0203404 A1 | 8/2007 | Zysk et al. |
| 2007/0208225 A1 | 9/2007 | Czaniera et al. |
| 2007/0223006 A1 | 9/2007 | Tearney et al. |
| 2007/0233056 A1 | 10/2007 | Yun |
| 2007/0233396 A1 | 10/2007 | Tearney et al. |
| 2007/0236700 A1 | 10/2007 | Yun et al. |
| 2007/0253901 A1 | 11/2007 | Deng et al. |
| 2007/0258094 A1 | 11/2007 | Izatt et al. |
| 2007/0263226 A1 | 11/2007 | Kurtz et al. |
| 2007/0276185 A1* | 11/2007 | Gono et al. ............... 600/156 |
| 2007/0291277 A1 | 12/2007 | Everett et al. |
| 2008/0002197 A1 | 1/2008 | Sun et al. |
| 2008/0007734 A1 | 1/2008 | Park et al. |
| 2008/0013960 A1 | 1/2008 | Tearney et al. |
| 2008/0021275 A1 | 1/2008 | Tearney et al. |
| 2008/0049220 A1 | 2/2008 | Izzia et al. |
| 2008/0070323 A1 | 3/2008 | Hess et al. |
| 2008/0094613 A1 | 4/2008 | de Boer et al. |
| 2008/0094637 A1 | 4/2008 | de Boer et al. |
| 2008/0097225 A1 | 4/2008 | Tearney et al. |
| 2008/0097709 A1 | 4/2008 | de Boer et al. |
| 2008/0100837 A1 | 5/2008 | de Boer et al. |
| 2008/0139906 A1 | 6/2008 | Bussek et al. |
| 2008/0152353 A1 | 6/2008 | de Boer et al. |
| 2008/0154090 A1 | 6/2008 | Hashimshony |
| 2008/0192236 A1 | 8/2008 | Smith et al. |
| 2008/0201081 A1 | 8/2008 | Reid |
| 2008/0204762 A1 | 8/2008 | Izatt et al. |
| 2008/0218696 A1 | 9/2008 | Mir |
| 2008/0226029 A1 | 9/2008 | Weir et al. |
| 2008/0228086 A1 | 9/2008 | Ilegbusi |
| 2008/0234560 A1 | 9/2008 | Nomoto et al. |
| 2008/0252901 A1 | 10/2008 | Shimizu |
| 2008/0265130 A1 | 10/2008 | Colomb et al. |
| 2008/0297806 A1 | 12/2008 | Motaghiannezam |
| 2008/0308730 A1 | 12/2008 | Vizi et al. |
| 2009/0004453 A1 | 1/2009 | Murai et al. |
| 2009/0005691 A1 | 1/2009 | Huang |
| 2009/0011948 A1 | 1/2009 | Uniu et al. |
| 2009/0012368 A1 | 1/2009 | Banik et al. |
| 2009/0044799 A1 | 2/2009 | Bangsaruntip et al. |
| 2009/0051923 A1 | 2/2009 | Andres et al. |
| 2009/0131801 A1 | 5/2009 | Suter et al. |
| 2009/0192358 A1 | 7/2009 | Yun |
| 2009/0196477 A1 | 8/2009 | Cense et al. |
| 2009/0209834 A1 | 8/2009 | Fine |
| 2009/0273777 A1 | 11/2009 | Yun et al. |
| 2009/0281390 A1 | 11/2009 | Quinjun et al. |
| 2009/0290156 A1 | 11/2009 | Popescu et al. |
| 2009/0305309 A1 | 12/2009 | Chien et al. |
| 2009/0306520 A1 | 12/2009 | Schmitt et al. |
| 2009/0323056 A1 | 12/2009 | Yun et al. |
| 2010/0002241 A1 | 1/2010 | Hirose |
| 2010/0086251 A1 | 4/2010 | Xu et al. |
| 2010/0094576 A1 | 4/2010 | de Boer et al. |
| 2010/0145145 A1 | 6/2010 | Shi et al. |
| 2010/0150467 A1 | 6/2010 | Zhao et al. |
| 2010/0261995 A1 | 10/2010 | Mckenna et al. |
| 2011/0028967 A1 | 2/2011 | Rollins et al. |
| 2011/0160681 A1 | 6/2011 | Dacey, Jr. et al. |
| 2011/0218403 A1 | 9/2011 | Tearney et al. |

FOREIGN PATENT DOCUMENTS

| | | |
|---|---|---|
| DE | 4309056 | 9/1994 |
| DE | 19542955 | 5/1997 |
| DE | 10351319 | 6/2005 |
| DE | 2007-030835 | 3/2007 |
| EP | 0110201 | 6/1984 |
| EP | 0251062 | 1/1988 |
| EP | 0617286 | 2/1994 |
| EP | 0590268 | 4/1994 |
| EP | 0697611 | 2/1996 |
| EP | 0728440 | 8/1996 |
| EP | 0933096 | 8/1999 |
| EP | 1324051 | 7/2003 |
| EP | 1426799 | 6/2004 |
| EP | 2149776 | 2/2010 |
| FR | 2738343 | 8/1995 |
| GB | 1257778 | 12/1971 |
| GB | 2030313 | 4/1980 |
| GB | 2209221 | 5/1989 |
| GB | 2298054 | 8/1996 |
| JP | 6073405 | 4/1985 |
| JP | 361040633 | 3/1986 |
| JP | 62-188001 | 6/1989 |
| JP | H 03126449 | 5/1991 |
| JP | 04-056907 | 2/1992 |
| JP | 20040056907 | 2/1992 |
| JP | 4135550 | 5/1992 |
| JP | 4135551 | 6/1992 |
| JP | 5509417 | 11/1993 |
| JP | H8-136345 | 5/1996 |
| JP | H08-160129 | 6/1996 |
| JP | 9-10213 | 1/1997 |

(56) References Cited

FOREIGN PATENT DOCUMENTS

| | | |
|---|---|---|
| JP | 9-230248 | 9/1997 |
| JP | 10-213485 | 8/1998 |
| JP | 10-267631 | 10/1998 |
| JP | 10-267830 | 10/1998 |
| JP | 2259617 | 10/1999 |
| JP | H 11267131 | 10/1999 |
| JP | 2000-023978 | 1/2000 |
| JP | 2000-046729 | 2/2000 |
| JP | 2000-121961 | 4/2000 |
| JP | 2000-504234 | 4/2000 |
| JP | 2000504234 | 4/2000 |
| JP | 2000-126116 | 5/2000 |
| JP | 2000-131222 | 5/2000 |
| JP | 2001-4447 | 1/2001 |
| JP | 2001-500026 | 1/2001 |
| JP | 2001-104315 | 4/2001 |
| JP | 2001-174404 | 6/2001 |
| JP | 2001-174744 | 6/2001 |
| JP | 2001-507251 | 6/2001 |
| JP | 2001-508340 | 6/2001 |
| JP | 2007-539336 | 6/2001 |
| JP | 2001-212086 | 8/2001 |
| JP | 2008-533712 | 8/2001 |
| JP | 2001-264246 | 9/2001 |
| JP | 2001-515382 | 9/2001 |
| JP | 2001-525580 | 12/2001 |
| JP | 2002-503134 | 1/2002 |
| JP | 2002-035005 | 2/2002 |
| JP | 2002-205434 | 2/2002 |
| JP | 2002-095663 | 4/2002 |
| JP | 2002-113017 | 4/2002 |
| JP | 2002-148185 | 5/2002 |
| JP | 2002-516586 | 6/2002 |
| JP | 2002-214127 | 7/2002 |
| JP | 2002-214128 | 7/2002 |
| JP | 2002214127 | 7/2002 |
| JP | 2003-014585 | 1/2003 |
| JP | 2003-504627 | 2/2003 |
| JP | 20030035659 | 2/2003 |
| JP | 2003-512085 | 4/2003 |
| JP | 2003-513278 | 4/2003 |
| JP | 2003-516531 | 5/2003 |
| JP | 2004-028970 | 1/2004 |
| JP | 2004-037165 | 2/2004 |
| JP | 2004-057652 | 2/2004 |
| JP | 2004-089552 | 3/2004 |
| JP | 2004-113780 | 4/2004 |
| JP | 2004-514920 | 5/2004 |
| JP | 2004-258144 | 9/2004 |
| JP | 2004-317437 | 11/2004 |
| JP | 2005500108 | 1/2005 |
| JP | 2005-062850 | 3/2005 |
| JP | 2005-110208 | 4/2005 |
| JP | 2005-510323 | 4/2005 |
| JP | 2005-156540 | 6/2005 |
| JP | 2005-516187 | 6/2005 |
| JP | 2005-195485 | 7/2005 |
| JP | 2005-241872 | 9/2005 |
| JP | 2006-237359 | 9/2006 |
| JP | 2007-500059 | 1/2007 |
| JP | 2007-075403 | 3/2007 |
| JP | 2007-83053 | 4/2007 |
| JP | 2007-524455 | 8/2007 |
| JP | 2007271761 | 10/2007 |
| JP | 2003-102672 | 4/2012 |
| RU | 2149464 | 5/2000 |
| RU | 2209094 | 7/2003 |
| RU | 2213421 | 9/2003 |
| RU | 2242710 | 12/2004 |
| RU | 2255426 | 6/2005 |
| RU | 2108122 | 6/2006 |
| WO | 7900841 | 10/1979 |
| WO | 9835203 | 8/1988 |
| WO | 9201966 | 2/1992 |
| WO | WO 92/03977 A2 | 3/1992 |
| WO | 9216865 | 10/1992 |
| WO | 9219930 | 11/1992 |
| WO | 9303672 | 3/1993 |
| WO | 9216865 | 10/1993 |
| WO | 9533971 | 12/1995 |
| WO | 1996-02184 | 2/1996 |
| WO | 1996-04839 | 2/1996 |
| WO | 9628212 | 9/1996 |
| WO | 9732182 | 9/1997 |
| WO | 9800057 | 1/1998 |
| WO | 9801074 | 1/1998 |
| WO | 9814132 | 4/1998 |
| WO | 1998-35203 | 8/1998 |
| WO | 9838907 | 9/1998 |
| WO | 9846123 | 10/1998 |
| WO | 9848838 | 11/1998 |
| WO | 1998048846 | 11/1998 |
| WO | 9905487 | 2/1999 |
| WO | 1999044089 | 2/1999 |
| WO | 99-28856 | 6/1999 |
| WO | 1999-45838 | 9/1999 |
| WO | 9944089 | 9/1999 |
| WO | 1999-45338 | 10/1999 |
| WO | 9957507 | 11/1999 |
| WO | 2000-42906 | 7/2000 |
| WO | 2000-43730 | 7/2000 |
| WO | 0058766 | 10/2000 |
| WO | 2001-04828 | 1/2001 |
| WO | 0101111 | 1/2001 |
| WO | 0108579 | 2/2001 |
| WO | 2001027679 | 4/2001 |
| WO | 2001-033215 | 5/2001 |
| WO | 2001-38820 | 5/2001 |
| WO | 2011-055376 | 5/2001 |
| WO | 0138820 | 5/2001 |
| WO | 2001-42735 | 6/2001 |
| WO | 0142735 | 6/2001 |
| WO | WO 01/78830 | 10/2001 |
| WO | 200142786 | 11/2001 |
| WO | 2002-037075 | 5/2002 |
| WO | 0236015 | 5/2002 |
| WO | 0238040 | 5/2002 |
| WO | 20020037075 | 5/2002 |
| WO | 2002-045572 | 6/2002 |
| WO | 2002-068853 | 6/2002 |
| WO | 2002-054027 | 7/2002 |
| WO | 0254027 | 7/2002 |
| WO | 2002053050 | 7/2002 |
| WO | 2002-083003 | 10/2002 |
| WO | 2002084263 | 10/2002 |
| WO | 2003-003903 | 1/2003 |
| WO | WO 03/003903 | 1/2003 |
| WO | 2003-012405 | 2/2003 |
| WO | 2003-013624 | 2/2003 |
| WO | 20030013624 | 2/2003 |
| WO | 03020119 | 3/2003 |
| WO | 03052478 | 6/2003 |
| WO | 2003046495 | 6/2003 |
| WO | 2003046636 | 6/2003 |
| WO | 03062802 | 7/2003 |
| WO | 2003062802 | 7/2003 |
| WO | 20030053226 | 7/2003 |
| WO | 03-088826 | 10/2003 |
| WO | 2003-088826 | 10/2003 |
| WO | 2003105678 | 12/2003 |
| WO | 2004034869 | 4/2004 |
| WO | 2004-037068 | 5/2004 |
| WO | 2004-043251 | 5/2004 |
| WO | WO 2004/037068 | 5/2004 |
| WO | 2004057266 | 7/2004 |
| WO | 20040066824 | 8/2004 |
| WO | WO 2004/064623 * | 8/2004 |
| WO | 2004-073501 | 9/2004 |
| WO | 2004088361 | 10/2004 |
| WO | 2004-100789 | 11/2004 |
| WO | 2004-105598 | 12/2004 |
| WO | 04105598 | 12/2004 |
| WO | 20050000115 | 1/2005 |
| WO | WO 2005025400 A2 * | 3/2005 ............ A61B 18/20 |

(56) References Cited

FOREIGN PATENT DOCUMENTS

| | | | | |
|---|---|---|---|---|
| WO | 2005-045362 | 5/2005 | | |
| WO | 2005-047813 | 5/2005 | | |
| WO | 2005047813 | 5/2005 | | |
| WO | 2005054780 | 6/2005 | | |
| WO | WO 2005025400 A3 * | 6/2005 | ............ | A61B 18/20 |
| WO | 2005082225 | 9/2005 | | |
| WO | 20050822225 | 9/2005 | | |
| WO | 2006004743 | 1/2006 | | |
| WO | 2006-020605 | 2/2006 | | |
| WO | 2006014392 | 2/2006 | | |
| WO | WO 2006/020605 | 2/2006 | | |
| WO | 2006039091 | 4/2006 | | |
| WO | 20060038876 | 4/2006 | | |
| WO | 2006-050320 | 5/2006 | | |
| WO | 2006-058187 | 6/2006 | | |
| WO | 2006059109 | 6/2006 | | |
| WO | 2006124860 | 11/2006 | | |
| WO | 2006-131859 | 12/2006 | | |
| WO | 2006130797 | 12/2006 | | |
| WO | 102005034443 | 2/2007 | | |
| WO | 2007028531 | 3/2007 | | |
| WO | 2007038787 | 4/2007 | | |
| WO | 2007083138 | 7/2007 | | |
| WO | 2007084995 | 7/2007 | | |
| WO | 2009-033064 | 3/2009 | | |
| WO | 20090153929 | 12/2009 | | |
| WO | 2011-080713 | 7/2011 | | |

OTHER PUBLICATIONS

Goldberg et al., "Real time monitoring of laser ablation for treatment of Barrett's Esophagus by Optical Coherence Tomography" Biomedical Topical Meeting held on Apr. 14, 2004 in Miami Beach, Florida, USA.*

Boppart et al., High-Resolution Optical Coherence Tomography-Guided Laser Ablation of Surgical Tissue, Sep. 17, 1998, Journal of Surgical Research vol. 82, pp. 275-284.*

Kuznetsova et al., "Comparative analysis of two modalities for speckle contrast monitoring of tissue structure modification", Saratov Fall Meeting 2003: Coherent Optics of Ordered and Random Media IV, Proc. of SPIE vol. 5475, pp. 126-129.*

Yun et al., "High-speed optical frequency-domain imaging" , Nov. 3, 2003, vol. 11, No. 22, Optics Express, pp. 2953-2963.*

De Boer et al., "Two-dimensional birefrigence imaging in biological tissue by polarization-sensitive optical coherence tomography", Gune 15, 1997, vol. 22, No. 12, Optical Letters, pp. 934-936.*

D. Huang et al., "Optical Coherence Tomography," Science, vol. 254, pp. 1178-1181, Nov. 1991.

Tearney et al., "High-Speed Phase—and Group Delay Scanning with a Grating Based Phase Control Delay Line," Optics Letters, vol. 22, pp. 1811-1813, Dec. 1997.

Rollins, et al., "In Vivo Video Rate Optical Coherence Tomography," Optics Express, vol. 3, pp. 219-229, Sep. 1998.

Saxer, et al., High Speed Fiber-Based Polarization-Sensitive Optical Coherence Tomography of in Vivo Human Skin, Optical Society of America, vol. 25, pp. 1355-1357, Sep. 2000.

Oscar Eduardo Martinex, "3000 Times Grating Compress or with Positive Group Velocity Dispersion," IEEE, vol. QE-23, pp. 59-64, Jan. 1987.

Kulkarni, et al., "Image Enhancement in Optical Coherence Tomography Using Deconvolution," Electronics Letters, vol. 33, pp. 1365-1367, Jul. 1997.

Bashkansky, et al., "Signal Processing for Improving Field Cross-Correlation Function in Optical Coherence Tomography," Optics & Photonics News, vol. 9, pp. 8137-3138, May 1998.

Yung et al., "Phase-Domain Processing of Optical Coherence Tomography Images," Journal of Biomedical Optics, vol. 4, pp. 125-136, Jan. 1999.

Tearney, et al., "In Vivo Endoscopic Optical Biopsy with Optical Coherence Tomography," Science, vol. 276, Jun. 1997.

W. Drexler et al., "In Vivo Ultrahigh-Resolution Optical Coherence Tomography," Optics Letters vol. 24, pp. 1221-1223, Sep. 1999.

Abbas, G.L., V.W.S. Chan et al., "Local-Oscillator Excess-Noise Suppression for Homodyne and Heterodyne-Dectection," Optics Letters, vol. 8, pp. 419-421, Aug. 1983 issue.

Agrawal, G.P., "Population Pulsations and Nondegenerate 4-Wave Mixing in Semiconductor-Lasers and Amplifiers," Journal of the Optical Society of America B—Optical Physics, vol. 5, pp. 147-159, Jan. 1998.

Ballif, J. et al., "Rapid and Scalable Scans at 21 m/s in optical Low-Coherence Reflectometry," Optics Letters, vol. 22, pp. 757-759, Jun. 1997.

Barfuss H. et al., "Modified Optical Frequency-Domain Reflectometry with High Spatial-Resolution for Components of Integrated Optic Systems," Journal of Lightwave Technology, vol. 7, pp. 3-10, Jan. 1989.

Beaud, P. et al., "Optical Reflectometry with Micrometer Resolution for the Investigation of Integrated Optical-Devices," Leee Journal of Quantum Electronics, vol. 25, pp. 755-759, Apr. 1989.

Bouma, Brett et al., "Power-Efficient Nonreciprocal Interferometer and Linear-Scanning Fiber-Optic Optic Catheter for Optical Coherence Tomography,", Optics Letters, vol. 24, pp. 531-533, Apr. 1999.

Brinkmeyer, E. et al., "Efficient Algorithm Non-Equidistant Interpolation of Sampled Data," Electronics Letters, vol. 28, p. 693, Mar. 1992.

Brinkmeyer, E. et al., "High-Resolution OCDR in Dispersive Wave-Guides," Electronics Letters, vol. 26, pp. 413-414, Mar. 1990.

Chinn, S.R. et al., "Optical Coherence Tomography Using a Frequency-Tunable Optical Source," Optics Letters, vol. 22, pp. 340-342, Mar. 1997.

Danielson, B.L. et al., "Absolute Optical Ranging Using Low Coherence Interferometry," Applied Optics, vol. 30, p. 2975, Jul. 1991.

Dorrer, C. et al., "Spectral Resolution and Sampling Issues in Fourier-Transform Spectral Interferometry," Journal of the Optical Society of America B—Optical Physics, vol. 17, pp. 1795-1802, Oct. 2000.

Dudley, J.M. et al., "Cross-Correlation Frequency Resolved Optical Gating Analysis of Broadband Continuum Generation in Photonic Crystal Fiber: Simulations and Experiments," Optics Express, vol. 10, p. 1215, Oct. 2002.

Eickhoff, W. et al., "Optical Frequency-Domain Reflectometry in Single-Mode Fiber," Applied Physics Letters, vol. 39, pp. 693-695, 1981.

Fercher, Adolf "Optical Coherence Tomography," Journal of Biomedical Optics, vol. 1, pp. 157-173, Apr. 1996.

Ferreira, L.A. et al., "Polarization-Insensitive Fiberoptic White-Light Interferometry," Optics Communications, vol. 114, pp. 386-392, Feb. 1995.

Fujii, Yohji, "High-Isolation Polarization-Independent Optical Circulator", Journal of Lightwave Technology, vol. 9, pp. 1239-1243, Oct. 1991.

Glance, B., "Polarization Independent Coherent Optical Receiver," Journal of Lightwave Technology, vol. LT-5, p. 274, Feb. 1987.

Glombitza, U., "Coherent Frequency-Domain Reflectometry for Characterization of Single-Mode Integrated-Optical Wave-Guides," Journal of Lightwave Technology, vol. 11, pp. 1377-1384, Aug. 1993.

Golubovic, B. et al., "Optical Frequency-Domain Reflectometry Using Rapid Wavelength Tuning of a Cr4+:Forsterite Laser," Optics Letters, vol. 11, pp. 1704-1706, Nov. 1997.

Haberland, U. H. P. et al., "Chirp Optical Coherence Tomography of Layered Scattering Media," Journal of Biomedical Optics, vol. 3, pp. 259-266, Jul. 1998.

Hammer, Daniel X. et al., "Spectrally Resolved White-Light Interferometry for Measurement of Ocular Dispersion," Journal of the Optical Society of America A—Optics Image Science and Vision, vol. 16, pp. 2092-2102, Sep. 1999.

Harvey, K. C. et al., "External-Cavity Grating Diode-Laser Using a Grazing-Incidence Diffraction Grating," Optics Letters, vol. 16, pp. 910-912, Jun. 1991.

(56) References Cited

OTHER PUBLICATIONS

Hausler, Gerd et al., "'Coherence Radar' and 'Spectral Radar' New Tools for Dermatological Diagnosis," *Journal of Biomedical Optics*, vol. 3, pp. 21-31, Jan. 1998.
Hee, Michael R. et al., "Polarization-Sensitive Low-Coherence Reflectometer for Birefringence Characterization and Ranging," *Journal of the Optical Society of America B (Optical Physics)*, vol. 9, p. 903-908, Jun. 1992.
Hotate Kazuo et al., "Optical Coherence Domain Reflectometry by Synthesis of Coherence Function," *Journal of Lightwave Technology*, vol. 11, pp. 1701-1710, Oct. 1993.
Inoue, Kyo et al., "Nearly Degenerate 4-Wave-Mixing in a Traveling-Wave Semiconductor-Laser Amplifier," *Applied Physics Letters*, vol. 51, pp. 1051-1053, 1987.
Ivanov, A. P. et al., "New Method for High-Range Resolution Measurements of Light Scattering in Optically Dense Inhomogeneous Media," *Optics Letters*, vol. 1, pp. 226-228, Dec. 1977.
Ivanov, A. P. et al., "Interferometric Study of the Spatial Structure of a Light-Scattering Medium," *Journal of Applied Spectroscopy*, vol. 28, pp. 518-525, 1978.
Kazovsky, L. G. et al., "Heterodyne Detection Through Rain, Snow, and Turbid Media: Effective Receiver Size at Optical Through Millimeter Wavelenghths," *Applied Optics*, vol. 22, pp. 706-710, Mar. 1983.
Kersey, A. D. et al., "Adaptive Polarization Diversity Receiver Configuration for Coherent Optical Fiber Communication," *Electronics Letters*, vol. 25, pp. 275-277, Feb. 1989.
Kohlhaas, Andreas et al., "High-Resolution OCDR for Testing Integrated-Optical Waveguides: Dispersion-Corrupted Experimental Data by a Numerical Algorithm," *Journal of Lightwave Technology*, vol. 9, pp. 1493-1502, Nov. 1991.
Larkin, Kieran G., "Efficient Nonlinear Algorithm for Envelope Detection in White Light Interferometry," *Journal of the Optical Society of America A—Optics Image Science and Vision*, vol. 13, pp. 832-843, Apr. 1996.
Leitgeb, R. et al., "Spectral measurement of Absorption by Spectroscopic Frequency-Domain Optical Coherence Tomography," *Optics Letters*, vol. 25, pp. 820-822, Jun. 2000.
Lexer, F., et al., "Wavelength-Tuning Interforometry of Intraocular Distances," *Applied Optics*, vol. 36, pp. 6548-6553, Sep. 1997.
Naganuma, Kazunori et al., "Group-Delay Measurement Using the Fourier-Transform of an Interferometric Cross-Correlation Generated by White Light," *Optics Letters*, vol. 15, pp. 393-395, Apr. 1990.
Okoshi,Takanori, "Polarization-State Control Schemes Heterodyne or Homodyne Optical Fiber Communications," *Journal of Lightwave Technology*, vol. LT-3, pp. 1232-1237, Dec. 1995.
Passy, R. et al., "Experimental and Theoretical Investigations of Coherent OFDR with Semiconductor-Laser Sources," *Journal of Lightwave Technology*, vol. 12, pp. 1622-1630, Sep. 1994.
Podoleanu, Adrian G., "Unbalanced Versus Balanced Operation in an Optical Coherence Tomography System," *Applied Optics*, vol. 39, pp. 173-182, Jan. 2000.
Price, J. H. V. et al., "Tunable, Femtosecond Pulse Source Operating in the Range 1.06-1.33 mu m Based on an Yb3+-doped Holey Fiber Amplifier," *Journal of the Optical Society of America B—Optical Physics*, vol. 19, pp. 1286-1294, Jun. 2002.
Schmitt, J. M. et al, "Measurement of Optical-Properties of Biological Tissues By Low-Coherence Reflectometry," *Applied Optics*, vol. 32, pp. 6032-6042, Oct. 1993.
Silberberg, Y. et al., "Passive-Mode Locking of a Semiconductor Diode-Laser," *Optics Letters*, vol. 9, pp. 507-509, Nov. 1984
Smith, L. Montgomery et al., "Absolute Displacement Measurements Using Modulation of the Spectrum of White-Light in a Michelson Interferometer," *Applied Optics*, vol. 28, pp. 3339-3342, Aug. 1989
Sonnenschein, C. M. et al., "Signal-To-Noise Relationships for Coaxial Systems that Heterodyne Backscatter from Atmosphere," *Applied Optics*, vol. 10, pp. 1600-1604, Jul. 1971.
Sorin, W. V. et al., "Measurement of Rayleigh Backscattering at 1.55 mu m with 32 mu m Spatial Resolution," *IEEE Photonics Technology Letters*, vol. 4, pp. 374-376, Apr. 1992.
Sorin, W. V. et al., "A Simple Intensity Noise-Reduction Technique for Optical Low-Coherence Reflectometry," *IEEE Photonics Technology Letters*, vol. 4, pp. 1404-1406, Dec. 1992.
Swanson, E. A. et al., "High-Speed Optical Coherence Domain Reflectometry," *Optics Letters*, vol. 17, pp. 151-153, Jan. 1992
Takada, K. et al., "High-Resolution OFDR with Incorporated Fiberoptic Frequency Encoder," *IEEE Photonics Technology Letters*, vol. 4, pp. 1069-1072, Sep. 1992.
Takada, Kazumasa et al., "Narrow-Band light Source with Acoustooptic Tunable Filter for Optical Low-Coherence Reflectometry," *IEEE Photonics Technology Letters*, vol. 8, pp. 658-660, May 1996
Takada, Kazumasa et al., "New Measurement System for Fault Location in Optical Wave-Guide Devices Based on an Interometric-Technique," *Applied Optics*, vol. 26, pp. 1603-1606, May 1987.
Tateda, Mitsuhiro et al., "Interferometric Method for Chromatic Dispersion Measurement in a Single-Mode Optical Fiber," *IEEE Journal of Quantum Electronics*, vol. 17, pp. 404-407, Mar. 1981.
Toide, M. et al., "Two-Dimensional Coherent Detection Imaging in Multiple Scattering Media Based the Directional Resolution Capability of the Optical Heterodyne Method," *Applied Physics B (Photophysics and Laser Chemistry)*, vol. B52, pp. 391-394, 1991.
Trutna, W. R. et al., "Continuously Tuned External-Cavity Semiconductor-Laser," *Journal of Lightwave Technology*, vol. 11, pp. 1279-1286, Aug. 1993.
Uttam, Deepak et al., "Precision Time Domain Reflectometry in Optical Fiber Systems Using a Frequency Modulated Continuous Wave Ranging Technology," *Journal of Lightwave Technology*, vol. 3, pp. 971-977, Oct. 1985.
Von Der Weid, J. P. et al., "On the Characterization of Optical Fiber Network Components with Optical Frequency Domain Reflectometry," *Journal of Lightwave Technology*, vol. 15, pp. 1131-1141, Jul. 1997.
Wysocki, P.F. et al., "Broad-Spectrum, Wavelength-Swept, Erbium-Doped Fiber Laser at 1.55-Mu-M," *Optics Letters*, vol. 15, pp. 879-881, Aug. 1990.
Youngquist, Robert C. et al., "Optical Coherence-Domain Reflectometry—A New Optical Evaluation Technique," *Optics Letters*, vol. 12, pp. 158-160, Mar. 1987.
Yun, S. H. et al., "Wavelength-Swept Fiber Laser with Frequency Shifted Feedback and Resonantly Swept Intra-Cavity Acoustooptic Tunable Filter," *IEEE Journal of Selected Topics in Quantum Electronics*, vol. 3, pp. 1087-1096, Aug. 1997.
Yun, S. H. et al., "Interrogation of Fiber Grating Sensor Arrays with a Wavelength-Swept Fiber Laser," *Optics Letters*, vol. 23, pp. 843-845, Jun. 1998.
Yung, K. M., "Phase-Domain Processing of Optical Coherence Tomography Images," *Journal of Biomedical Optics*, vol. 4, pp. 125-136, Jan. 1999.
Zhou, Xiao-Qun et al., "Extended-Range FMCW Reflectometry Using an optical Loop with a Frequency Shifter," *IEEE Photonics Technology Letters*, vol. 8, pp. 248-250, Feb. 1996.
Zorabedian, Paul et al., "Tuning Fidelity of Acoustooptically Controlled External Cavity Semiconductor-Lasers," *Journal of Lightwave Technology*, vol. 13, pp. 62-66, Jan. 1995.
Victor S. Y. Lin et al., "A Porous Silicon-Based Optical Interferometric Biosensor," *Science Magazine*, vol. 278, pp. 840-843, Oct. 31, 1997.
De Boer, Johannes F. et al., "Review of Polarization Sensitive Optical Coherence Tomography and Stokes Vector Determination," *Journal of Biomedical Optics*, vol. 7, No. 3, Jul. 2002, pp. 359-371.
Jiao, Shuliang et al., "Depth-Resolved Two-Dimensional Stokes Vectors of Backscattered Light and Mueller Matrices of Biological Tissue Measured with Optical Coherence Tomography," *Applied Optics*, vol. 39, No. 34, Dec. 1, 2000, pp. 6318-6324.
Park, B. Hyle et al., "In Vivo Burn Depth Determination by High-Speed Fiber-Based Polarization Sensitive Optical Coherence Tomography," *Journal of Biomedical Optics*, vol. 6 No. 4, Oct. 2001, pp. 474-479
Roth, Jonathan E. et al., "Simplified Method for Polarization-Sensitive Optical Coherence Tomography," *Optics Letters*, vol. 26, No. 14, Jul. 15, 2001, pp. 1069-1071.

(56) References Cited

OTHER PUBLICATIONS

Hitzenberger, Christopher K. et al., "Measurement and Imaging of Birefringence and Optic Axis Orientation by Phase Resolved Polarization Sensitive Optical Coherence Tomography," *Optics Express*, vol. 9, No. 13, Dec. 17, 2001, pp. 780-790.
Wong, Brian J.F. et al., "Optical Coherence Tomography of the Rat Cochlea," Journal of *Biomedical Optics*, vol. 5, No. 4, Oct. 2000, pp. 367-370.
Yao, Gang et al., "Propagation of Polarized Light in Turbid Media: Simulated Animation Sequences," *Optics Express*, vol. 7, No. 5, Aug. 28, 2000, pp. 198-203.
Wang, Xiao-Jun et al., "Characterization of Dentin and Enamel by Use of Optical Coherence Tomography," *Applied Optics*, vol. 38, No. 10, Apr. 1, 1999, pp. 2092-2096.
De Boer, Johannes F. et al., "Determination of the Depth-Resolved Stokes Parameters of Light Backscattered from Turbid Media by use of Polarization-Sensitive Optical Coherence Tomography," *Optics Letters*, vol. 24, No. 5, Mar. 1, 1999, pp. 300-302.
Ducros, Mathieu G. et al., "Polarization Sensitive Optical Coherence Tomography of the Rabbit Eye," *IEEE Journal of Selected Topics in Quantum Electronics*, vol. 5, No. 4, Jul./Aug. 1999, pp. 1159-1167.
Groner, Warren et al., "Orthogonal Polarization Spectral Imaging: A New Method for Study of the Microcirculation," *Nature Medicine Inc.*, vol. 5 No. 10, Oct. 1999, pp. 1209-1213.
De Boer, Johannes F. et al., "Polarization Effects in Optical Coherence Tomography of Various Viological Tissues," *IEEE Journal of Selected Topics in Quantum Electronics*, vol. 5, No. 4, Jul./Aug. 1999, pp. 1200-1204.
Yao, Gang et al., "Two-Dimensional Depth-Resolved Mueller Matrix Characterization of Biological Tissue by Optical Coherence Tomography," *Optics Letters*, Apr. 15, 1999, vol. 24, No. 8, pp. 537-539.
Lu, Shih-Yau et al., "Homogeneous and Inhomogeneous Jones Matrices," *J. Opt. Soc. Am. A.*, vol. 11, No. 2, Feb. 1994, pp. 766-773.
Bickel, S. William et al., "Stokes Vectors, Mueller Matrices, and Polarized Scattered Light," *Am. J. Phys.*, vol. 53, No. 5, May 1985 pp. 468-478.
Cameron, Brent D. et al., "Measurement and Calculation of the Two-Dimensional Backscattering Mueller Matrix of a Turbid Medium," *Optics Letters*, vol. 23, No. 7, Apr. 1, 1998, pp. 485-487.
De Boer, Johannes F. et al., "Two-Dimensional Birefringence Imaging in Biological Tissue by Polarization-Sensitive Optical Coherence Tomography," *Optics Letters*, vol. 22, No. 12, Jun. 15, 1997, pp. 934-936.
De Boer, Johannes F. et al., "Imaging Thermally Damaged Tissue by Polarization Sensitive Optical Coherence Tomography," *Optics Express*, vol. 3, No. 6, Sep. 14, 1998, pp. 212-218.
Hee, Michael R. et al., "Polarization-Sensitive Low-Coherence Reflectometer for Birefringence Characterization and Ranging," *J. Opt. Soc. Am. B.*, vol. 9, No. 6, Jun. 1992, pp. 903-908.
Barakat, Richard, "Statistics of the Stokes Parameters," *J. Opt. Soc. Am. B.*, vol. 4, No. 7, Jul. 1987, pp. 1256-1263.
Schmitt, J.M. et al., "Cross-Polarized Backscatter in Optical Coherence Tomography of Biological Tissue," *Optics Letters*, vol. 23, No. 13, Jul. 1, 1998, pp. 1060-1062.
Schoenenberger, Klaus et al., "Mapping of Birefringence and Thermal Damage in Tissue by use of Polarization-Sensitive Optical Coherence Tomography," *Applied Optics*, vol. 37, No. 25, Sep. 1, 1998, pp. 6026-6036.
Pierce, Mark C. et al., "Simultaneous Intensity, Birefringence, and Flow Measurements with High-Speed Fiber-Based Optical Coherence Tomography," *Optics Letters*, vol. 27, No. 17, Sep. 1, 2002, pp. 1534-1536
De Boer, Johannes F. et al., "Review of Polarization Sensitive Optical Coherence Tomography and Stokes Vector Determination," *Journal of Biomedical Optics*, Jul. 2002, vol. 7, No. 3, pp. 359-371.
Fried, Daniel et al., "Imaging Caries Lesions and Lesion Progression with Polarization Sensitive Optical Coherence Tomography," *Journal of Biomedical Optics*, vol. 7, No. 4, Oct. 2002, pp. 618-627.

Jiao, Shuliang et al., "Two-Dimensional Depth-Resolved Mueller Matrix of Biological Tissue Measured with Double-Beam Polarization-Sensitive Optical Coherence Tomography," *Optics Letters*, vol. 27, No. 2, Jan. 15, 2002, pp. 101-103.
Jiao, Shuliang et al., "Jones-Matrix Imaging of Biological Tissues with Quadruple-Channel Optical Coherence Tomography," *Journal of Biomedical Optics*, vol. 7, No. 3, Jul. 2002, pp. 350-358.
Kuranov, R.V. et al., "Complementary Use of Cross-Polarization and Standard OCT for Differential Diagnosis of Pathological Tissues," *Optics Express*, vol. 10, No. 15, Jul. 29, 2002, pp. 707-713.
Cense, Barry et al., "In Vivo Depth-Resolved Birefringence Measurements of the Human Retinal Nerve Fiber Layer by Polarization-Sensitive Optical Coherence Tomography," *Optics Letters*, vol. 27, No. 18, Sep. 15, 2002, pp. 1610-1612.
Ren, Hongwu et al., "Phase-Resolved Functional Optical Coherence Tomography: Simultaneous Imaging of In Situ Tissue Structure, Blood Flow Velocity, Standard Deviation, Birefringence, and Stokes Vectors in Human Skin," *Optics Letters*, vol. 27, No. 19, Oct. 1, 2002, pp. 1702-1704.
Tripathi, Renu et al., "Spectral Shaping for Non-Gaussian Source Spectra in Optical Coherence Tomography," *Optics Letters*, vol. 27, No. 6, Mar. 15, 2002, pp. 406-408.
Yasuno, Y. et al., "Birefringence Imaging of Human Skin by Polarization-Sensitive Spectral Interferometric Optical Coherence Tomography," *Optics Letters*, vol. 27, No. 20, Oct. 15, 2002 pp. 1803-1805.
White, Brian R. et al., "In Vivo Dynamic Human Retinal Blood Flow Imaging Using Ultra-High-Speed Spectral Domain Optical Doppler Tomography," *Optics Express*, vol. 11, No. 25, Dec. 15, 2003, pp. 3490-3497.
De Boer, Johannes F. et al., "Improved Signal-to-Noise Ratio in Spectral-Domain Compared with Time-Domain Optical Coherence Tomography," *Optics Letters*, vol. 28, No. 21, Nov. 1, 2003, pp. 2067-2069.
Jiao, Shuliang et al., "Optical-Fiber-Based Mueller Optical Coherence Tomography," *Optics Letters*, vol. 28, No. 14, Jul. 15, 2003, pp. 1206-1208.
Jiao, Shuliang et al., "Contrast Mechanisms in Polarization-Sensitive Mueller-Matrix Optical Coherence Tomography and Application in Burn Imaging," *Applied Optics*, vol. 42, No. 25, Sep. 1, 2003, pp. 5191-5197.
Moreau, Julien et al., "Full-Field Birefringence Imaging by Thermal-Light Polarization-Sensitive Optical Coherence Tomography. I. Theory," *Applied Optics*, vol. 42, No. 19, Jul. 1, 2003, pp. 3800-3810.
Moreau, Julien et al., "Full-Field Birefringence Imaging by Thermal-Light Polarization-Sensitive Optical Coherence Tomography. II. Instrument and Results," *Applied Optics*, vol. 42, No. 19, Jul. 1, 2003, pp. 3811-3818.
Morgan, Stephen P. et al., "Surface-Reflection Elimination in Polarization Imaging of Superficial Tissue," *Optics Letters*, vol. 28, No. 2, Jan. 15, 2003, pp. 114-116.
Oh, Jung-Taek et al., "Polarization-Sensitive Optical Coherence Tomography for Photoelasticity Testing of Glass/Epoxy Composites," *Optics Express*, vol. 11, No. 14, Jul. 14, 2003, pp. 1669-1676.
Park, B. Hyle et al., "Real-Time Multi-Functional Optical Coherence Tomography," *Optics Express*, vol. 11, No. 7, Apr. 7, 2003, pp. 782-793.
Shribak, Michael et al., "Techniques for Fast and Sensitive Measurements of Two-Dimensional Birefringence Distributions," *Applied Optics*, vol. 42, No. 16, Jun. 1, 2003, pp. 3009-3017.
Somervell, A.R.D. et al., "Direct Measurement of Fringe Amplitude and Phase Using a Heterodyne Interferometer Operating in Broadband Light," *Elsevier, Optics Communications*, Oct. 2003.
Stifter, D. et al., "Polarisation-Sensitive Optical Coherence Tomography for Material Characterisation and Strain-Field Mapping," Applied Physics A 76, Materials Science & Processing, Jan. 2003, pp. 947-951.
Davé, Digant P. et al., "Polarization-Maintaining Fiber-Based Optical Low-Coherence Reflectometer for Characterization and Ranging of Birefringence," *Optics Letters*, vol. 28, No. 19, Oct. 1, 2003, pp. 1775-1777.

(56) References Cited

OTHER PUBLICATIONS

Yang, Ying et al., "Observations of Birefringence in Tissues from Optic-Fibre-Based Optical Coherence Tomography," *Measurement Science and Technology*, Nov. 2002, pp. 41-46.
Yun, S.H. et al., "High-Speed Optical Frequency-Domain Imaging," *Optics Express*, vol. 11, No. 22, Nov. 3, 2003, pp. 2953-2963.
Yun, S.H. et al., "High-Speed Spectral-Domain Optical Coherence Tomography at 1.3 μm Wavelength," *Optics Express*, vol. 11, No. 26, Dec. 29, 2003, pp. 3598-3604.
Zhang, Jun et al., "Determination of Birefringence and Absolute Optic Axis Orientation Using Polarization-Sensitive Optical Coherence Tomography with PM Fibers," *Optics Express*, vol. 11, No. 24, Dec. 1, 2003, pp. 3262-3270.
Götzinger, Erich et al., "Measurement and Imaging of Birefringent Properties of the Human Cornea with Phase-Resolved, Polarization-Sensitive Optical Coherence Tomography," *Journal of Biomedical Optics*, vol. 9, No. 1, Jan./Feb. 2004, pp. 94-102.
Guo, Shuguang et al., "Depth-Resolved Birefringence and Differential Optical Axis Orientaion Measurements with Finer-based Polarization-Sensitive Optical Coherence Tomography," *Optics Letters*, vol. 29, No. 17, Sep. 1, 2004, pp. 2025-2027.
Huang, Xiang-Run et al.,"Variation of Peripapillary Retinal Nerve Fiber Layer Birefringence in Normal Human Subjects," *Investigative Ophthalmology & Visual Science*, vol. 45, No. 9, Sep. 2004, pp. 3073-3080.
Matcher, Stephen J. et al., "The Collagen Structure of Bovine Intervertebral Disc Studied Using Polarization-Sensitive Optical Coherence Tomography," *Physics in Medicine and Biology*, 2004, pp. 1295-1306.
Nassif, Nader et al., "In Vivo Human Retinal Imaging by Ultrahigh-Speed Spectral Domain Optical Coherence Tomography," *Optics Letters*, vol. 29, No. 5, Mar. 1, 2004, pp. 480-482.
Nassif, N.A. et al., "In Vivo High-Resolution Video-Rate Spectral-Domain Optical Coherence Tomography of the Human Retina and Optic Nerve," *Optics Express*, vol. 12, No. 3, Feb. 9, 2004, pp. 367-376.
Park, B. Hyle et al., "Comment on Optical-Fiber-Based Mueller Optical Coherence Tomography," *Optics Letters*, vol. 29, No. 24, Dec. 15, 2004, pp. 2873-2874.
Park, B. Hyle et al., "Jones Matrix Analysis for a Poliarization-Sensitive Optical Coherence Tomography System Using Fiber-Optic Components," *Optics Letters*, vol. 29, No. 21, Nov. 1, 2004, pp. 2512-2514.
Pierce, Mark C. et al., "Birefringence Measurements in Human Skin Using Polarization-Sensitive Optical Coherence Tomography," *Journal of Biomedical Optics*, vol. 9, No. 2, Mar./Apr. 2004, pp. 287-291.
Cense, Barry et al., "In Vivo Birefringence and Thickness Measurements of the Human Retinal Nerve Fiber Layer Using Polarization-Sensitive Optical Coherence Tomography," *Journal of Biomedical Optics*, vol. 9, No. 1, Jan./Feb. 2004, pp. 121-125.
Pircher, Michael et al., "Imaging of Polarization Properties of Human Retina in Vivo with Phase Resolved Transversal PS-OCT," *Optics Express*, vol. 12, No. 24, Nov. 29, 2004 pp. 5940-5951.
Pircher, Michael et al., "Transversal Phase Resolved Polarization Sensitive Optical Coherence Tomography," *Physics in Medicine & Biology*, 2004, pp. 1257-1263.
Srinivas, Shyam M. et al., "Determination of Burn Depth by Polarization-Sensitive Optical Coherence Tomography," *Journal of Biomedical Optics*, vol. 9, No. 1, Jan./Feb. 2004, pp. 207-212.
Strasswimmer, John et al., "Polarization-Sensitive Optical Coherence Tomography of Invasive Basal Cell Carcinoma," *Journal of Biomedical Optics*, vol. 9, No. 2, Mar./Apr. 2004, pp. 292-298.
Todorović, Miloš et al., "Determination of Local Polarization Properties of Biological Samples in the Presence of Diattenuation by use of Mueller Optical Coherence Tomography," *Optics Letters*, vol. 29, No. 20, Oct. 15, 2004, pp. 2402-2404.

Yasuno, Yoshiaki et al., "Polarization-Sensitive Complex Fourier Domain Optical Coherence Tomography for Jones Matrix Imaging of Biological Samples," Applied Physics Letters, vol. 85, No. 15, Oct. 11, 2004, pp. 3023-3025.
Erdelyi et al. "Generation of diffraction-free beams for applications in optical microlithography", J. Vac. Sci. Technol. B 15 (12), Mar./Apr. 1997, pp. 287-292.
Tearney et al., "Spectrally encoded miniature endoscopy" Optical Society of America; Optical Letters vol. 27, No. 6, Mar. 15, 2002; pp. 412-414.
Yelin et al., "Double-clad Fiber for Endoscopy" Optical Society of America; Optical Letters vol. 29, No. 20, Oct. 16, 2005; pp. 2408-2410.
PCT International Preliminary Report on Patentability for International Application No. PCT/US2004/038404 dated Jun. 2, 2006.
Office Action dated Aug. 24, 2006 for U.S. Appl. No. 10/137,749.
PCT International Search Report for Application No. PCT/US2006/018865 filed May 5, 2006.
International Written Opinion for International Patent application No. PCT/US2006/018865 filed May 5, 2006.
PCT International Search Report for Application No. PCT/US2006/016677 filed Apr. 28, 2006.
International Written Opinion for International Patent application No. PCT/US2006/016677 filed Apr. 28, 2006.
Office Action dated Nov. 13, 2006 for U.S. Appl. No. 10/501,268.
Office Action dated Nov. 20, 2006 for U.S. Appl. No. 09/709,162.
PCT International Search Report and Written Opinion for Application No. PCT/US2004/023585 filed Jul. 23, 2004.
Office Action dated Dec. 6, 2006 for U.S. Appl. No. 10/997,789.
Office Action dated Dec. 18, 2006 for U.S. Appl. No. 10/501,276.
PCT International Search Report and Written Opinion for Application No. PCT/US2007/060670 dated Sep. 21, 2007.
Office Action dated Oct. 11, 2007 for U.S. Appl. No. 11/534,095.
Office Action dated Oct. 9, 2007 for U.S. Appl. No. 09/709,162.
Notice of Allowance dated Oct. 3, 2007 for U.S. Appl. No. 11/225,840.
Office Action dated Oct. 30, 2007 for U.S. Appl. No. 11/670,069.
Tang C. L. et al., "Wide-band electro-optical tuning of semiconductor lasers", Applied Physics Letters, vol. 30, No. 2, Jan. 15, 1977, pp. 113-116.
Tang C. L. et al., "Transient effects in wavelength-modulated dye lasers", Applied Physics Letters, vol. 26, No. 9, May 1, 1975, pp. 534-537.
Telle M. John, et al., "Very rapid tuning of cw dye laser", Applied Physics Letters, vol. 26, No. 10, May 15, 1975, pp. 572-574.
Telle M. John, et al., "New method for electro-optical tuning of tunable lasers", Applied Physics Letters, vol. 24, No. 2, Jan. 15, 1974, pp. 85-87.
Schmitt M. Joseph et al. "OCT elastography: imaging microscopic deformation and strain of tissue", Optics Express, vol. 3, No. 6, Sep. 14, 1998, pp. 199-211.
M. Gualini Muddassir et al., "Recent Advancements of Optical Interferometry Applied to Medicine", IEEE Transactions on Medical Imaging, vol. 23, No. 2, Feb. 2004, pp. 205-212.
Maurice L. Roch et al. "Noninvasive Vascular Elastography: Theoretical Framework", IEEE Transactions on Medical Imaging, vol. 23, No. 2, Feb. 2004, pp. 164-180.
Lisauskas B. Jennifer et al., "Investigation of Plaque Biomechanics from Intravascular Ultrasound Images using Finite Element Modeling", Proceedings of the 19th International Conference—IEEE Oct. 30-Nov. 2, 1997, pp. 887-888.
Parker K. J. et al., "Techniques for Elastic Imaging: A Review", IEEE Engineering in Medicine and Biology, Nov./Dec. 1996, pp. 52-59.
Office Action dated Jan. 3, 2008 for U.S. Appl. No. 10/997,789.
Office Action dated Dec. 21, 2007 for U.S. Appl. No. 11/264,655.
Office Action dated Dec. 18, 2007 for U.S. Appl. No. 11/288,994.
Office Action dated Jan. 10, 2008 for U.S. Appl. No. 11/435,228.
Office Action dated Jan. 10, 2008 for U.S. Appl. No. 11/410,937.
Office Action dated Jan. 11, 2008 for U.S. Appl. No. 11/445,990.
Office Action dated Feb. 4, 2008 for U.S. Appl. No. 10/861,179.
PCT International Search Report and Written Opinion for Application No. PCT/US2007/061463 dated Jan. 23, 2008.

(56) References Cited

OTHER PUBLICATIONS

PCT International Search Report and Written Opinion for Application No. PCT/US2007/061481 dated Mar. 17, 2008.
PCT International Search Report and Written Opinion for Application No. PCT/US2007/078254 dated Mar. 28, 2008.
PCT International Search Report for Application No. PCT/US2007/068233 dated Feb. 21, 2008.
PCT International Search Report for Application No. PCT/US2007/060787 dated Mar. 18, 2008.
Statement under Article 19 and Reply to PCT Written Opinion for PCT International Application No. PCT/US2005/043951 dated Jun. 6, 2006.
PCT International Preliminary Report on Patentability for Application No. PCT/US2005/043951 dated Jun. 7, 2007.
Office Action dated Oct. 1, 2008 for U.S. Appl. No. 11/955,986.
Invitation of Pay Additional Fees dated Aug. 7, 2008 for International Application No. PCT/US2008/062354.
Invitation of Pay Additional Fees dated Jul. 20, 2008 for International Application No. PCT/US2007/081982.
International Search Report and Written Opinion dated Mar. 7, 2006 for PCT/US2005/035711.
International Search Report and Written Opinion dated Jul. 18, 2008 for PCT/US2008/057533.
Aizu, Y et al. (1991) "Bio-Speckle Phenomena and Their Application to the Evaluation of Blood Flow" Optics and Laser Technology, vol. 23, No. 4, Aug. 1, 1991.
Richards G.J. et al. (1997) "Laser Speckle Contrast Analysis (LASCA): A Technique for Measuring Capillary Blood Flow Using the First Order Statistics of Laser Speckle Patterns" Apr. 2, 1997.
Gonick, Maria M., et al (2002) "Visualization of Blood Microcirculation Parameters in Human Tissues by Time Integrated Dynamic Speckles Analysis" vol. 972, No. 1, Oct. 1, 2002.
International Search Report and Written Opinion dated Jul. 4, 2008 for PCT/US2008/051432.
Office Action dated Jun. 30, 2008 for U.S. Appl. No. 11/670,058.
Office Action dated Jul. 7, 2008 for U.S. Appl. No. 10/551,735.
Australian Examiner's Report dated May 27, 2008 for Australian patent application No. 2003210669.
Notice of Allowance dated Jun. 4, 2008 for U.S. Appl. No. 11/174,425.
European communication dated May 15, 2008 for European patent application No. 05819917.5.
International Search Report and Written Opinion dated Jun. 10, 2008 for PCT/US2008/051335.
Office Action dated Aug. 21, 2008 for U.S. Appl. No. 11/505,700.
Sticker, Markus (2002) En Face Imaging of Single Cell layers by Differential Phase-Contrast Optical Coherence Microscopy) *Optics Letters*, col. 27, No. 13, Jul. 1, 2002.
International Search Report and Written Opinion dated Jul. 17, 2008 for International Application No. PCT/US2008/057450.
International Search Report and Written Opinion dated Aug. 11, 2008 for International Application No. PCT/US2008/058703.
US National Library of Medicine (NLM), Bethesda, MD, US; Oct. 2007 (Oct. 2007), "Abstracts of the 19$^{th}$ Annual Symposium of Transcatheter Cardiovascular Therapeutics, Oct. 20-25, 2007, Washington, DC, USA."
International Search Report and Written Opinion dated May 26, 2008 for International Application No. PCT/US2008/051404.
Office Action dated Aug. 25, 2008 for U.S. Appl. No. 11/264,655.
Office Action dated Sep. 11, 2008 for U.S. Appl. No. 11/624,334.
Office Action dated Aug. 21, 2008 for U.S. Appl. No. 11/956,079.
Gelikono, V. M. et al. Oct. 1, 2004 "Two-Wavelength Optical Coherence Tomography" Radio physics and Quantum Electronics, Kluwer Academic Publishers—Consultants. vol. 47, No. 10-1.
International Search Report and Written Opinion for PCT/US2007/081982 dated Oct. 19, 2007.
Database Compendex Engineering Information, Inc., New York, NY, US; Mar. 5, 2007, Yelin, Dvir et al: "Spectral-Domain Spectrally-Encoded Endoscopy".
Database Biosis Biosciences Information Service, Philadelphia, PA, US; Oct. 2006, Yelin D. et al: "Three-Dimensional Miniature Endoscopy".
International Search Report and Written Opinion dated Mar. 14, 2005 for PCT/US2004/018045.
Notification of the international Preliminary Report on Patentability dated Oct. 21, 2005.
Shim M.G. et al., "Study of Fiber-Optic Probes For In vivo Medical Raman Spectroscopy" Applied Spectroscopy. vol. 53, No. 6, Jun. 1999.
Bingid U. et al., "Fibre-Optic Laser-Assisted Infrared Tumour Diagnostics (FLAIR); Infrared Tomour Diagnostics" Journal of Physics D. Applied Physics, vol. 38, No. 15, Aug. 7, 2005.
Jun Zhang et al. "Full Range Polarization-Sensitive Fourier Domain Optical Coherence Tomography" Optics Express, vol. 12, No. 24. Nov. 29, 2004.
Yonghua et al., "Real-Time Phase-Resolved Functional Optical Hilbert Transformation" Optics Letters, vol. 27, No. 2, Jan. 15, 2002.
Siavash et al., "Self-Referenced Doppler Optical Coherence Tomography" Optics Letters, vol. 27, No. 23, Dec. 1, 2002.
International Search Report and Written Opinion dated Dec. 20, 2004 for PCT/US04/10152.
Notification Concerning Transmittal of International Preliminary Report on Patentability dated Oct. 13, 2005 for PCT/US04/10152.
International Search Report and Written Opinion dated Mar. 23, 2006 for PCT/US2005/042408.
International Preliminary Report on Patentability dated Jun. 7, 2007 for PCT/US2005/042408.
International Search Report and Written Opinion dated Feb. 28, 2007 for International Application No. PCT/US2006/038277.
International Search Report and Written Opinion dated Jan. 30, 2009 for International Application No. PCT/US2008/081834.
Fox, J.A. et al; "A New Galvanometric Scanner for Rapid tuning of C02 Lasers" New York, IEEE, US vol. Apr. 7, 1991.
Motaghian Nezam, S.M. et al: "High-speed Wavelength-Swept Semiconductor laser using a Diffraction Grating and a Polygon Scanner in Littro Configuration" *Optical Fiber Communication and the National Fiber Optic Engineers Conference* Mar. 29, 2007.
International Search Report and Written Opinion dated Feb. 2, 2009 for International Application No. PCT/US2008/071786.
Bilenca A et al: "The Role of Amplitude and phase in Fluorescence Coherence Imaging: From Wide Filed to Nanometer Depth Profiling", *Optics IEEE*, May 5, 2007.
Inoue, Yusuke et al: "Varible Phase-Contrast Fluorescence Spectrometry for Fluorescently Strained Cells", *Applied Physics Letters*, Sep. 18, 2006.
Bernet, S et al: "Quantitative Imaging of Complex Samples by Spiral Phase Contrast Microscopy", *Optics Express*, May 9, 2006.
International Search Report and Written Opinion dated Jan. 15, 2009 for International Application No. PCT/US2008/074863.
Office Action dated Feb. 17, 2009 for U.S. Appl. No. 11/211,483.
Notice of Reasons for Rejection dated Dec. 2, 2008 for Japanese patent application No. 2000-533782.
International Search Report and Written Opinion dated Feb. 24, 2009 for PCT/US2008/076447.
European Official Action dated Dec. 2, 2008 for EP 07718117.0.
International Search Report and Written Opinion dated Jun. 10, 2009 for PCT/US08/075456.
European Search Report dated May 5, 2009 for European Application No. 01991471.2.
Motz, J.T. et al: "Spectral-and Frequency-Encoded Fluorescence Imaging" Optics Letters, OSA, Optical Society of America, Washington, DC, US, vol. 30, No. 20, Oct. 15, 2005, pp. 2760-2762.
Japanese Notice of Reasons for Rejection dated Jul. 14, 2009 for Japanese Patent application No. 2006-503161.
Office Action dated Aug. 18, 2009 for U.S. Appl. No. 12/277,178.
Office Action dated Aug. 13, 2009 for U.S. Appl. No. 10/136,813.
Office Action dated Aug. 6, 2009 for U.S. Appl. No. 11/624,455.
Office Action dated May 15, 2009 for U.S. Appl. No. 11/537,123.
Office Action dated Apr. 17, 2009 for U.S. Appl. No. 11/537,343.
Office Action dated Apr. 15, 2009 for U.S. Appl. No. 12/205,775.
Office Action dated Dec. 9, 2008 for U.S. Appl. No. 09/709,162.

(56) References Cited

OTHER PUBLICATIONS

Office Action dated Dec. 23, 2008 for U.S. Appl. No. 11/780,261.
Office Action dated Jan. 9, 2010 for U.S. Appl. No. 11/624,455.
Office Action dated Feb. 18, 2009 for U.S. Appl. No. 11/285,301.
Beddow et al, (May 2002) "Improved Performance Interferomater Designs for Optical Coherence Tomography", IEEE Optical Fiber Sensors Conference, pp. 527-530.
Yaqoob et al., (Jun. 2002) "High-Speed Wavelength-Multiplexed Fiber-Optic Sensors for Biomedicine," Sensors Proceedings of the IEEE, pp. 325-330.
Office Action dated Feb. 18, 2009 for U.S. Appl. No. 11/697,012.
Zhang et al, (Sep. 2004), "Fourier Domain Functional Optical Coherence Tomography", Saratov Fall Meeting 2004, pp. 8-14.
Office Action dated Feb. 23, 2009 for U.S. Appl. No. 11/956,129.
Office Action dated Mar. 16, 2009 for U.S. Appl. No. 11/621,694.
Office Action dated Oct. 1, 2009 for U.S. Appl. No. 11/677,278.
Office Action dated Oct. 6, 2009 for U.S. Appl. No. 12/015,642.
Summons to attend Oral Proceedings dated Oct. 9, 2009 for European patent application No. 06813365.1.
Office Action dated Dec. 15, 2009 for U.S. Appl. No. 11/549,397.
Hariri, Lida P. et al. "Endoscopic Optical Coherence Tomography and Laser-Induced Fluorescence Spectroscopy in a Murine Colon Cancer Model", Laser in Surgery and Medicine, vol. 38, 2006, pp. 305-313.
PCT International Search Report and Written Opinion for Application No. PCT/US2006/031905 dated May 3, 2007.
PCT International Search Report and Written Opinion for Application No. PCT/US2007/060481 dated May 23, 2007.
PCT International Search Report and Written Opinion for Application No. PCT/US2007/060717 dated May 24, 2007.
PCT International Search Report and Written Opinion for Application No. PCT/US2007/060319 dated Jun. 6, 2007.
D. Yelin et al., "Three-dimensional imaging using spectral encoding heterodyne interferometry", Optics Letters, Jul. 15, 2005, vol. 30, No. 14, pp. 1794-1796.
Akiba, Masahiro et al. "En-face optical coherence imaging for three-dimensional microscopy", SPIE, 2002, pp. 8-15.
Office Action dated Aug. 10, 2007 for U.S. Appl. No. 10/997,789.
Office Action dated Feb. 2, 2007 for U.S. Appl. No. 11/174,425.
PCT International Search Report and Written Opinion for Application No. PCT/US2007/060657 dated Aug. 13, 2007.
Lewis, Neil E. et al., "Applications of Fourier Transform Infrared Imaging Microscopy in Neurotoxicity", Annals New York Academy of Sciences, pp. 234-246.
Joo, Chulmin et al., Spectral-domain optical coherence phase microscopy for quantitative phase-contrast imaging, Optics Letters, Aug. 15, 2005, vol. 30, No. 16, pp. 2131-2133.
Guo, Bujin et al., "Laser-based mid-infrared reflectance imaging of biological tissues", Optics Express, Jan. 12, 2004, vol. 12, No. 1, pp. 208-219.
Office Action dated Mar. 28, 2007 for U.S. Appl. No. 11/241,907.
Office Action dated May 23, 2007 for U.S. Appl. No. 10/406,751.
Office Action dated May 23, 2007 for U.S. Appl. No. 10/551,735.
PCT International Search Report and Written Opinion for Application No. PCT/US2007/061815 dated Aug. 2, 2007.
Sir Randall, John et al., "Brillouin scattering in systems of biological significance", Phil. Trans. R. Soc. Lond. A 293, 1979, pp. 341-348.
Takagi, Yasunari, "Application of a microscope to Brillouin scattering spectroscopy", Review of Scientific Instruments, No. 12, Dec. 1992, pp. 5552-5555.
Lees, S. et al., "Studies of Compact Hard Tissues and Collagen by Means of Brillouin Light Scattering", Connective Tissue Research, 1990, vol. 24, pp. 187-205.
Berovic, N. "Observation of Brillion scattering from single muscle fibers", European Biophysics Journal, 1989, vol. 17, pp. 69-74.
PCT International Search Report and Written Opinion for Application No. PCT/US2007/062465 dated Aug. 8, 2007.
Pyhtila John W. et al., "Rapid, depth-resolved light scattering measurements using Fourier domain, angle-resolved low coherence interferometry", Optics Society of America, 2004.
Pyhtila John W. et al., "Determining nuclear morphology using an improved angle-resolved low coherence interferometry system", Optics Express, Dec. 15, 2003, vol. 11, No. 25, pp. 3473-3484.
Desjardins A.E., et al., "Speckle reduction in OCT using massively-parallel detection and frequency-domain ranging", Optics Express, May 15, 2006, vol. 14, No. 11, pp. 4736-4745.
Nadkarni, Seemantini K., et al., "Measurement of fibrous cap thickness in atherosclerotic plaques by spatiotemporal analysis of laser speckle images", Journal of Biomedical Optics, vol. 11 Mar./Apr. 2006, pp. 021006-1-021006-8.
PCT International Search Report and Written Opinion for Application No. PCT/US2007/066017 dated Aug. 30, 2007.
Yamanari M. et al., "Polarization sensitive Fourier domain optical coherence tomography with continuous polarization modulation", Proc. of SPIE, vol. 6079, 2006.
Zhang Jun et al., "Full range polarization-sensitive Fourier domain optical coherence tomography", Optics Express, Nov. 29, 2004, vol. 12, No. 24, pp. 6033-6039.
European Patent Office Search report for Application No. 01991092.6-2305 dated Jan. 12, 2006.
The Third Office Action for Japanese Patent Application 2011-276472 dated Jan. 13, 2015.
The Fourth Office Action for Chinese Patent Application 200780009476.X dated Nov. 4, 2014.
The Third Office Action for European Patent Application 07845211.7 dated Oct. 22, 2014.
Poneros er al: "Optical Coherence Tomography of the Biliary Tree During ERCP", Gastrointestinal Endoscopy, Elsevier, NL, vol. 55, No. 1, Jan. 1, 2002, pp. 84-88.
Fu L e tal: Double-Clad Photonic Crystal Fiber Coupler for compact Nonlinear Optical Microscopy Imaging, Optics Letters, OSA, Optical Society of America, vol. 31, No. 10, May 15, 2006, pp. 1471-1473.
Japanese language Appeal Decision dated Jan. 10, 2012 for JP 2006-503161.
Japanese Notice of Grounds for Rejection dated Oct. 28, 2011 for JP2009-294737.
Japanese Notice of Grounds for Rejection dated Dec. 28, 2011 for JP2008-535793.
Japanese Notice of Reasons for Rejection dated Dec. 12, 2011 for JP 2008-533712.
International Search Report and Written Opinion dated Feb. 9, 2012 based on PCT/US2011/034810.
Japanese Notice of Reasons for Rejection dated Mar. 27, 2012 for JP 2003-102672.
Japanese Notice of Reasons for Rejection dated May 8, 2012 for JP 2008-533727.
Korean Office Action dated May 25, 2012 for KR 10-2007-7008116.
Japanese Notice of Reasons for Rejection dated May 21, 2012 for JP 2008-551523.
Japanese Notice of Reasons for Rejection dated Jun. 20, 2012 for JP 2009-546534.
European Official Communication dated Aug. 1, 2012 for EP 10193526.0.
Copy of European Search Report dated Jun. 25, 2012 for EP 10733985.5.
Wieser, Wolfgang et al., "Multi-Megahertz OCT: High Quality 3D Imaging at 20 million A-Scans and 4.5 Gvoxels Per Second" Jul. 5, 2010, vol. 18, No. 14, Optics Express.
European Communication Pursuant to EPC Article 94(3) for EP 07843206.7 dated Aug. 30, 2012.
International Search Report and Written Opinion dated Aug. 30, 2012 for PCT/US2012/035234.
Giuliano, Scarcelli et al., "Three-Dimensional Brillouin Confocal Microscopy". Optical Society of American, 2007, CtuV5.
Giuliano, Scarcelli et al., "Confocal Brillouin Microscopy for Three-Dimensional Mechanical Imaging." Nat Photonis, Dec. 9, 2007.

(56) References Cited

OTHER PUBLICATIONS

Japanese Notice of Reasons or Rejections dated Oct. 10, 2012 for 2008-553511.
W.Y. Oh et al: "High-Speek Polarization Sensitive Optical Frequency Domain Imaging with Frequency Multiplexing ", Optics Express, vol. 16, No. 2, Jan. 1, 2008.
Athey, B.D. el al., "Development and Demonstration of a Networked Telepathology 3-D Imaging, Databasing, and Communication System", 1998 ("C2"), pp. 5-17.
D'Amico, A.V., et al., "Optical Coherence Tomography as a Method for Identifying Benign and Maliganat Microscopic Structures in the Prostate Gland", Urology, vol. 55, Isue 5, May 2000 ("C3"), pp. 783-787.
Tearney, G.J. et al., "In Vivo Endoscopic Optical Biopsy with Optical Coherence Tomography", Science, vol. 276, No. 5321, Jun. 27, 1997 ("C6"), pp. 2307-2309.
Japanese Notice of Reasons for Rejections dated Oct. 2, 2012 for 2007-543626.
Canadian Office Action dated Oct. 10, 2012 for 2,514,189.
Japanese Notice of Reasons for Rejections dated Nov. 9, 2012 for JP 2007-530134.
Japanese Notice of Reasons for Rejections dated Nov. 27, 2012 for JP 2009-554772.
Japanese Notice of Reasons for Rejections dated Oct. 11, 2012 for JP 2008-533712.
Yoden, K. et al. "An Approach to Optical Reflection Tomography Along the Geometrial Thickness," Optical Review, vol. 7, No. 5, Oct. 1, 2000.
International Search Report and Written Opinion dated Oct. 25, 2012 for PCT/US2012/047415.
Joshua, Fox et al: "Measuring Primate RNFL Thickness with OCT", IEEE Journal of Selected Topics in Quantum Electronics, IEEE Service Center, Piscataway, NJ, US, vol. 7,No. 6, Nov. 1, 2001.
European Official Communication dated Feb. 6, 2013 for 04822169.1.
International Search Report dated Jan. 31, 2013 for PCT/US2012/061135.
Viliyam K. Pratt, Lazernye Sistemy Svyazi, Moskva, Izdatelstvo "Svyaz", 1972. p. 68-70.
International Search Report and Written Opinion dated Jan. 31, 2013 for PCT/US2012/060843.
European Search Report dated Mar. 11, 2013 doe EP 10739129.4.
Huber, R et al: "Fourier Domain Mode Locked Lasers for OCT Imaging at up to 290 kHz Sweep Rates", Proceedings of SPIE, SPIE—International Society for Optical Engineering, US, vol. 5861, No. 1, Jan. 1, 2005.
M. Kourogi et al: "Programmable High Speed (1MHz) Vernier-mode-locked Frequency-Swept Laser for OCT Imaging", Proceedings of SPIE, vol. 6847, Feb. 7, 2008.
Notice of Reasons for Rejection dated Feb. 5, 2013 for JP 2008-509233.
Notice of Reasons for Rejection dated Feb. 19, 2013 for JP 2008-507983.
European Extended Search Report dated Mar. 26, 2013 for EP 09825421.1.
Masahiro, Yamanari et al: "polarization-Sensitive Swept-Source Optical Coherence Tomography with Continuous Source Polarization Modulation", Optics Express, vol. 16, No. 8, Apr. 14, 2008.
European Extended Search Report dated Feb. 1, 2013 for EP 12171521.3.
Nakamura, Koichiro et al., "A New Technique of Optical Ranging by a Frequency-Shifted Feedback Laser", IEEE Phontonics Technology Letters, vol. 10, No. 12, pp. 1041-1135, Dec. 1998.
Lee, Seok-Jeong et al., "Ultrahigh Scanning Speed Optical Coherence Tomography Using Optical Frequency Comb Generators", The Japan Soceity of Applied Physics, vol. 40 (2001).
Kinoshita, Masaya et al., "Optical Frequency-Domain Imaging Microprofilmetry with a Frequency-Tunable Liquid-Crystal Fbry-Perot Etalon Device" Applied Optics, vol. 38, No. 34, Dec. 1, 1999.

Notice of Reasons for Rejection dated Apr. 16, 2013 for JP 2009-510092.
Bachmann A.H. et al: "Heterodyne Fourier Domain Optical Coherence Tomography for Full Range Probing with High Axial Resolution", Optics Express, OSA, vol. 14, No. 4, Feb. 20, 2006.
European Search Report for 12194876.4 dated Feb. 1, 2013.
International Search Report and Written Opinion for PCT/US2013/022136.
Thomas J. Flotte: "Pathology Correlations with Optical Biopsy Techniques", Annals of the New York Academy of Sciences, Wiley-Blackwell Publishing, Inc. SU, vol. 838, No. 1, Feb. 1, 1998, pp. 143-149.
Constance R. Chu et al: Arthroscopic Microscopy of Articular Cartilage Using Optical Coherence Tomography, American Journal of Sports Medicine, American Orthopedic Society for Sports Medicine, Waltham, MA, Vo. 32, No. 9, Apr. 1, 2004.
Bouma B E et al: Diagnosis of Specialized Intestinal Metaplasia of the Esophagus with Optical Coherence Tomography, Conference on Lasers and Electro-Optics. Technical Digest, OSA, US, vol. 56, May 6, 2001.
Shen et al: "Ex Vivo Histology-Correlated Optical Coherence Tomography in the Detection of Transmural Inflammation in Crohn's Disease", Clinical Gastroenterology and Heptalogy, vol. 2, No. 9, Sep. 1, 2004.
Shen et al: "In Vivo Colonscopic Optical Coherence Tomography for Transmural Inflammation in Inflammatory Bowel Disease", Clinical Gastroenterology and Hepatology, American Gastroenterological Association, US, vol. 2, No. 12, Dec. 1, 2004.
Ge Z et al: "Identification of Colonic Dysplasia and Neoplasia by Diffuse Reflectance Spectroscopy and Pattern Recognition Techniques", Applied Spectroscopy, The Society for Applied Spectroscopy, vol. 52, No. 6, Jun. 1, 1998.
Elena Zagaynova et al: "Optical Coherence Tomography: Potentialities in Clinical Practice", Proceedings of SPIE, Aug. 20, 2004.
Westphal et al: "Correlation of Endoscopic Optical Coherence Tomography with Histology in the Lower-GI Tract", Gastrointestinal Endoscopy, Elsevier, NL, vol. 61, No. 4, Apr. 1, 2005.
Haggitt et al: "Barrett's Esophaagus, Dysplasia, and Adenocarcinoma", Human Pathology, Saunders, Philadelphia, PA, US; vol. 25, No. 10, Oct. 1, 1994.
Gang Yao et al. "Monte Carlo Simulation of an Optical Coherence Tomography Signal in Homogenous Turbid Media," Physics in Medicine and Biology, 1999.
Murakami, K. "A Miniature Confocal Optical Scanning Microscopy for Endscopes", Proceedings of SPIE, vol. 5721, Feb. 28, 2005, pp. 119-131.
Seok, H. Yun et al: "Comprehensive Volumetric Optical Microscopy in Vivo", Nature Medicine, vol. 12, No. 12, Jan. 1, 2007.
Baxter: "Image Zooming", Jan. 25, 2005, Retrieved from the Internet.
Qiang Zhou et al: "A Novel Machine Vision Application for Analysis and Visualization of Confocal Microscopic Images" Machine Vision and Applications, vol. 16, No. 2, Feb. 1, 2005.
Igor Gurov et al: (2007) "Full-field High-Speed Optical Coherence Tomography System for Evaluting Multilayer and Random Tissues", Proc. of SPIE, vol. 6618.
Igor Gurov et al: "High-Speed Signal Evaluation in Optical Coherence Tomography Based on Sub-Nyquist Sampling and Kalman Filtering Method" AIP Coherence Proceedings, vol. 860, Jan. 1, 2006.
Groot De P et al: "Three Dimensional Imaging by Sub-Nyquist Sampling of White-Light Interferograms", Optics Letters, vol. 18, No. 17, Sep. 1, 1993.
Silva et al: "Extended Range, Rapid Scanning Optical Delay Line for Biomedial Interferometric Imaging", Electronics Letter, IEE Stevenage, GB vol. 35, No. 17, Aug. 19, 1999.
Notice of Reasons for Rejection dated Dec. 4, 2012 for Japanese Patent Application No. 2008-553509.
Notice of Reasons for Rejection dated Oct. 22, 2013 for Japanese Patent Application No. 2008-553509.
Notice of Reasons for Rejection dated Feb. 21, 2012 for Japanese Patent Application No. 2008-553509.

(56) References Cited

OTHER PUBLICATIONS

Notification of the First Office Action dated May 12, 2010 for Chinese Patent Application No. 200780010692.6.
Notification of the Second Office Action dated Jun. 29, 2011 for Chinese Patent Application No. 200780010692.6.
Notification of the Third Office Action dated May 3, 2012 for Chinese Patent Application No. 200780010692.6.
Notification of the Fourth Office Action dated Dec. 3, 2012 for Chinese Patent Application No. 200780010692.6.
Notification of the Fifth Office Action dated Jul. 3, 2013 for Chinese Patent Application No. 200780010692.6.
Communication pursuant to Article 94(3) EPC dated Aug. 30, 2012 for European Patent Application No. 07845206.7.
Communication pursuant to Article 94(3) EPC dated Septmeber 18, 2013 for European Patent Application No. 07845206.7.
Communication pursuant to Article 94(3) EPC dated Sep. 13, 2010 for European Patent Application No. 07845206.7.
Summons to attend oral proceedings pursuant to Rule 115(1) EPC dated Mar. 25, 2015 for European Patent Application No. 07845206.7.
R. Haggitt et al., "Barrett's Esophagus Correlation Between Mucin Histochemistry, Flow Cytometry, and Histological Diagnosis for Predicting Increased Cancer Risk," Apr. 1988, American Journal of Pathology, vol. 131, No. 1, pp. 53-61.
R.H. Hardwick et al., (1995) "c-erbB-2 Overexpression in the Dysplasia/Carcinoma Sequence of Barrett's Oesophagus," Journal of Clinical Pathology, vol. 48, No. 2, pp. 129-132.
W. Polkowski et al, (1998) Clinical Decision making in Barrett's Oesophagus can be supported by Computerized Immunoquantitation and Morphometry of Features Associated with Proliferation and Differentiation, Journal of pathology, vol. 184, pp. 161-168.
J.R. Turner et al., MN Antigen Expression in Normal Preneoplastic, and Neoplastic Esophagus: A Clinicopathological Study of a New Cancer-Associated Biomarker,: Jun. 1997, Human Pathology, vol. 28, No. 6, pp. 740-744.
D.J. Bowery et al., (1999) "Patterns of Gastritis in Patients with Gastro-Oesophageal Reflux Disease,", Gut, vol. 45, pp. 798-803.
O'Reich et al., (2000) "Expression of Oestrogen and Progesterone Receptors in Low-Grade Endometrial Stromal Sarcomas,", British Journal of Cancer, vol. 82, No. 5, pp. 1030-1034.
M.I. Canto et al., (1999) "Vital Staining and Barrett's Esophagus," Gastrointestinal Endoscopy, vol. 49, No. 3, Part 2, pp. SI2-S16.
S. Jackle et al., (2000) "In Vivo Endoscopic Optical Coherence Tomography of the Human Gastrointestinal Tract-Toward Optical Biopsy," Encoscopy, vol. 32, No. 10, pp. 743-749.
E. Montgomery et al., "Reproducibility of the Diagnosis of Dysplasia in Barrett Esophagus: A Reaffirmation," Apr. 2001, Human Pathology, vol. 32, No. 4, pp. 368-378.
H. Geddert et al., "Expression Cyclin B1 in the Metaplasia-Dysphasia-Carcinoma Sequence of Barrett Esophagus," Jan. 2002, Cancer, vol. 94, No. 1, pp. 212-218.
P. Pfau et al., (2003) "Criteria for the Diagnosis of Dysphasia by Endoscopic Optical Coherence Tomography," Gastrointestinal Endoscopy, vol. 58, No. 2, pp. 196-2002.
R. Kiesslich et al., (2004) "Confocal Laser Endoscopy for Diagnosing Intraepithelial Neoplasias and Colorectal Cancer in Vivo," Gastroenterology, vol. 127, No. 3, pp. 706-713.
X. Qi et al., (2004) "Computer Aided Diagnosis of Dysphasia in Barrett's Esophagus Using Endoscopic Optical Conherence Tomography," SPIE, Coherence Domain Optical Methods and Optical Coherence Tomography in Biomedicine VIII. Proc. of Conference on., vol. 5316, pp. 33-40.
Seltzer et al., (1991) "160 nm Continuous Tuning of a MQW Laser in an External Cavity Across the Entire 1.3 μm Communications Window," Electronics Letters, vol. 27, pp. 95-96.
Office Action dated Jan. 25, 2010 for U.S. Appl. No. 11/537,048.
International Search Report dated Jan. 27, 2010 for PCT/US2009/050553.
International Search Report dated Jan. 27, 2010 for PCT/US2009/047988.
International Search Report dated Feb. 23, 2010 for U.S. App. No. 11/445,131.
Office Action dated Mar. 18, 2010 of U.S. Appl. No. 11/844,454.
Office Action dated Apr. 8, 2010 of U.S. Appl. No. 11/414,564.
Japanese Office Action dated Apr. 13, 2010 for Japanese Patent application No. 2007-515029.
International Search Report dated May 27, 2010 for PCT/US2009/063420.
Office Action dated May 28, 2010 for U.S. Appl. No. 12/015,642.
Office Action dated Jun. 2, 2010 for U.S. Appl. No. 12/112,205.
Office Action dated Jul. 7, 2010 for U.S. Appl. No. 11/624,277.
Montag Ethan D., "Parts of the Eye" online textbook for JIMG 774: Vision & Psycophysics, download on Jun. 23, 2010 from http://www.cis.rit.edu/people/faculty/montag/vandplite/pages/chap_8/ch8p3.html.
Office Action dated Jul. 16, 2010 for U.S. Appl. No. 11/445,990.
Office Action dated Jul. 20, 2010 for U.S. Appl. No. 11/625,135.
Office Action dated Aug. 5, 2010 for U.S. Appl. No. 11/623,852.
Chinese office action dated Aug. 4, 2010 for CN 200780005949.9.
Chinese office action dated Aug. 4, 2010 for CN 200780016266.3.
Zhang et al., "Full Range Polarization-Sensitive Fourier Domain Optical Coherence Tomography" Optics Express, Nov. 29, 2004, vol. 12, No. 24.
Office Action dated Aug. 27, 2010 for U.S. Appl. No. 11/569,790.
Office Action dated Aug. 31, 2010 for U.S. Appl. No. 11/677,278.
Office Action dated Sep. 3, 2010 for U.S. Appl. No. 12/139,314.
Yong Zhao et al: "Virtual Data Grid Middleware Services for Data-Intensive Science", Concurrency and Computation: Practice and Experience, Wiley, London, GB, Jan. 1, 2000, pp. 1-7, pp. 1532-0626.
Swan et al., "Toward Nanometer-Scale Resolution in Fluorescence Microscopy using Spectral Self-Inteference" IEEE Journal. Selected Topics in Quantum Electronics 9 (2) 2003, pp. 294-300.
Moiseev et al., "Spectral Self-Interference Fluorescence Microscopy", J. Appl. Phys. 96 (9) 2004, pp. 5311-5315.
Hendrik Verschueren, "Interference Reflection Microscopy in Cell Biology", J. Cell Sci. 75, 1985, pp. 289-301.
Park et al., "Diffraction Phase and Fluorescence Microscopy", Opt. Expr. 14 (18) 2006, pp. 8263-8268.
Swan et al., "High Resolution Spectral Self-Interference Fluorescence Microscopy", Proc. SPIE 4621, 2002, pp. 77-85.
Sanchez et al., "Near-Field Fluorscence Microscopy Based on Two-Photon Excvitation withMetal Tips", Phys. Rev. Lett. 82 (20) 1999, pp. 4014-4017.
Wojtkowski, Maciej, Ph.D. "Three-Dimensional Retinal Imaging with High-Speed Ultrahigh-Resolution Optical Coherence Tomography" Ophthalmology, Oct. 2005, 112(10): 1734-1746.
Vaughan, J.M. et al., "Brillouin Scattering, Density and Elastic Properties of the Lens and Cornea of the Eye", Nature, vol. 284, Apr. 3, 1980, pp. 489-491.
Hess, S.T. et al. "Ultra-high Resolution Imaging by Fluorescence Photoactivation Localization Microscopy" Biophysical Journal vol. 91, Dec. 2006, 4258-4272.
Fernandez-Suarez, M. et al., "Fluorescent Probes for Super-Resolution Imaging in Living Cells" Nature Reviews Molecular Cell Biology vol. 9, Dec. 2008.
Extended European Search Report dated Dec. 14, 2010 for EP 10182301.1.
S. Hell et al., "Breaking the diffraction resolution limit by stimulated-emission—stimulated-emission-depletion fluorescence microscopy," Optics Letters. 19:495 (1995) and Ground State Depletion (GSD).
S. Hell et al. "Ground-State-Depletion fluorescence microscopy—a concept for breaking the diffraction resolution limit," Applied Physics B. 60:780 (1994)) fluorescence microscopy, photo-activated localization microscopy (PALM).
E. Betzig et al. "Imaging intracellular fluorescent proteins at nanometer resolution," Science 313:1642 (2006), stochastic optical reconstruction microscopy (STORM).
M. Rust et al. "Sub-diffraction-limited imaging by stochastic optical reconstruction microscopy (STORM)," Nature Methods 3:783 (2006), and structured illumination microscopy (SIM).

(56) References Cited

OTHER PUBLICATIONS

B. Bailey et al. "Enhancement of Axial Resolution in Fluorescence Microscopy by Standing-Wave Excitation," Nature 366:44 (1993).
M. Gustafsson "Surpassing the lateral resolution limit by a factor of two using structured illumination microscopy," Journal of Microscopy 198:82 (2000).
M. Gustafsson "Nonlinear structured illumination microscopy: Widefield fluorescence imaging with theoretically unlimited resolution," PNAS 102:13081 (2005)).
R. Thompson et al. "Precise nanometer localization analysis for individual fluorescent probes," Biophysical Journal 82:2775 (2002).
K. Drabe et al. "Localization of Spontaneous Emission in front of a mirror," Optics Communications 73:91 (1989).
Swan et al. "Toward nanometer-scale resolution in fluorescence microscopy using spectral self-interference," IEEE Quantum Electronics 9:294 (2003).
C. Joo, et al. "Spectral Domain optical coherence phase and multiphoton microscopy," Optics Letters 32:623 (2007).
Virmani et al., "Lesions from sudden coronary death: A comprehensive morphological classification scheme for atherosclerotic lesions," Arterioscler. Thromb. Vase. Bio., 20:1262-75 (2000).
Gonzalez, R.C. and Wintz, P., "Digital Image Processing" Addison-Wesley Publishing Company, Reading MA, 1987.
V. Tuchin et al., "Speckle interferometry in the measurements ofbiotissues vibrations," SPIE, 1647: 125 (1992).
A.A. Bednov et al., "Investigation of Statistical Properties of Lymph Flow Dynamics Using Speckle-Microscopy," SPIE, 2981: 181-90 (1997).
Feng et al., "Mesocopic Conductors and Correlations in Laser Speckle Patters" Science, New Series, vol. 251, No. 4994, pp. 633-639 (Feb. 8, 1991).
Lee et al., "The Unstable Atheroma," Arteriosclerosis, Thrombosis & Vascular Biology, 17:1859-67 (1997).
International Search report dated Apr. 29, 2011 for PCT/US2010/051715.
International Search report dated Sep. 13, 2010 for PCT/US2010/023215.
International Search Report dated Jul. 28, 2011 for PCT/US2010/059534.
International Search report dated Nov. 18, 2011 for PCT/US2011/027450.
International Search report dated Nov. 18, 2011 for PCT/US2011/027437.
International Search report dated Nov. 22, 2011 for PCT/US2011/027421.

\* cited by examiner

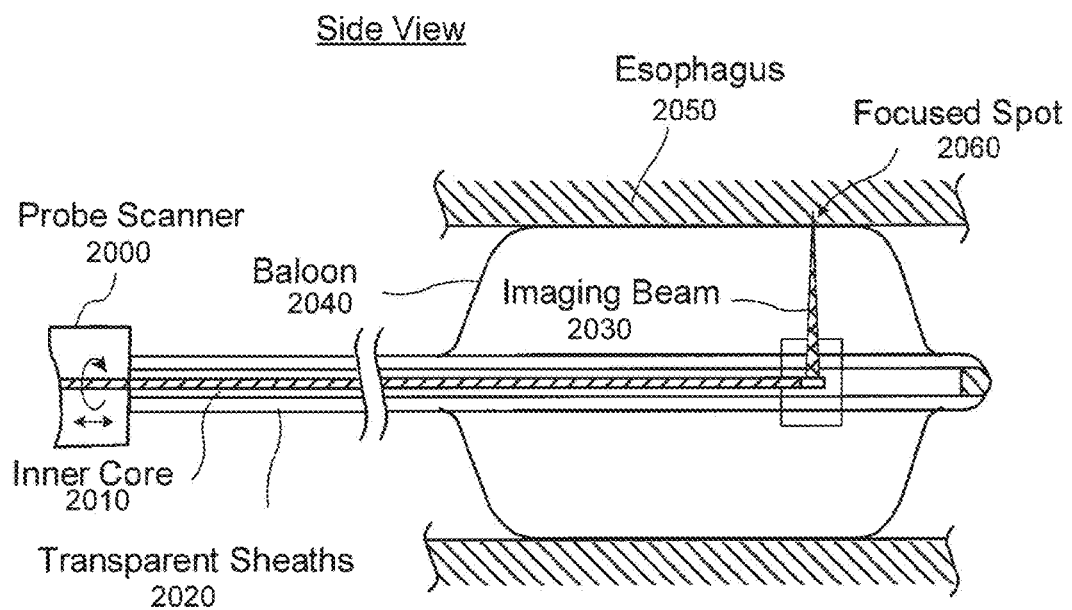
F I G. 1A
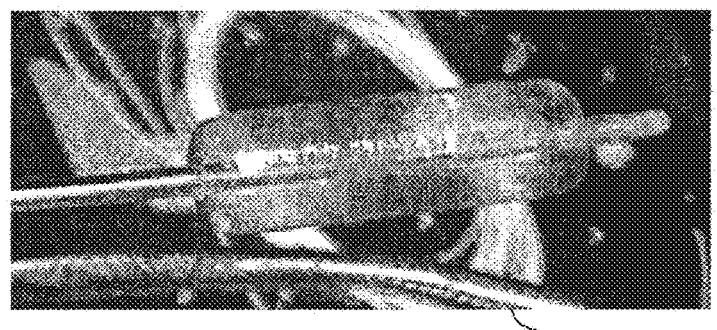
F I G. 1B

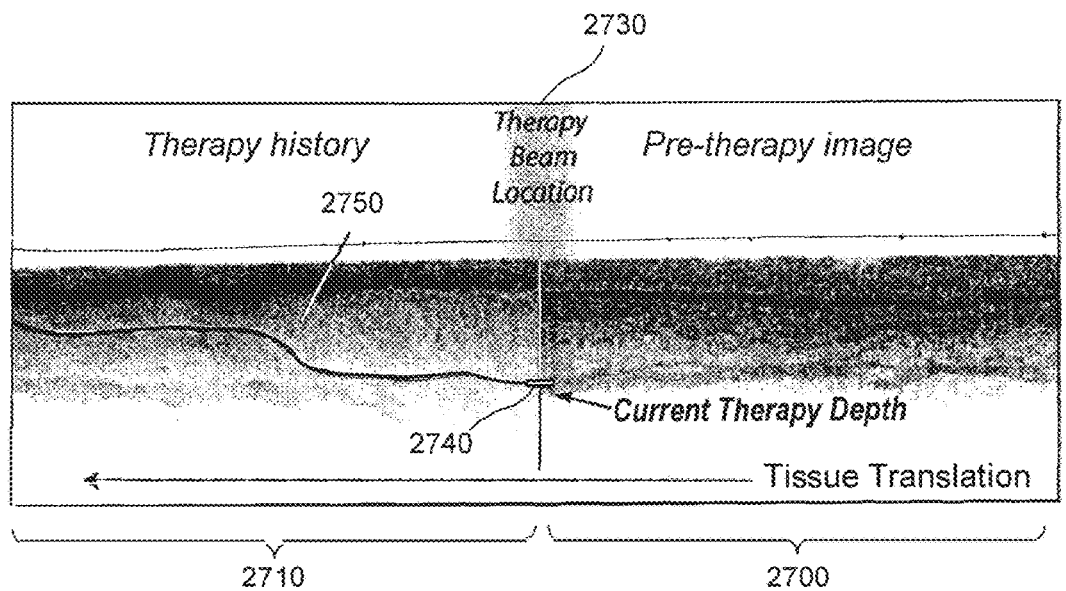
F I G. 14
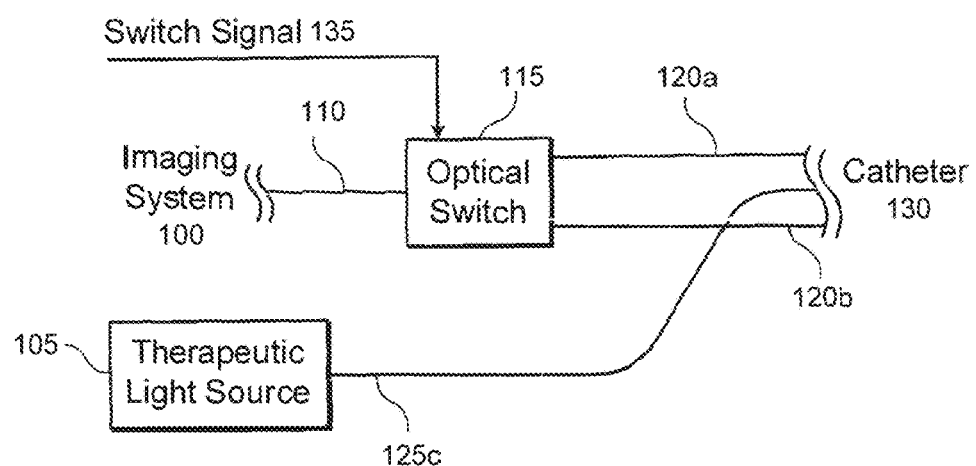
F I G. 15

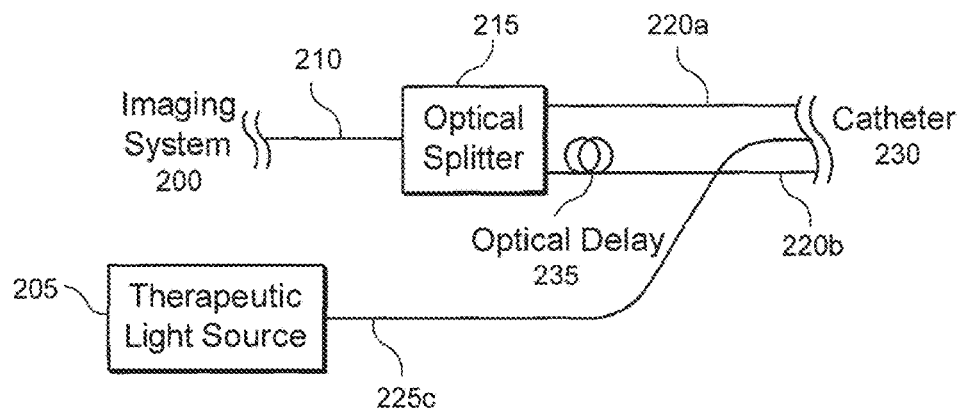
F I G. 16
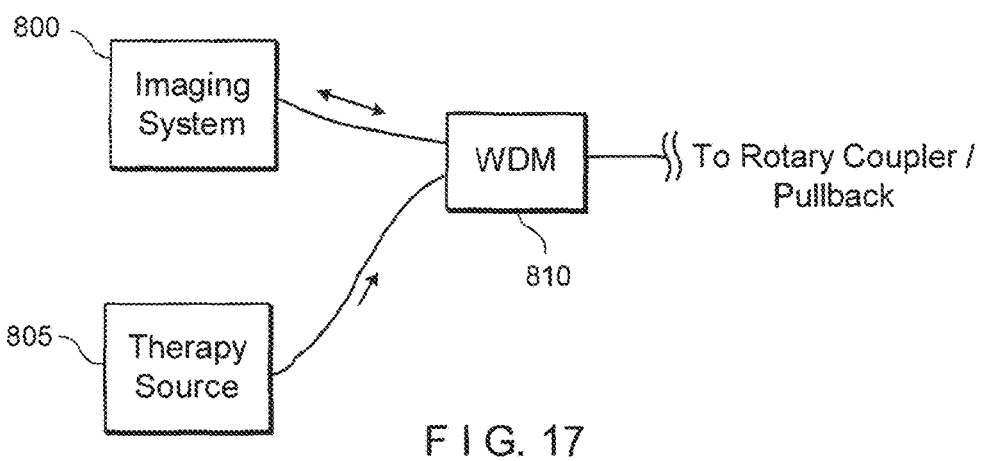
F I G. 17
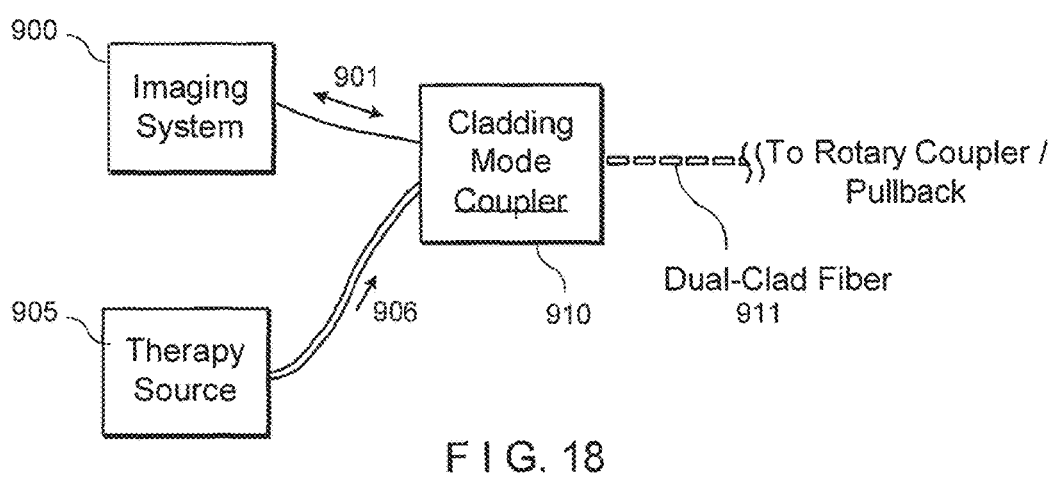
F I G. 18

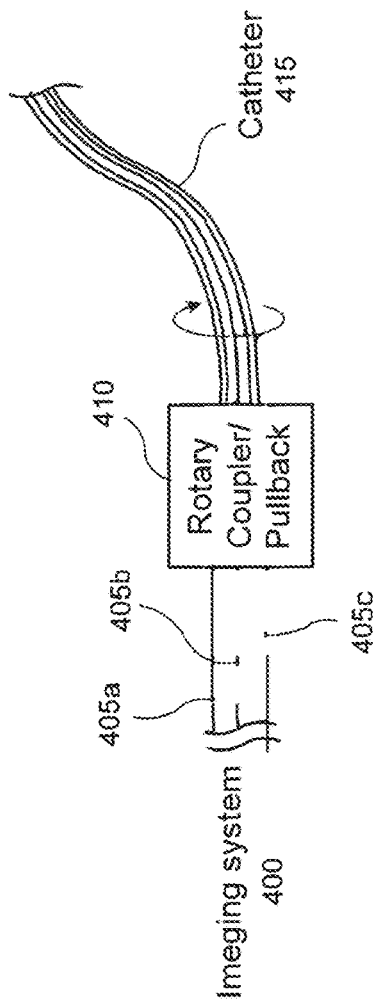
F I G. 19
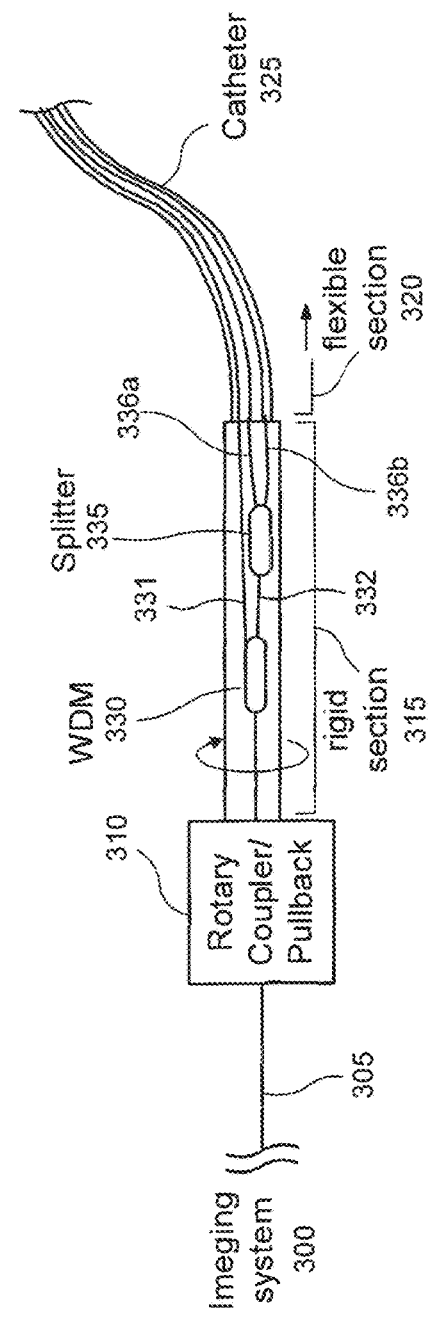
F I G. 20

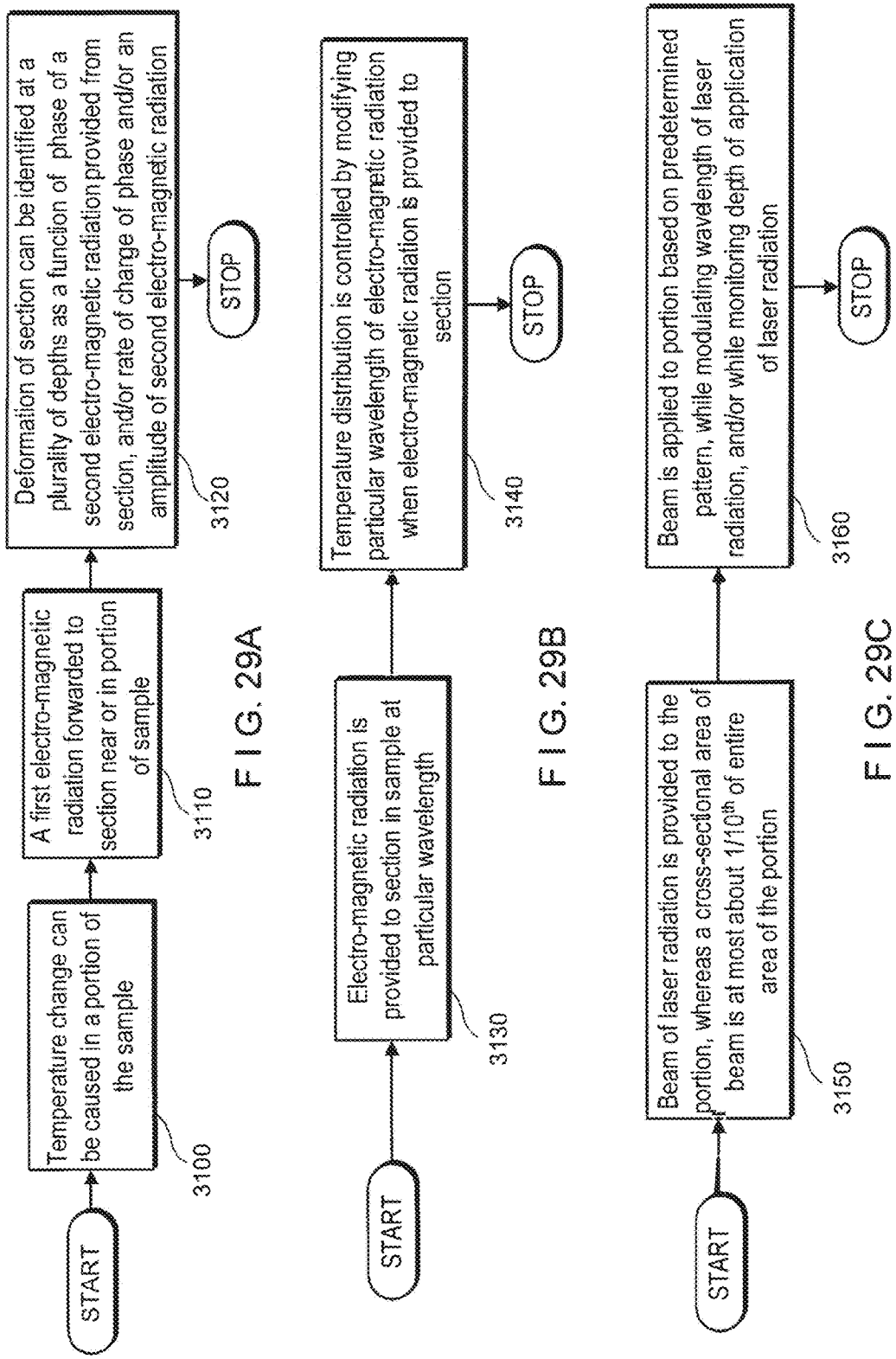

METHODS AND SYSTEMS FOR PROVIDING ELECTROMAGNETIC RADIATION TO AT LEAST ONE PORTION OF A SAMPLE USING CONFORMAL LASER THERAPY PROCEDURES

CROSS-REFERENCE TO RELATED APPLICATION(S)

This application is based upon and claims the benefit of priority from U.S. Patent Application Ser. No. 60/764,622, filed Feb. 1, 2006 and U.S. Patent Application Ser. No. 60/810,869, filed Jun. 1, 2006, the entire disclosures of which are incorporated herein by reference.

STATEMENT REGARDING FEDERALLY SPONSORED RESEARCH

The invention was made with the U.S. Government support under Contract No. 17-02-2-0006 awarded by the US Department of the Army Cooperative Agreement (DAMD). Thus, the U.S. Government has certain rights in the invention.

FIELD OF THE INVENTION

The present invention relates to systems and methods for controlling an application of at least one electromagnetic radiation in at least one portion of a sample using conformal laser therapy procedures.

BACKGROUND OF THE INVENTION

A use of lasers for ablating or thermally destroying diseased tissue is known and at time preferred, primarily due to the potential for precise local effect with minimal collateral damage. In practice, however, laser therapy has been less than perfect for use in certain clinical applications, such as the treatment of early epithelial cancers and their precursors. One of the problems with laser therapy for these applications has been the inability to accurately control and guide the treatment depth, resulting in either disease recurrence due to incomplete therapy or complications associated with overly aggressive treatment.

Epithelial Cancer: Diagnosis and Treatment

Methods and techniques for identifying and treating cancer at an early stage have been widely pursued as offering the potential to dramatically decrease the morbidity and mortality associated with metastasis. Since epithelial cancers and precursor lesions are frequently focal and can be distributed heterogeneously across a wide field, a sensitive diagnosis is extremely demanding. A diagnosis should be rendered on the size scale of a single cell in a field comprising possibly more than a billion cells.

Epithelial cancer also presents challenges for therapy. Since they are superficial, access to epithelial lesions can frequently be obtained through the use of minimally invasive catheters or endoscope. The therapeutic challenge, however, is in comprehensively killing, resecting or ablating the entire lesion without damage to underlying or adjacent tissues. This is particularly challenging since the depth of disease and even the thickness of normal epithelial layers can vary substantially. Additionally, epithelial tissues are highly compliant and therapeutic instrumentation can result in significant compression. As a result, therapies designed to affect tissue to a fixed depth risk either under-treatment resulting in recurrence, or over-treatment that can lead to significant complications.

Barrett's Esophagus

The importance of Barrett's esophagus (BE) is based primarily on the prevalence of this disease, the rapid increase in its incidence, and the dismal prognosis for patients with high-grade dysplasia and adenocarcinoma as described in publication 1 identified below. The current consensus (as described in publications 2 and 3 identified below) holds that comprehensive destruction of BE in a controlled fashion, along with anti-reflux treatment, results in squamous regrowth and that continued reflux control prevents the return of BE. The challenge is in achieving comprehensive removal of the pathologic mucosa, while preserving the underlying tissues of the esophageal wall. Treatment that is incomplete can result in a squamous overgrowth that masks underlying pathology. Overly aggressive therapy can result in stricture or perforation of the esophageal wall. Provided below is the information relating to screening and therapy of BE.

Screening

Several approaches for esophageal screening in the management of BE have been investigated. Brush cytology (as described in publications 4 and 5 identified below) and the use of biological markers, such as the deletion and/or mutation of the 17 p (p 53) gene, (as described in publications 6 and 7 identified below) can be used independently of endoscopy but cannot provide spatial mapping of disease. High magnification video endoscopy (as described in publication 8 identified below), fluorescence spectroscopy (as described in publications 9 identified below), and light-scattering spectroscopy (as described in publications 10 identified below) each show promise for point diagnoses, but provide insufficient information regarding subsurface microstructure and have not been demonstrated for wide-field screening. High-resolution endoscopic ultrasound and chromoendoscopy (as described in publications 11 and 12 identified below, respectively) can both be applied to a wide field, but have suffered from low sensitivity and specificity.

Optical coherence tomography (OCT) system, methods and techniques (as described in publications 13 and 14 identified below) has been developed. Certain accurate OCT diagnostic criteria have been developed for specialized intestinal metaplasia, dysplasia and adenocarcinoma, as described in International Patent Application PCT/US2004/029148, filed Sep. 8, 2004, U.S. patent application Ser. No. 10/501,276, filed Jul. 9, 2004, and publications 15-17 identified below. For example, advances in OCT technology have occurred demonstrating that the acquisition of an OCT signal in the wavelength domain (as opposed to the time domain) can provide orders of magnitude improvement in imaging speed while maintaining excellent image quality, as described in publications 18-20 identified below. One such exemplary second-generation imaging technology has been developed, e.g., optical frequency domain imaging (OFDI), as described in U.S. patent application Ser. No. 11/266,779, filed Nov. 2, 2005 and publication 21 identified below. With OFDI methods, techniques and systems, high-resolution ranging can be conducted in a tissue by detecting spectrally-resolved interference between the tissue sample and a reference while the source wavelength is tuned. (See, e.g., publication 22 identified below). Currently, OFDI methods, techniques and systems may be capable of capturing (e.g., 10 µm) 3 voxels at rates of approximately 40 million per second and the imaging speeds may likely be more than double in the near future, as provided in publication 23 identified below. Additionally, phase-sensitive OFDI methods, techniques and systems has been used for imaging flow, as provided in publication 24 identified below.

Controllable Therapy

Certain endoluminal approaches have been evaluated for the treatment of SIM (with and without dysplasia), including photodynamic therapy (PDT) (as provided in reference 25 identified below), laser (532 nm and 1064 nm) (as provided in reference 26 identified below), multipolar electrocoagulation (as provided in reference 27 identified below), argon plasma coagulation (as provided in reference 28 identified below), endoscopic mucosal resection (as provided in reference 29 identified below), radiofrequency ablation (as provided in reference 30 identified below) and cryoablation (as provided in reference 31 identified below) using liquid nitrogen. Although each of these techniques appear to be successful, most studies describe non-uniform therapy that can potentially result in persistent SIM or excessively deep ablation, resulting in stricture or perforation. In a study of over 100 patients, PDT may result in a stricture rate of 30% for single treatments and 50% for more than one treatment (as provided in reference 32 identified below). An exemplary reason for failure is not entirely clear but possible contributing causes include the operator-dependent nature of many of these hand-held, hand-aimed devices, the large surface area that requires treatment and the inherent preference for a physician-determined visual end point for the treatment (as provided in references 3 and 30 identified below). Additionally, a high variability may exist in the thickness of mucosal layers within and between patients and have directly observed significant compression of the soft tissues of the esophagus. The prior therapeutic approaches, however, do not account for the variability of layer thickness or compressibility of the esophageal wall.

Accordingly, there is a need to overcome the deficiencies described herein above.

OBJECTS AND SUMMARY OF THE INVENTION

To address and/or overcome the above-described problems and/or deficiencies as well as other deficiencies, exemplary embodiments of methods and systems can be provided for controlling an application of at least one electromagnetic radiation in at least one portion of a sample using conformal laser therapy procedures.

Such deficiencies can be addressed using the exemplary embodiments of the present invention. In one exemplary embodiment of the present invention, method and system can be re provided for applying a laser radiation to at least one portion of a biological structure. For example, a beam of the laser radiation can be provided to the portion, whereas a cross-sectional area of the beam is at most about 1/10th of an entire area of the at least one portion. The beam can be applied to the portion (a) based on a predetermined pattern, (b) while modulating a wavelength of the laser radiation, and/or (c) while monitoring a depth of the application of the laser radiation.

Further, the beam can be applied to the portion while modulating a scanning speed and/or a power of the laser radiation. The beam can have a first cross-sectional width in which at least 50% of power of the laser radiation is contained. When the beam is applied to the biological structure along a predetermined path in the portion, the amount of energy of the laser radiation applied to a second area of the biological structure that has a second width and includes the predetermined path may be approximately constant. The first and second widths can be approximately the same and are measured transverse to a translation direction of the beam. The beam can have a shape such that an integration of a power of the laser radiation in a direction that is approximately parallel to a scanning direction of the laser radiation is approximately constant. The beam can be shaped using at least one non-circular aperture. A shape of the beam can be modified to be non-circular. The predetermined path can be approximately be (i) approximately helical, (ii) approximately circular, and/or (iii) a set of approximately parallel lines. The biological structure can have a tubular shape.

These and other objects, features and advantages of the present invention will become apparent upon reading the following detailed description of embodiments of the invention, when taken in conjunction with the appended claims.

BRIEF DESCRIPTION OF THE DRAWINGS

Further objects, features and advantages of the present invention will become apparent from the following detailed description taken in conjunction with the accompanying figures showing illustrative embodiments of the present invention, in which:

FIG. 1A is a schematic diagram of an OFDI balloon catheter in accordance with an exemplary embodiment of the present invention;

FIG. 1B is a photograph of the OFDI balloon catheter shown in FIG. 1A;

FIG. 14 is a conceptual rendering of an image which can provide feedback to a user obtained using an exemplary embodiment of the present invention;

FIG. 15 is a block diagram of a sample arm of an OFDI system incorporating an optical switch in accordance with a further exemplary embodiment of the present invention;

FIG. 16 is a block diagram of the sample arm of the OFDI system incorporating an optical splitter in accordance with a still further exemplary embodiment of the present invention;

FIG. 17 is a block diagram of the sample arm of the OFDI system incorporating a single wavelength-division multiplexer in accordance with yet further exemplary embodiment of the present invention;

FIG. 18 is a block diagram of the sample arm of the OFDI system incorporating a cladding mode coupler and a dual-clad fiber in accordance with still another exemplary embodiment of the present invention;

FIG. 19 is a block diagram of a three-port rotary coupler and catheter in accordance with an exemplary embodiment of the present invention;

FIG. 20 is a block diagram of a single-fiber rotary coupler with subsequent demultiplexing of the therapy light and capable of splitting of imaging light in accordance with another exemplary embodiment of the present invention;

FIG. 29A is a flow diagram of an exemplary embodiment of a method for obtaining information associated with at least one portion of a sample according to the present invention;

FIG. 29B is a flow diagram of another exemplary embodiment of the method for controlling a temperature distribution in the sample according to the present invention; and FIG. 29C is a flow diagram of yet another exemplary embodiment of the method for applying a laser radiation to at least one portion of a biological structure according to the present invention.

Figure 2:
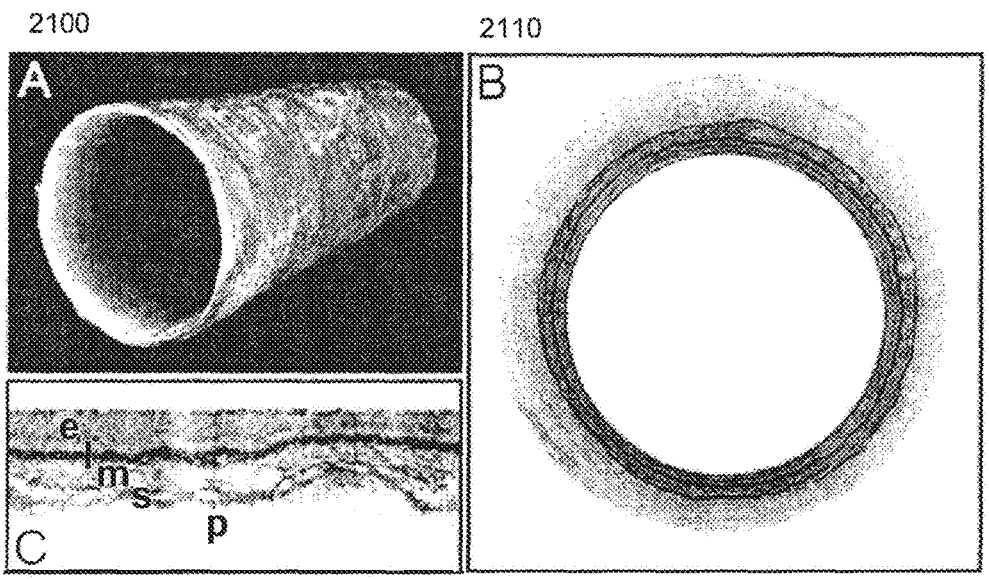
FIG. 2A is an exemplary image of a perspective view of a swine esophagus obtained using the OFDI balloon catheter in accordance with an exemplary embodiment of the present invention.
FIG. 2B is an exemplary image of a top view of the swine esophagus of FIG. 2A.
FIG. 2C is an exemplary image of a side view of a wall of the swine esophagus of FIG. 2A.

Throughout the figures, the same reference numerals and characters, unless otherwise stated, are used to denote like features, elements, components or portions of the illustrated embodiments. Moreover, while the subject invention will now be described in detail with reference to the figures, it is done so in connection with the illustrative embodiments. It is intended that changes and modifications can be made to the described embodiments without departing from the true scope and spirit of the subject invention as defined by the appended claims.

DETAILED DESCRIPTION OF EXEMPLARY EMBODIMENTS

An exemplary embodiment of the system and method according to the present invention for controlling and localizing therapy can be based on a thermal excitation delivered by a conventional, spatially scanned laser beam. For example, in the absence of photochemical or phase transition processes, the laser energy absorbed by tissue can be substantially or entirely converted to a temperature rise, as described in publication 33 identified below. For exposure durations greater than approximately 10 ms, temperatures in excess of 60-70° C. generally can lead to irreversible protein denaturation and cell death irrespective of duration, as described in publication 34 identified below. When the energy is absorbed, it can be subject to a spatial redistribution by a thermal diffusion. In 1983, as described in publication 35 identified below, an exemplary concept was described which provided that spatially confined microsurgical effects (selective photothermolysis) can be achieved by the use of laser exposures that are shorter than the characteristic thermal diffusion time of the heated volume. For a relatively large (>1 mm) diameter laser beam and laser wavelengths in the vicinity of 1450 nm, this characteristic diffusion time for biological tissues may be on the order of 1 second. Under these conditions, the temperature increase can be determined by the laser power density, $P_d$, the absorption coefficient, $\mu a$, and the duration of exposure t (as described in publications 33 and 34 identified below) as follows:

$$\Delta T(t, r, z) \approx \frac{P_d t \mu_a}{\rho c} \exp\left(-\mu_a z - \frac{2r^2}{W^2}\right) \qquad \text{Eq. 1}$$

where ρ is the tissue density, c the heat capacity, and r the radial distance from the center of a Gaussian laser beam of 1/e2 radius, W. Although this approximation neglects scattering of the laser light as it propagates into the tissue, models that explicitly include scattering (as described in publication 36 identified below) indicate less than 10% deviation from Eq. 1 under the stated conditions.

Since the absorption coefficient is wavelength-dependent, Eq. 1 indicates that laser parameters $P_d$, t, and wavelength can be used to control the depth of thermal injury and to minimize collateral damage to underlying tissues. Operating in the visible portion of the spectrum is challenging since absorption is governed by a wide range of chromophores whose concentration is highly variable across different tissues and pathologic conditions. By comparison, the absorption spectrum of biological tissues near 1.45 µm may be dominated by water, and can therefore be roughly constant across a range of tissues. Additionally, by tuning over a modest wavelength range, from 1375 nm to 1430 nm for example, absorption lengths can be selected that range from over 2 mm to 300 µm. This exemplary range is well matched to the depths characteristic of epithelial lesions.

Exemplary Monitoring

Several approaches have been investigated for monitoring laser therapy, including the analysis of the acoustic transients generated during ablation (as described in publication 37 identified below), changes in tissue reflectivity (as described in publications 38 and 39 identified below), fluorescence spectroscopy for discrimination between plaque and vessel wall (as described in publication 40 identified below), plasma spectroscopy to distinguish between bone and nerve tissue (as described in publication 41 identified below), and analysis of the cavitation bubble dynamics at the tip of a laser optical probe for controlled sclera perforation in glaucoma surgery (as described in publication 42 identified below). With the exception of the procedures that are based on a reflectivity described in publications 38 and 39, in each of such methods, the monitoring signal arose only after the zone of thermal injury has transitioned across a boundary of the specific tissue types. None could determine the depth of thermal injury or the spatial relationship of the damaged tissue to adjacent viable tissue. Certain degree of spatial resolution has been achieved by monitoring the portion of laser light that is not absorbed by the tissue. By inserting an optical fiber through a needle, this light can be collected from different perspectives surrounding the heated volume and temperature-dependent scattering changes can be measured (as described in publication 43 identified below). A more direct approach, high-resolution in situ imaging, has also been demonstrated for visualizing scattering changes and the physical removal of tissue resulting from ablative laser irradiation (as described in publication 44 identified below).

Exemplary embodiments of monitoring systems, methods and techniques according to the present invention may utilize information regarding well-known tissue responses to a thermal injury. These exemplary responses can include, but not limited to, microscopic deformation (as described in publication 33 identified below) and changes in scattering (as described in publications 36, 38 and 45 identified below), birefringence (as described in publication 46 identified below), and blood flow (as described in publication 47 identified below) that can result from laser heating and that can be observed over a range of temperatures beginning as low as 45° C. One exemplary aspect of an exemplary embodiment of the method and technique according to the present invention is that these thermal responses can be detected with high spatial resolution and presented in a cross-sectional image format along with the microscopic tissue structure.

Exemplary Strategies for Conformal Laser Therapy

According to an exemplary embodiment of the present invention, a system, arrangement and method can be provided that are capable of screening and delivering precisely guided laser therapy. Since the characteristic length-scales preferably usable for comprehensive screening and comprehensive therapy are likely distinct, it is possible to separately perform these objectives. For example, the screening (e.g., possibly performed as a first step) may utilize comprehensive imaging technique(s) with a resolution on the cellular size-scale. This exemplary procedure can be used to identify regions for subsequent therapy. After the performance of the screening procedure, the endoscopic probe can be directed back to the specified regions, and therapy may be performed under real-time guidance so that all disease is treated and collateral damage is minimized. This exemplary result can improve the management of patients with Barrett's esophagus by, e.g., increasing the effectiveness of therapy while decreasing the risk of complications.

Although described in conjunction with a treatment of epithelial cancers, the exemplary embodiments of the system, techniques and methods according to the present invention can be applicable to any application of laser treatment including but not limited to, for example, applications in dermatology. Some relevant epithelial cancers and precancerous lesions addressed by the exemplary embodiments of the present invention can include, but not limited to, the larynx, cervix and ovaries, bladder, oral cavity and lung. In addition, the exemplary embodiments of the present invention can be applicable to the areas of monitoring photodynamic therapy, radiofrequency ablation, and cryotherapy to provide control over depth and spatial extent of therapy.

Exemplary Wide-Field Screening

In order to perform an effective screening procedure, it is preferable to conduct a comprehensive examination of large surface areas and the application of accurate diagnostic criteria in order to identify specific regions of pathology. Various OCT diagnostic criteria has been developed and verified for specialized intestinal metaplasia, dysplasia and adenocarcinoma, as describe in publications 15-17 identified below. For example, across 288 biopsies obtained from 121 patients, a sensitivity and specificity for diagnosing SIM (versus all other upper GI tract tissues) has been determined of about 97% and 92%, respectively, as described in publication 16 identified below. Until recently, however, the exemplary OCT technique was too slow to image large mucosal surface areas. As discussed herein below, advances have been made that may overcome this timing issue, and provide a preliminary demonstration of comprehensive esophageal imaging in vivo.

Optical Frequency-Domain Imaging (OFDI)

As described above, publication 21 identified below describes the development of the OFDI technique as an alternative to the use of the OCT techniques. Although the light source (as discussed in publication 22 and 23 identified below) and the detection principles of OFDI are useful, the contrast, resolution and cross-sectional image presentation are approximately equivalent or similar to those provided by OCT. One of the advantages of OFDI is that OFDI has a higher detection sensitivity, thus enabling a significant increase in the image acquisition speed, without compromising image quality. The system used for these preliminary studies was designed specifically for endoscopic imaging and provides an acquisition rate of 10,000 depth-scans (A-lines) per second, an axial resolution of 8 µm in tissue, and a ranging depth of 3.5 mm, as described in publication 24 identified below. The imaging speed of this exemplary system is limited solely by the rate at with which data can be transferred across the computer's bus and stored to a hard drive.

Exemplary Balloon Catheter

For comprehensive esophageal imaging, an exemplary embodiment of an OFDI catheter may be provided in accordance with the present invention that can be centered within the esophageal lumen using a balloon sheath shown in FIGS. 1A and 1B. The exemplary catheter may include of a probe scanner 2000 which can rotate, and may pull back an inner optical core 2010. The inner core 2010 can be enclosed within a transparent sheath 2020. At the distal end of the catheter, the balloon 2040 which, when inflated, may center the imaging optics. The imaging beam 2030 can be focused onto the esophageal surface 2050. This imaging beam 2030 may be scanned to achieve comprehensive imaging. The balloon 2040 can have an inflated diameter of 1.8 cm, and may allow for a longitudinal imaging over a length of 4.5 cm without repositioning. The optical core 2010 of the catheter can include an optical fiber, a spacer for expansion of the optical beam, a gradient index lens for focusing, and a right-angle prism for directing the beam perpendicularly to the longitudinal axis of the catheter. A miniature cylindrical lens was fabricated in-house and placed on the second surface of the prism. This lens compensated for astigmatism induced by the plastic sheaths and resulted in a diffraction-limited beam (30 µm diameter) on the tissue surface. In use, the exemplary catheter may be rotated at rate of about 4 revolutions per second, allowing the acquisition of 2500 axial scans per circular cross-section. This exemplary OFDI system can record an encoder signal to precisely track the rotation and pull-back of the catheter. This information is used in reconstructing the 3-dimensional data set.

Preliminary Porcine Esophageal Imaging

The esophageal imaging techniques can be performed in two ~50 kg swine. Although the complete 20 GB data set may likely not be represented in discrete figures, the information content is shown by FIGS. 2A-2C. For example, in a perspective view of FIG. 2A, an image 2100 provides a 3D rendering of the entire imaged esophagus. In a front view of FIG. 2B, an image 2110 illustrates a single transverse cross section of the imaged esophagus. In FIG. 2C, image 2120 shows a zoomed cross sectional image of at least one portion of the esophagus. A sampling with a resolution of 10 µm×20 µm×30 µm (r,θ,z) can yield a comprehensive microscopic data set that can be displayed volumetrically a the image 2100 of FIG. 2A for mapping and orientation, or in high-resolution cross-sectional images in which the entire esophageal wall can be visualized as the image 2110 in FIG. 2B. An expanded view of the image 2120 of FIG. 2C depicts the architectural structure of the mucosal layers.

Preliminary Human Esophageal Imaging

Figure 3:
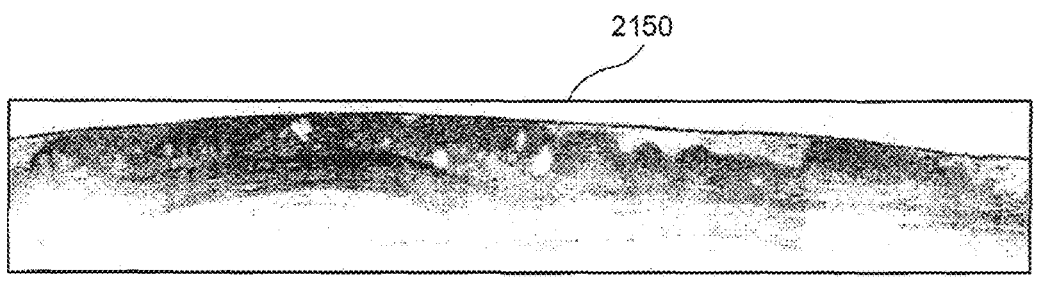
FIG. 3 is an exemplary OFDI image acquired in a human subject using a BE technique in accordance with an exemplary embodiment of the present invention.

An exemplary single rotational image 2150 is shown in FIG. 3. Hallmark features of SIM (disorganized epithelial architecture with irregular surface; presence of large epithelial glands) of a patient are shown therein. This patient had a prior diagnosis of BE, and imaging was performed prior to PDT.

These preliminary studies demonstrate that a) comprehensive OFDI microscopic imaging in vivo is feasible, b) the architectural structure of the entire esophageal wall can be visualized, and c) features important to the diagnosis of SIM in human subjects can be detected using the balloon centering probe.

Monitoring Laser Thermal Injury

In response to heating, tissue proteins and collagen can denature, giving rise to microscopic deformation (described in publications 33 identified below), increased in scattering (described in publications 36, 38 and 45 identified below), reduced birefringence (described in publication 46 identified below), and reduced blood flow (described in publication 47 identified below). The description below provides the methods for monitoring these changes using exemplary OFDI in accordance with the exemplary embodiments of the present invention. In the exemplary demonstration of each, freshly obtained porcine esophagus samples and duodenum samples (as a proxy for SIM) were mounted with a microscope cover glass on the epithelial surface so that the approximate pressure and thermal conductivity of the balloon catheter could be simulated.

Figure 4:
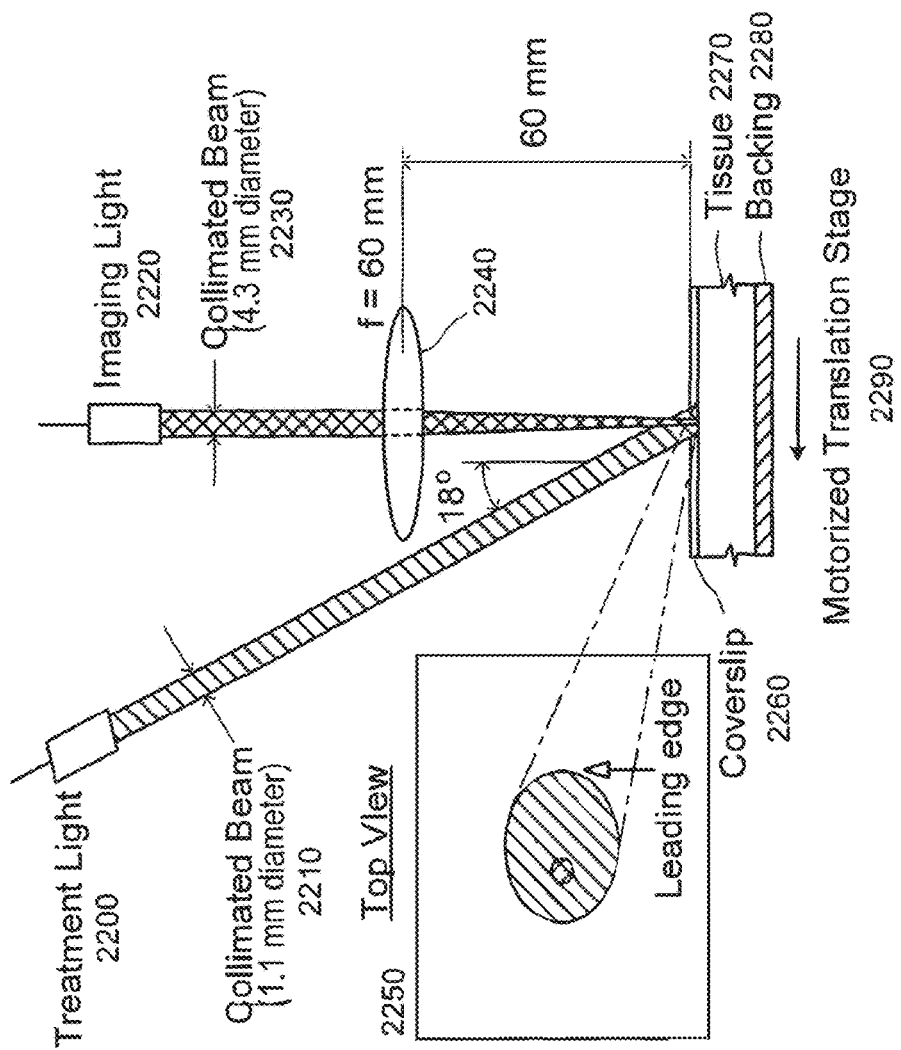
FIG. 4 is a schematic diagram of exemplary arrangement and usage thereof for treating and monitoring tissue in accordance with an exemplary embodiment of the present invention.

An exemplary embodiment of an apparatus for collecting OFDI signals during a laser irradiation and use thereof according to the present invention is shown in FIG. 4. For example, the treatment light is delivered through a collimator 2200. The imaging light is delivered through a second collimator 2220. The treatment beam 2210 and imaging beam 2230 overlap when reaching the tissue 2270 which is covered with a thin glass cover slip 2260 and resting on a backing 2280. The tissue is translated by a motorized translation stage 2290. The imaging beam is focused by a lens 2250. The top-down image depicting beam overlap 2250 is provided. For a thermal excitation, a collimated, high-power Gaussian laser beam (e.g., diameter=1.1 mm; wavelength=1450 nm; power=400 mW) can be used. The OFDI sampling beam can be focused at the tissue surface to, e.g., a 1/e2 intensity diameter of 23 µm and aligned so that it overlapped with the laser spot as shown in FIG. 4. During the data collection, the samples may be held at a fixed location and/or translated using a motorized stage.

Exemplary Microscopic Deformation

As laser energy is deposited in tissue, the resulting temperature increase can denature proteins and collagen. These changes can be manifested by microscopic deformation that can be measured using phase-sensitive OFDI. The following data demonstrates this capability.

Fixed Spot—

Figure 5:
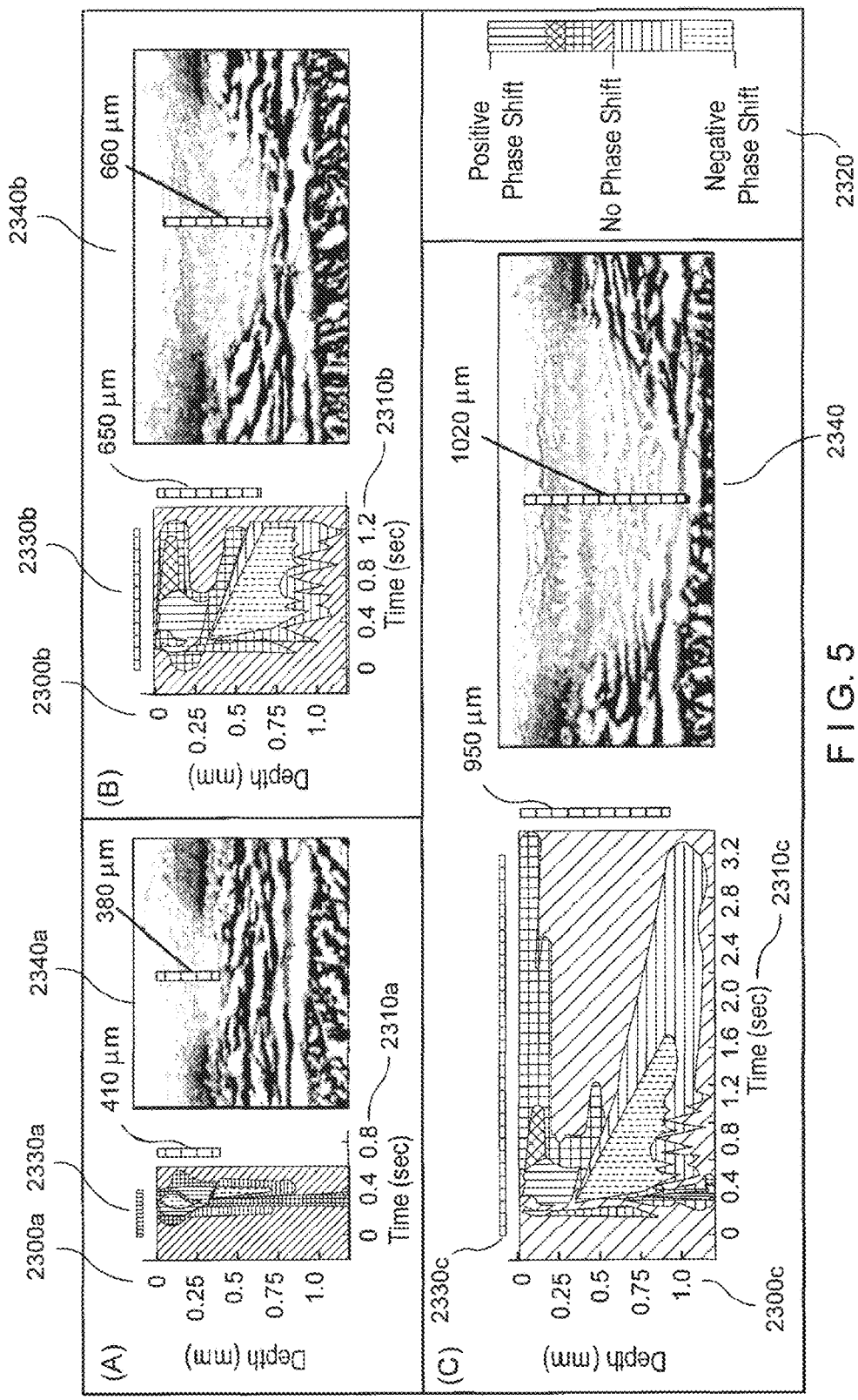
FIG. 5 is a set of multiple exemplary m-mode OFDI phase images obtained using the exemplary arrangement of FIG. 4 together with a corresponding histology.

For such exemplary experiment, the samples were held at a fixed location. OFDI depth-scans were acquired continuously at a rate of about 10 kHz while the 1450 nm laser was switched on, held at a constant power of 400 mW for a predetermined duration, and switched off. Representative data for three different laser exposure durations is shown in the graphs of FIG. 5 as "M-mode" images where the vertical axis 2300a, 2300b, 2300c represents depth within the tissue, the horizontal axis 2310a, 2310b, 2310c denotes time and the magnitude of the measured phase-shift is represented using a color lookup table 2320 (red=positive phase-shift; blue=negative). A red horizontal line 2330a, 2330b, 2330c, at the top of each phase-shift image denotes the interval over which the laser was on. Upon initial laser exposure, a superficial region of positive phase-shift overlying a lower region of negative shift has been observed. As the laser irradiation continued, the depth at which the phase transitioned from positive to negative became progressively deeper and the magnitude of the overlying phase-shift decreased. No measurable phase-shift was detected after the laser was switched off. A protein denaturation gives rise to local microscopic structural changes and a nidus of local deformation that is detected as a phase-shift in the interferometric signal. As the laser exposure continues, the zone of active denaturation propagates in depth with overlying tissues becoming completely denatured. The depth at which the direction of the phase-shift reverses identifies the focal center of active denaturation.

To verify these results, histological sections were obtained following laser exposure and nitro-blue tetrazolium chloride (NBTC) staining was used to assess the extent of laser damage. NBTC stains positive for lactate dehydrogenase (LDH), which is a thermolabile enzyme; loss of LDH activity ensues rapidly upon heat induced cell damage and is correlated with cell lethality (as described in publications 48 and 49 identified below). Therefore, the depth of the border between unstained and stained tissue have been selected as the depth of laser damage. Corresponding phase-shift data and histology are shown in 2340*a*, 2340*b*, 2340*c*. The preliminary findings suggest that the border between thermally denatured tissue and viable tissue corresponds with the inflection point of the phase-shift measured with OFDI. Quantitatively, the depth-derivative of the phase-shift has been determined for each A-line and defined the depth of injury as the point of maximum negative value of the derivative. The depths determined in this way are provided in FIG. 5 as vertical lines adjacent to each M-mode image and show a good correspondence with histomorphometry.

Translating Spot—

Laser treatment of large epithelial surface areas can be facilitated by adding a therapeutic laser beam to the existing OFDI catheter so that the laser and OFDI beams are simultaneously scanned. The preliminary imaging studies demonstrated comprehensive esophageal imaging with an OFDI beam size of 30 µm. Obtaining a precise alignment of >1 mm diameter laser beam on successive rotational scans should therefore be obtainable. To simulate the monitoring while scanning, the computer-controlled translation stage 2290 (see FIG. 4) can be controlled to repetitively toggle the sample velocity from 1.8 mm/s to 0.9 mm/s.

Figure 6:
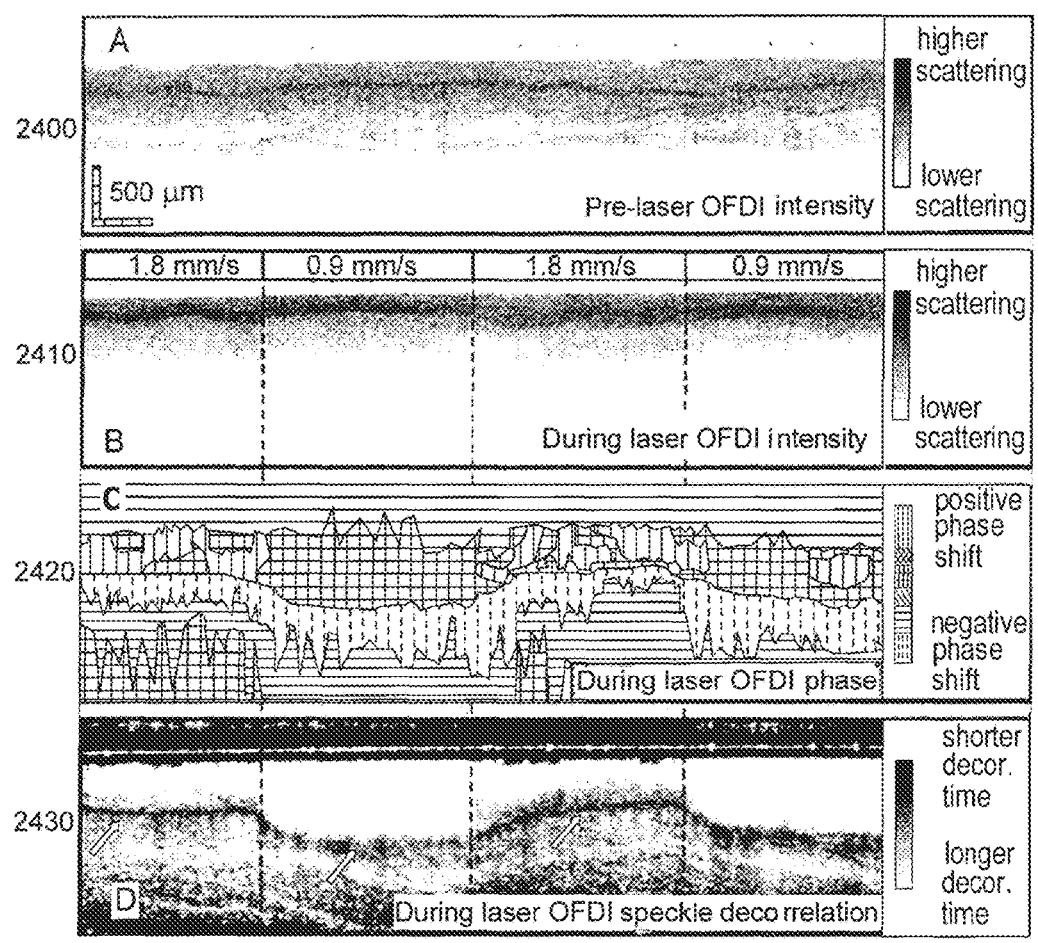
FIGS. 6A-6D are exemplary images associated with the OFDI data acquired for a translating sample in accordance with the exemplary embodiment of the present invention.

An OFDI intensity image 2400 acquired with no laser irradiation is shown in FIG. 6A. For the images 2410, 2420 and 2430 shown in FIGS. 6B, 6C, and 6D, respectively, the 1450 nm laser power was about 400 mW. The translation of the samples during the exposure resulted in a line of laser damage across the surface of the sample. Since the thermal energy deposition can be proportional to the exposure time (see Eq. 1), the depth of laser damage can vary along the line according to the inverse of the translation velocity. Histology sections, obtained from regions of fast and slow translation and with an orientation perpendicular to the line, indicated laser injury depths of 0.41 mm and 0.69 mm respectively. The phase-shift data corresponding to the image 2410 of FIG. 6B is illustrated as the image 2420 in FIG. 6C. In a substantial agreement with the histomorphometric measurements, the depth of the damage determined by the phase-shift data (max negative derivative) can be 0.40 mm and 0.67 mm in the regions of fast and slow velocity, respectively.

Speckle Decorrelation

Speckle is a phenomenon that is commonly observed when imaging with coherent illumination and manifests as a grainy pattern of high- and low-intensity that does not appear to correlate with the macroscopic structure. In tissue, speckle generally arises from the interference between photons that have traversed different paths during propagation within the sample. If the scatterers within the tissue are moving, even on a microscopic scale, the speckle pattern is likely seen to rapidly fluctuate. The measurements of the time-evolution of the speckle pattern can therefore provide insight into microscopic motion within the sample. This exemplary technique has been provided for investigating biomechanical properties (as described in publication 50 identified below), and thermal excitation (as described in publication 51 identified below), in biological tissues. The extension of these concepts to the depth-resolved monitoring of laser tissue interactions with OFDI has been reviewed.

Viewing the OFDI images of the tissue during laser exposure provides an indication of the potential of this exemplary technique. With no laser exposure, the speckle pattern observed in OFDI remained constant over the depth and transverse extent of the image. Under laser irradiation, the speckle pattern was observed to rapidly fluctuate in the local region of the laser beam. In slow-motion viewing, we observed that the speckle fluctuations began near the tissue surface and propagated downward in time. To quantify these observations, the rate of speckle decorrelation for each depth point of the image 2410 shown in FIG. 6B has been determined. In particular, the depth-dependent width of the temporal autocorrelation function of the OFDI intensity signal has been determined. Speckle decorrelation images were then generated by displaying the autocorrelation width using a grayscale lookup table. The image 2430 of FIG. 6D is the speckle decorrelation image corresponding to the images 2410 and 2420 of FIGS. 6B and 6C, respectively. The depth of the peak decorrelation 2431 rate (black band, denoted by arrows in FIG. 6D) can be observed to vary in correspondence with the translational rate of the sample and the depth of laser damage indicated in histology. The consistency of this finding across samples of esophagus and duodenum confirm that the depth of peak decorrelation rate is a quantifiable metric for determining the depth of laser injury.

Birefringence

As light propagates within materials, its polarization state can become altered if the index of refraction is non-isotropic. This effect is known as birefringence. Many tissues, especially muscle and collagen, exhibit strong birefringence which is lost upon thermal heating and denaturation (as described in publication 46). Polarization-sensitive OCT (PS-OCT) techniques, methods and systems have been described for quantifying burn depth through measurements of birefringence loss. (See publications 52 and 53 identified below). In PS-OCT, two detector channels can be configured to receive orthogonal polarization states of the light returning from the sample. Birefringent samples induce a depth-dependent rotation of the polarization state, resulting in a variation in the percentage of the sample light detected in each channel. If the ratio of the two channels is displayed as a grayscale in a cross-sectional image, birefringence is observed as a characteristic banding pattern.

Figure 27:
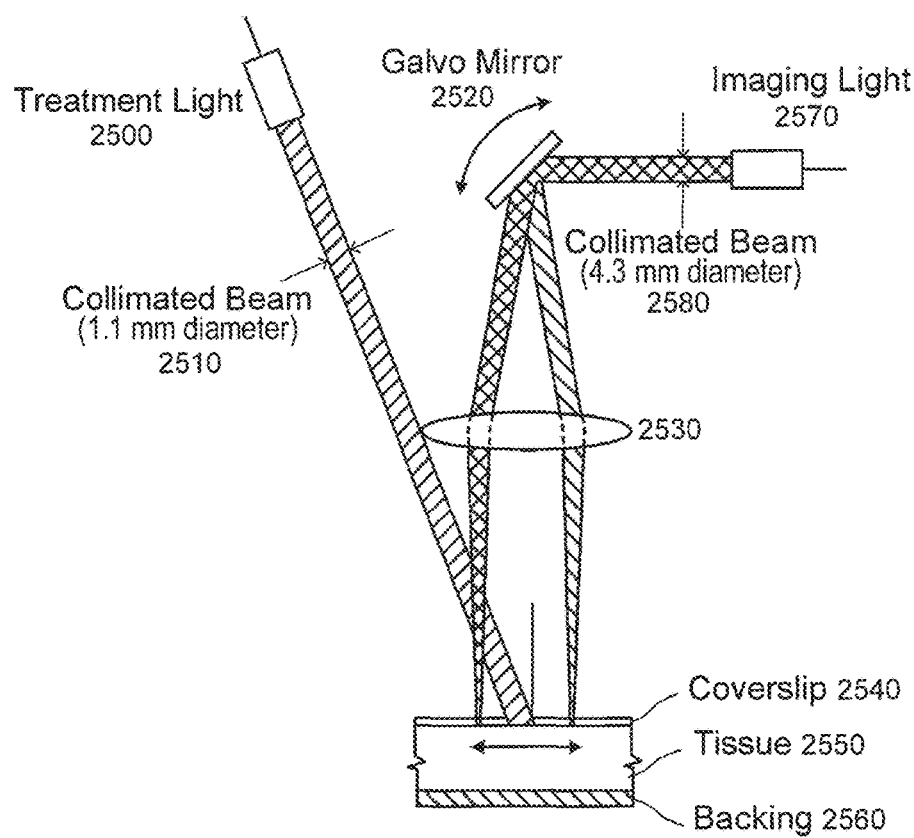
FIG. 27 is a side view of another exemplary embodiment of a system which includes a galvanometric scanner which can allow the OFDI beam to be repetitively scanned across the surface of the tissue, and usage thereof.

For example, the apparatus of FIG. 4 can be modified to include a galvanometric scanner so that the OFDI beam may be repetitively scanned across the surface of the tissue while the sample was held stationary and the 1450 nm laser spot remained fixed on center, as shown in FIG. 27. As shown in FIG. 27, the treatment light can be delivered through a first collimator 2500 providing a treatment beam 2510 incident on the tissue 2550 that is covered by a cover slip 2540 and against a backing 2560. The imaging light may be provided by a second collimator 2570 producing an imaging beam 2580 that is directed by a galvo-mirror 2520 through a lens 2530. This arrangement/system can be an exemplary embodiment of a therapeutic monitoring system applicable to applications in dermatology. OFDI images or video of esophageal and duodenal tissues were acquired during laser irradiation.

FIGS. 7A-7D show images of the representative data. In frames acquired prior to laser irradiation, the layered esophageal structure can be observed in the intensity image 2450 (see FIG. 7A) and characteristic birefringence banding can be observed in the corresponding polarization image 2460 (see FIG. 7B). In frames acquired during laser exposure, the epithelial scattering intensity may be increased dramatically within the 1.1 mm laser spot 2470 (see FIG. 7C), and the birefringence banding in the corresponding polarization image 2480 (see FIG. 7D) can be lost. Reviewing the polarization moving images in slow-motion, a zone of decreased birefringence can be observed that may begin near the surface and propagated downward. These observations are generally consistent with a downward propagating zone of denatured tissue. Measurements of the percent-loss of birefringence is a quantitative metric for monitoring laser thermal damage.

Scattering

Thermally induced changes to the microscopic structure of tissue can alter optical scattering. Since the signal in OFDI arises from scattering and small changes can be detected over a large dynamic range, we investigated the use of scattering measurements for monitoring thermally induced changes in tissue. Scattering changes observed in image 2460 of FIG. 7B may be representative of the preliminary observations in both duodenum and esophagus samples. In certain cases, it was determined that the significant scattering changes within the epithelium and relatively smaller changes in the underlying tissues of the muscularis mucosa and muscularis propria. For example, two potential quantitative metrics for laser damage that could be obtained from scattering measurements: changes in the depth-resolved scattering intensity and changes in the depth-integrated scatting intensity.

Blood Flow

Figure 8:
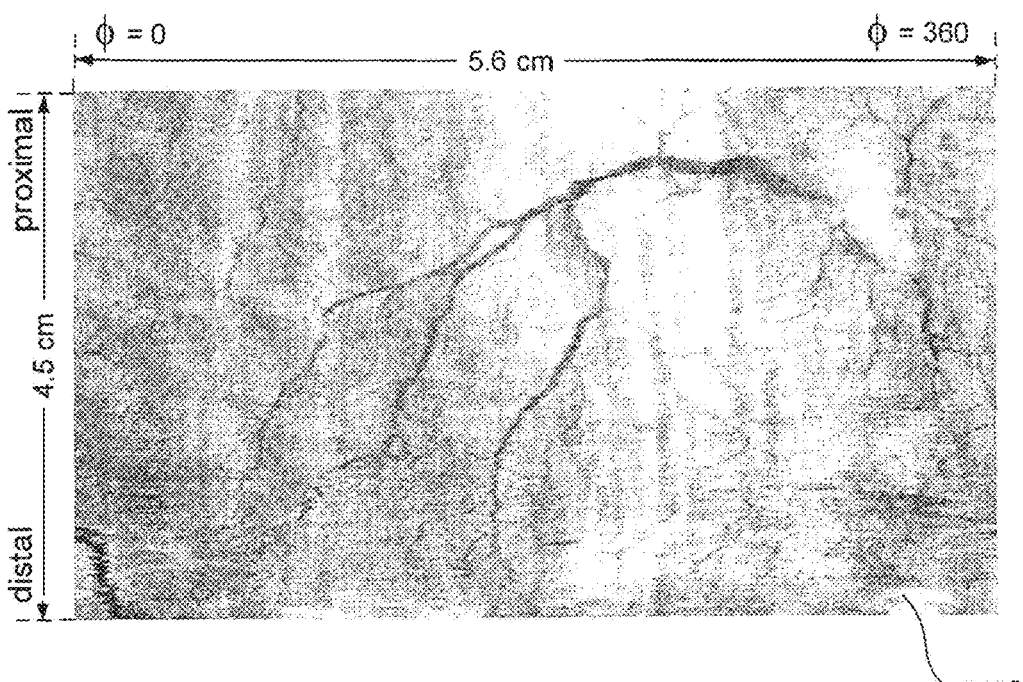
FIG. 8 is an image of an exemplary vascular map extrated from a comprehensive dataset obtained from porcine esophagus in-vivo which can be obtained using the exemplary embodiment of the present invention.

Laser therapy can to alter vessels and capillaries resulting in decreased blood flow (as described in publication 54 identified below). Since the esophageal mucosa is highly vascularized, monitoring changes in blood flow may provide an additional method for monitoring laser therapy. An image 2490 of FIG. 8, acquired during our recent swine studies, graphically illustrates the porcine esophageal vascularity. This exemplary image 2490 was generated by unwrapping the tubular image data to display the epithelial surface as if the esophagus was longitudinally opened and pinned flat. The intensity data has been integrated over depth into the tissue. Although this type of large scale visualization is a convenient way to map the vessels, it is possible to use a more sensitive and quantitative method/technique/system for measuring blood flow. Doppler OCT (as described in publications 55 and 56 identified below) has been demonstrated for visualizing and quantifying blood flow in tissue and has been investigated as an arrangement for assessing flow following laser therapy (as described in publication 57 identified below). The Doppler measurements with OFDI (as described in publication 24 identified below) have been described, and the possibility of simultaneously measuring structure and flow in vivo has been reviewed.

Figure 9:
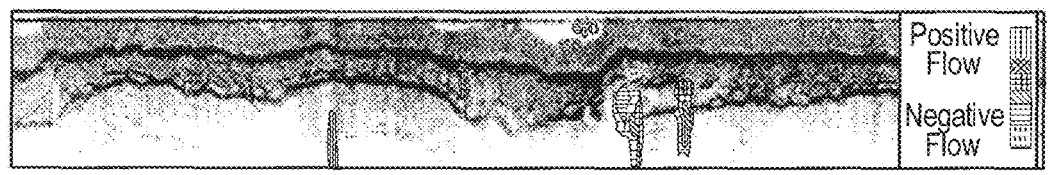
FIG. 9 is an exemplary in-vivo Doppler flow image of a porcine esophagus obtained using the exemplary embodiment of the present invention.

A cross-sectional view of an exemplary image 2590 of FIG. 9 has been acquired in the esophagus of a living swine and displays intensity as a grayscale and Doppler as a superimposed color. The coordinates (r,θ) of this data have been mapped to Cartesian coordinates (vertical, horizontal) for simplicity of display. This result was representative of our observations at multiple locations in two swine. Additionally, in time-sequences of Doppler images, we clearly observed pulsatile flow.

| Summary of Monitoring | | |
|---|---|---|
| Cause | Effect | Measurement |
| Thermal denaturing of cellular proteins and collagen | Focal deformation Loss of birefringence ΔScattering | Phase & Speckle Polarization Intensity |
| Thermal coagulation of vessels | Loss of blood flow | Doppler flow & Vascular Map |

Based on the preliminary investigation, the proposed measurements would likely be complementary: and the phase-shift and speckle decorrelation, which are only applicable during laser irradiation, may be more sensitive and provide greater spatial resolution. The changes in birefringence, scattering and flow are persistent and could be applied for follow-up imaging after laser treatment.

Exemplary Control

In addition to monitoring for laser thermal injury, effective conformal laser therapy may use precise control over the volume of treated tissue. One exemplary approach to controlling treatment depth is to operate within the conditions for thermal confinement in order to minimize collateral damage and to manipulate laser wavelength, power, and exposure time to control the depth of thermal injury. In the transverse dimension (along the epithelial surface), thermal injury can be controlled through the use of a raster-scanned, spatially-collimated beam. A flat-top beam with a diameter of 1-3 mm with well-defined edges may allow spatial control while also permitting therapy of large epithelial areas through raster scanning. Exemplary laser control parameters are described herein below in the context of Eq. 1. The temperature distribution of Eq. 1 generally applies only in the limit of weak scattering.

Wavelength

Figure 10:
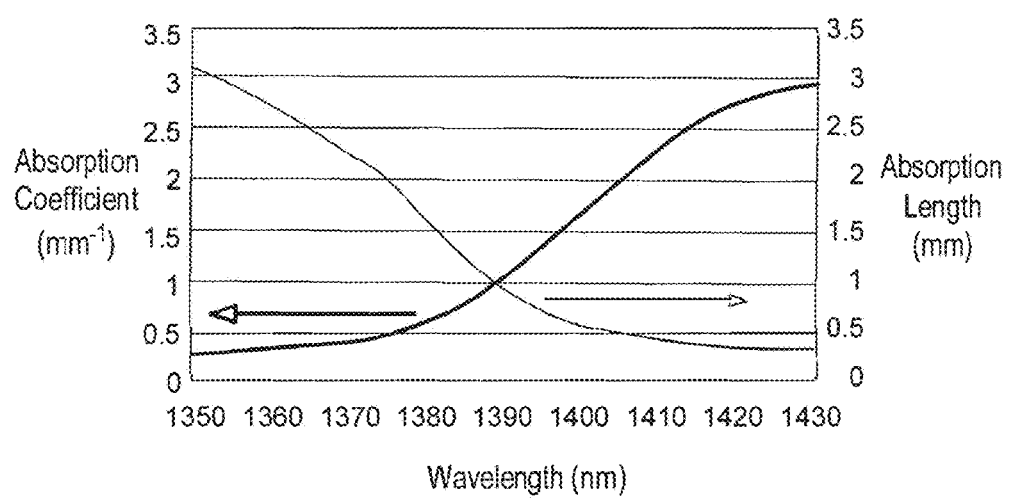
FIG. 10 is an plot of water absorption coefficient and corresponding penetration depth as a function of wavelength obtained using the exemplary embodiment of the present invention.

From the temperature distribution of Eq. 1, it is evident that $\mu_a$ would likely be an optimal parameter for control over depth of laser injury. Although $\mu_a$ is characteristic of the sample rather than an externally controllable parameter, in this invention we exploit the wavelength dependence of $\mu_a$ to achieve depth control. In this invention, we target the absorption coefficient at longer wavelengths where water absorption dominates. Since the water content is approximately constant in epithelial tissues, thermal injury depth can be closely regulated by changing the laser wavelength by small amounts. In the vicinity of the water absorption band near 1.45 μm, absorption lengths (see graph 2595 of FIG. 10) range from 0.3 mm to over 2 mm within a narrow spectral range (1375 nm to 1430 nm). These lengths correspond well to the characteristic length scales appropriate for the treatment of epithelial disease. A tunable laser, operable in the vicinity of the 1450 nm water absorption band can be used to control therapy through wavelength tuning.

Power and Exposure Duration

Upon the review of Eq. 1, the absorption coefficient does more than control the exponential depth decay of the temperature distribution; e.g., it also can control the amplitude. Since the amplitude term is also dependent upon power density and exposure duration, these variables can be used to normalize the amplitude while allowing the absorption coefficient to change.

Procedure Duration

In the evaluation of a proposed new therapy, it may be important to estimate the preferable procedure time and evaluate this estimate in the context of competing approaches and constraints specific to the clinical setting and patient acceptance. PDT is currently applied for the treatment of BE in the endoscopy setting and requires procedure times on the order of 20 minutes. For the exemplary conformal laser therapy technique, the procedure performance time may be estimated by 2 At/(πrv), where At is the treatment area, r is the laser spot radius, and v is the laser spot scan velocity. For an esophageal treatment length of 60 mm and an esophageal diameter of 20 mm.

According to the exemplary embodiment of the present invention, a combined system can be provided which may allow for a controlled laser excitation. In one exemplary embodiment, the exemplary system can be used endoscopically for conformal laser therapy capable of comprehensively treating epithelial lesions while minimizing collateral damage to adjacent tissues.

Exemplary System Design

According to the exemplary embodiment of the present invention, a system can be provided for performing conformal laser therapy of epithelial disease through a combination of monitoring and control. Since laser beams can easily be shaped and spatially scanned and since margins in the transverse plane (along the surface of the esophagus) are less critical, the primary challenge for achieving accurate control of laser therapy is in limiting and adjusting the depth of laser damage. Based on the modeling and analysis described above, it is possible to utilize laser wavelength and power and scanning speed to vary the depth of laser damage over a clinically significant range while not significantly altering the transverse extent of injury.

Exemplary Therapy Laser Arrangement

The laser wavelengths between approximately 1375 nm and 1430 nm can provide absorption lengths ranging from over 2 mm to less than 0.3 mm. Semiconductor lasers can operate in this spectral range. Since such lasers can be compact and environmentally stable, these laser can be effectively used in clinical applications. Materials suitable for this specific wavelength range, however, may not be standard. A less expensive alternative for the early testing phase of exemplary embodiments of the methods according to the present can be provided by a solid-state laser material, tetravalent chromium-doped YAG (Cr4+:YAG). For example, a tunability with this material over the spectral range of 1340 nm-1570 nm can be implemented (as described in publications 58 and 59 identified below). The exemplary design and construction of tunable solid-state lasers that operate in the near infrared spectral range are described in publications 60-65 identified below. An electromechanical shutter, external to the laser resonator, can be used to turn on/off the exemplary laser.

Exemplary Benchtop System

An exemplary embodiment of a benchtop optical system according to the present invention may be provided that can be similar to the systems shown in FIGS. 4 and 27 and described herein. For example, the OFDI sampling beam may be focused at the sample to a diameter of ~25 µm. The axial location of the focus can be determined using a standard z-scan technique, and may be registered within the OFDI cross-sectional image. The subsequent axial positioning of the samples within the OFDI image window may ensure a constant focus location for all samples. Data may be collected with the two beams fixed with respect to each other and while the sample is translated perpendicular to the laser beam axis.

Exemplary Positioning and Registration of Laser and OFDI beams

Figure 7:
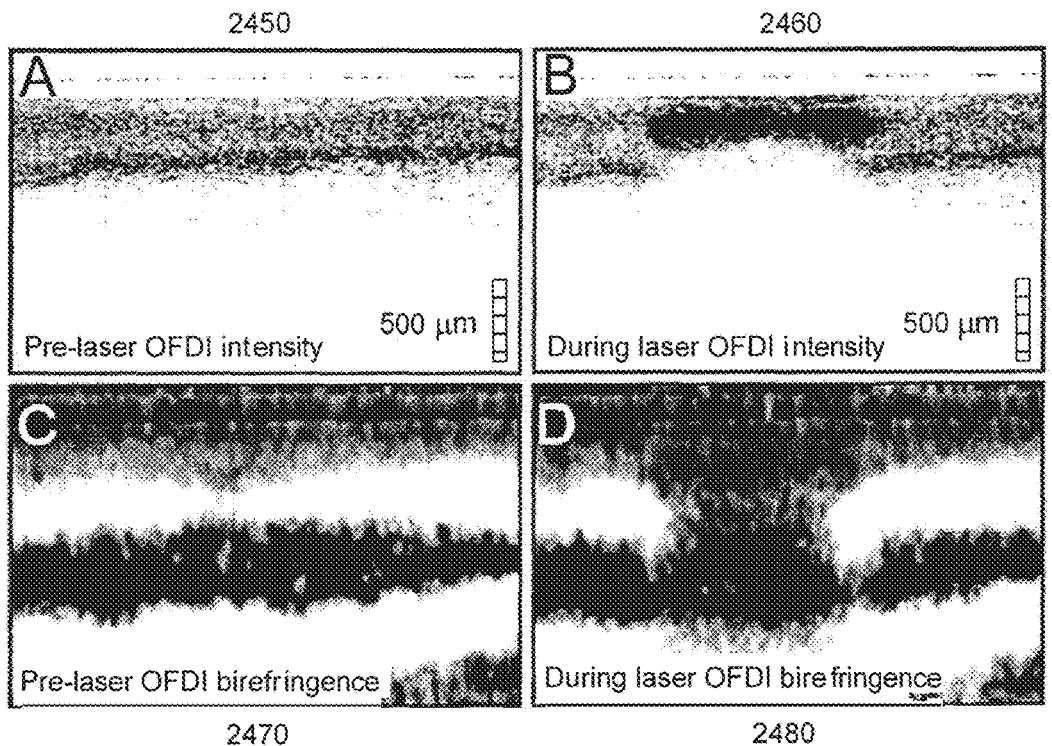
FIG. 7A is an exemplary pre-laser treatment OFDI image obtained using the exemplary embodiment of the present invention.
FIG. 7B is an exemplary pre-laser treatment birefringence image obtained using the exemplary embodiment of the present invention.
FIG. 7C is an exemplary post-laser treatment OFDI image obtained using the exemplary embodiment of the present invention.
FIG. 7D is an exemplary post-laser treatment birefringence image obtained using the exemplary embodiment of the present invention.

According to the exemplary embodiment of the present invention, the offset between the OFDI beam and the center of the laser spot is not critical for monitoring. OFDI data may be collected for various offsets (as depicted in FIG. 4) to determine the offset that yields the greatest indicated depth of thermal injury. This offset can then be used in all subsequent studies and may be registered as follows. A small, low-power, short-duration epithelial burn may be induced on the surface of the sample while the sample is held fixed (non-translating). As shown in FIG. 7, the increase in epithelial scattering can be readily observed in OFDI and is spatially localized as defined by the laser beam profile. Although not illustrated in FIG. 4, the OFDI beam can be relayed to the focusing lens by a pair of galvanometers that provide two-dimensional scanning. The galvanometers may be used to generate an en face OFDI image of the sample and the epithelial burn may appear as a circle of increased scattering. The galvanometers can then be positioned and fixed so that the OFDI beam is positioned with the desired offset (as schematically shown in FIG. 4).

Exemplary Wavelength Scaling

One of the purposes of this experiment is to test the exemplary technique and method of wavelength variation and power normalization according to the present invention for achieving clinically relevant variation in the depth of laser damage. Laser wavelength may be varied from about 1375 nm to 1405 nm in 2 nm steps with laser spot size and scanning speed held constant. For each wavelength, the laser power may be adjusted so that the product $P_d \oplus \mu_a$ in Eq. 1 can be maintained as constant. This should yield lines of constant width and with damage depth ranging from approximately 0.25 to 1.5 mm.

Exemplary Scanning Velocity Scaling

One exemplary embodiment according to the present invention for affecting therapeutic depth may include scaling the scan velocity. For example, the therapy beam scan speed can be varied from 1 mm/s to 5 mm/s. Slower scan speeds allow time for heat to conduct to deeper areas of the tissue, producing deeper therapy.

Exemplary Positioning and Registration of Laser and OFDI Beams

To ensure accurate therapeutic monitoring, the spatial relationship between the OFDI sampling beam and the laser spot can be controlled.

Exemplary Endoscopic Probe Designs

Figure 11:
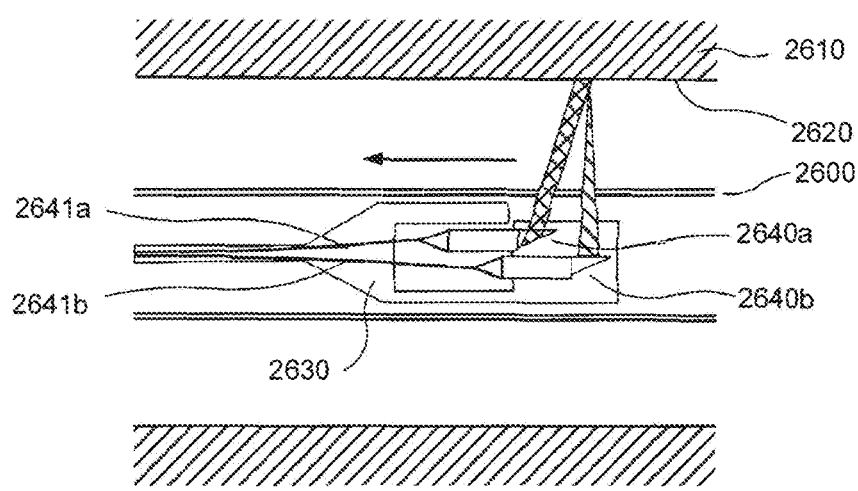
FIG. 11 is a schematic diagram of a two beam catheter probe in accordance with another exemplary embodiment of the present invention.

One exemplary embodiment of the present invention can include an endoscopic probe for comprehensive, volumetric imaging and simultaneous laser therapy, as shown in FIG. 11. For example, two beam relay optics 2640a and 2640b may be used, one of which conveys imaging light 2640b and the other therapy light 2640a. These relay optics are placed within a housing 2630 that is enclosed within a first transparent sheath 2600. A balloon centration mechanism (as described above) 2620 may be used to maintain a constant distance between the optical probe 2630 and the tissue surface 2610. Laser light and the OFDI beam may be delivered through separate optical fibers 2641a and 2641b. Each fiber may have its own relay optics to produce independently controllable spot sizes. A further exemplary embodiment of the present invention can include these relay optics designed to produce overlapping spots. The optical fibers and distal optics may be housed in a wound-wire drive shaft and placed inside a balloon-centering probe identical to the balloon sheaths.

Longitudinal scans can be activated using a computer controlled translation stage attached to the proximal end of the drive shaft. This exemplary arrangement may be the same as the arrangement which can be used for the pull-back esophageal imaging of our preliminary studies. A manual rotation of the drive shaft may be possible, as is automated rotation using an exemplary rotary coupler 2900 shown in FIG. 13. In one exemplary embodiment of the present invention, an endoscopic system may screen for disease over large fields-of-view, accurate monitoring of laser-tissue interaction, and precisely control laser therapy. One of the applications of such exemplary embodiment may be the identification and treatment of epithelial cancers and their precursors. In a further exemplary embodiment, the system can incorporate procedures and software modules than can directly link screening, monitoring, and control.

In yet another exemplary embodiment, the system may be used to generate a high-resolution, 3-dimensional map of the entire distal esophagus to facilitate therapeutic planning. Thereafter, the use may be presented with a 'live' cross-sectional image comprising three sections, as illustrated in FIG. 14. A right section 2700 of the image may be the tissue immediately ahead of the therapeutic lase, the center 2730 of the image may be the location of the laser with a marker 2740 designating the zone of therapy, and the left section 2710 of the image may be the tissue that has already been treated. Since the three beams may be continuously scanning, the tissue may appear to move from right to left as the image updates. The user (e.g., an endoscopist) may operate a control servo to start/stop the treatment and increase or decrease the depth of therapy. By viewing the zone of treatment 2710 and looking ahead to the untreated tissue 2700, the user may be able to steer and conform the region of laser therapy to the desired target.

Figure 12:
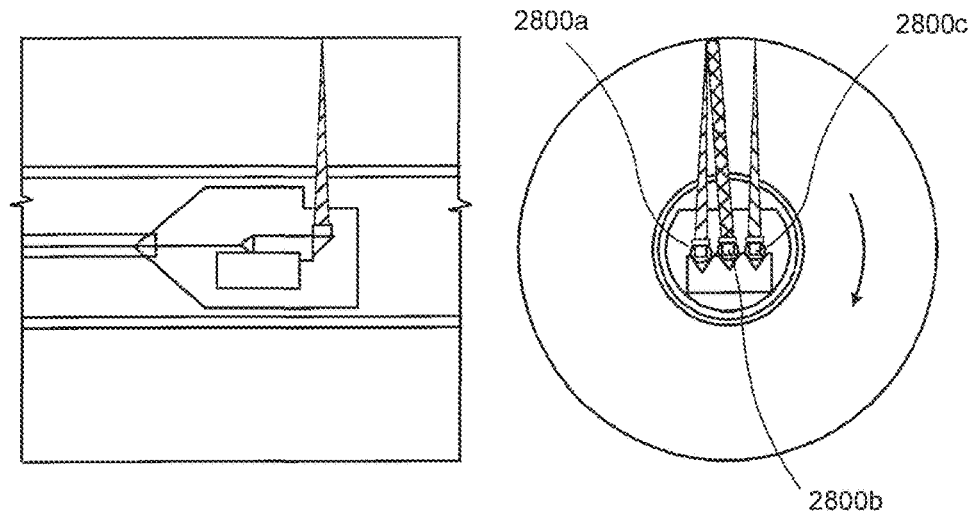
FIG. 12 is schematic side and front illustrations of a three beam catheter probe in accordance with yet another exemplary embodiment of the present invention.

An exemplary embodiment of the endoscopic probe for imaging, monitoring and laser therapy through a centering balloon according to the present invention is shown in FIG. 12. This exemplary probe can rotate to scan the esophagus circumferentially and may be longitudinally translated at a slower rate to define segments for therapy. This probe may include, e.g., three or more optical channels: a first channel 2800c for imaging the tissue prior to laser irradiation, a second channel 2800b for treatment, and a third channel 2800a for monitoring. Each optical fiber may be separately imaged transversely onto the esophageal wall through the balloon. The alignment of the resulting output beams may be such that, upon rotation in the clockwise direction, the imaging beam precedes the treatment beam sufficiently so that non-treated tissue may be sampled. The monitoring beam may be aligned to fall within the laser spot. Following initial alignment of the three beams, the optics may be bonded together with epoxy, and the alignment may be fixed.

Exemplary Rotary Junction

Figure 13:
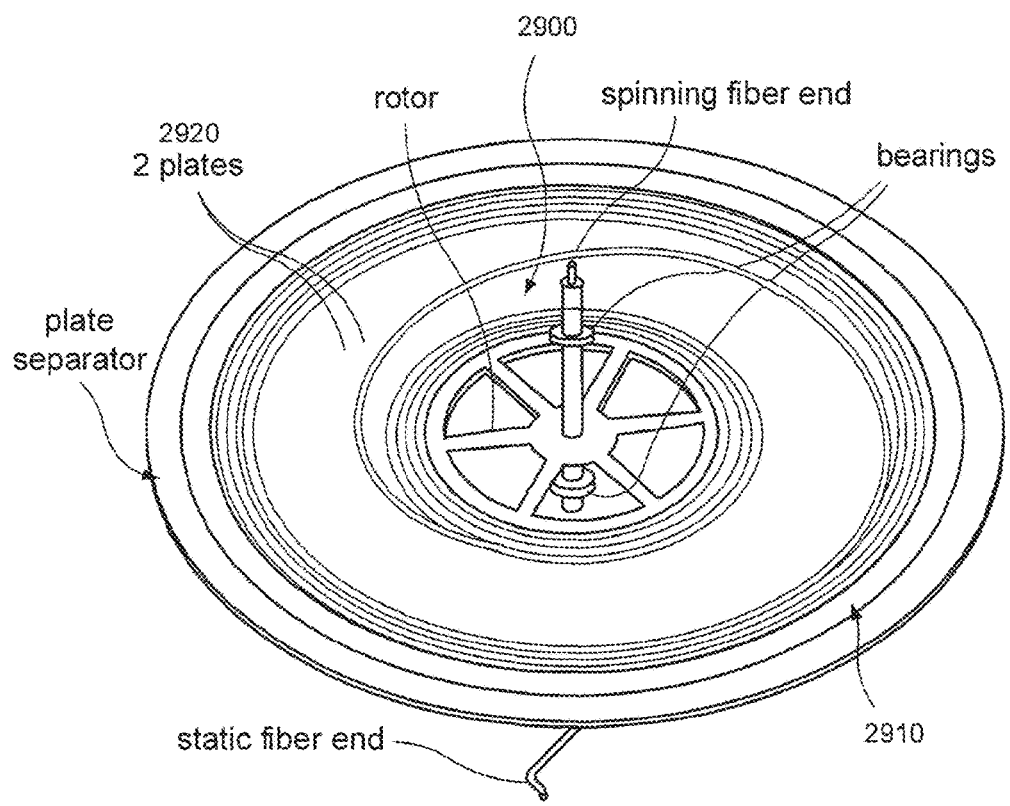
FIG. 13 is a perspective view of a watch-spring multi-channel optical rotary junction in accordance with an exemplary embodiment of the present invention.

An exemplary rotational coupler according to the present invention which can connect the three-channel catheter to the OFDI system is shown in FIG. 13, and can be referred to "watch-spring" rotary junction (since it can rely on two concentric spools). For example, as the inner spool 2900 rotates in one direction, optical fiber is wound from the outer spool 2910 onto the inner spool 2900. On reversing the direction, the fiber can unwind from the inner spool. Ribbon optical fiber may be used and two parallel plates 2920 with a gap matched to the ribbon width can ensure that the windings remain flat and do not bind. The plates may be sufficiently large so that up to, e.g., 100 rotations may be possible prior to requiring counter rotation. With a 1 mm laser spot, full treatment of 6 cm long esophageal segments may be 60 revolutions. A plate diameter of less than 10 cm can be used. In addition to accommodating three optical channels, this exemplary embodiment of the arrangement and system according to the present invention can avoid the loss and back-reflections that arise from air-gap couplers.

Exemplary High-Speed Acquisition and Processing

A further exemplary embodiment of the system and arrangement according to the present invention can utilize, e.g., a high-speed imaging system. The exemplary embodiment of the digital acquisition and processing system can be based on VME-bus hardware for acquiring, processing and storing the OFDI signals in real-time. The exemplary components of such exemplary system and arrangement may comprise a VME chassis containing high-speed digitizers residing on a single-board computer and fiber-optic links to a RAID storage array. This exemplary system and arrangement can be controlled via a host processor (e.g., a personal computer). The analog OFDI signals may be digitized using wideband receivers (e.g., 12 bit, 210 MS/s) with integrated field-programmable-gate-array (FPGA) processors. Processing power, resident on the acquisition board, may be importance since the raw data rate may be 800 MB/s for the two polarization channels of the OFDI system. The FPGA processor can be configured or programmed to transform each polarization channel from the frequency-domain to a 1024-element array representing reflectivity versus depth (one A-line). This data can be passed to the single-board computer for subsequent processing and for combining the two channels prior to transferring the final data to a RAID array of hard drives. The final data storage rate may be, e.g., 400 MB/s. By striping the data across multiple hard drives, this data rate can be continuously sustained.

Software on a processing arrangement in accordance with an exemplary embodiment of the present invention can permit a user control over the exemplary system, and may enable a display of the images at a down-sampled rate in real-time. For example, the exemplary system can be used in two exemplary modes: a burst mode at full data rate, and continuous mode at half data rate. The exemplary endoscopic system and arrangement can include the components and software described above, and additional procedures (e.g., software) can be provided to program both the FPGA processor and single-board computer to facilitate the computations of phase-shift, birefringence, speckle, and Doppler signals in real-time. The combined computational capacity of the Vertex 4 Pro FPGA and quad G4 single-board computers may be ample for displaying the monitoring signal in real-time.

Exemplary Laser

Using Eq. 1, the spot size while maintaining a constant scan velocity can be doubled by using a 4-fold increase in the laser power in order to maintain a constant temperature distribution in the tissue. Doubling the scan velocity at a constant spot size should use a doubled laser power. One exemplary embodiment of a laser arrangement in accordance with the present invention can utilize a single-emitter semiconductor laser diode. Previous devices have provided more than 3 W of laser power over this spectral range using a simple external cavity design including a diffraction grating for wavelength control. The laser power and wavelength may be controlled via the host processing arrangement of the OFDI system based on an analog signal from a potentiometer. The potentiometer may be a hand-held dial that the user (e.g., an endoscopist) may use to increase or decrease the depth of laser damage.

Exemplary User Interface

The exemplary embodiment of the system and method according to the present invention can provide a user interface to the operator that includes a cross-sectional image of the tissue. The image may be continuously updated and may include views of treated and upcoming, untreated tissue as well as a designation for the zone of laser treatment as determined by the monitoring procedures. The user interface may be programmed on the host processing arrangement, and can use computational results from the FPGA processor and single-board computer. Images and laser parameters may be archived to the RAID array.

In one further exemplary embodiment of the present invention, the imaging system/arrangement 100 can be connected to a three-fiber probe using an optical switch 115 as shown in a block diagram of FIG. 15. The exemplary probe, such as that described above with reference to FIG. 12, can include two imaging fibers and one therapy fiber. The switch 115 can alternately couple imaging light to one of the two imaging fibers 120a, 120b which can be used to acquire re-therapy images and, e.g., during-therapy imaging. A therapeutic light source 105 may connect directly to the therapy fiber 125c. The fibers can be connected to the catheter 130, which can be, e.g., the exemplary catheter shown FIG. 12. A signal from the imaging system 100 can control the state of the optical switch 115.

In yet another exemplary embodiment according to the present invention shown in FIG. 16, the exemplary imaging system/arrangement 200 can be coupled to an exemplary three-port catheter such as one shown in FIG. 12 via an optical splitter 215 that can couple light to both of two imaging fibers 220a, 220b. This exemplary imaging system can separate the image signal from each using path-length encoding techniques. To generate the differential path length, an optical delay 235 may be placed in one fiber 220b or multiple fibers. The therapeutic light source 205 can be coupled directly or indirectly to the therapy fiber 225c of the catheter.

In still another exemplary embodiment of the exemplary imaging system/arrangement 800 according to the present invention shown in FIG. 17, light may be combined with the therapy source 805 using a single wavelength-division multiplexer 810. The combined light may be coupled to a single fiber rotary coupler, and then to an exemplary single fiber catheter such as the catheter shown in FIG. 21.

In a further exemplary embodiment of the imaging system/arrangement 900 according to the present invention shown in FIG. 18, light may be combined with the therapy light 905 using a cladding mode coupler that couples the imaging system 900 light from the single mode fiber 901 to the single mode core of a dual-clad fiber 911 and the therapy light from a multimode fiber 906 to the cladding mode of a dual-clad fiber 911.

FIG. 19 shows exemplary connections between a system 400 with three output fibers 405a, 405b, 405c, such as one shown schematically in, e.g., FIGS. 15 and 16, and a three-port catheter 415, such as one shown in FIG. 12 via a multi-channel rotary coupler 410, such as one shown in FIG. 13.

FIG. 20 shows a schematic diagram of an exemplary system 300 according to the present invention in which a single fiber 305 containing both the imaging light and therapy light may be coupled to a single-channel rotary coupler 310. For example, after the rotary coupler 310, the light can be divided by a wavelength-division multiplexer (WDM) 330 that separates the imaging light onto a first fiber 332 and the therapy light onto a second fiber 331. The imaging light may further be separated using an optical splitter 335 that greats two imaging ports 336a and 336b. The fibers 31, 336a, 336b can be connected to a three-port catheter 325 design such as that shown in FIG. 12. The catheter section 320 may be flexible allowing endoscopic insertion and the section containing a WDM 330 and a splitter 335 can be enclosed within a rigid tube 315 to protect these components.

Figure 21:
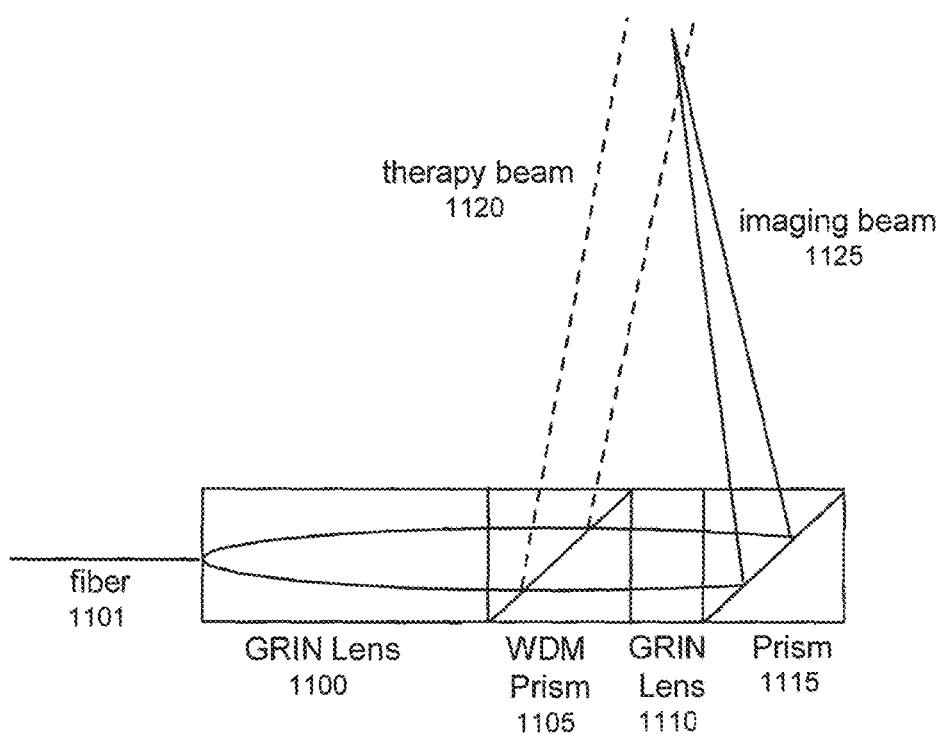
FIG. 21 is a schematic diagram and usage of a two-beam in-line catheter probe in accordance with an exemplary embodiment of the present invention.

FIG. 21 shows a side view of an exemplary embodiment of a distal optics arrangement according to the present invention that may create a single imaging beam 1125 and a separate therapy beam 1120 from a single-mode fiber 1101. For example, the light from the fiber containing both imaging and therapy light can first be focused by a first GRIN lens 1100. The light is then passed into a wavelength-division multiplexing prism 1105 that can direct the therapy light wavelengths upward to create the therapy beam 1120, and transmits the imaging light wavelengths to a second GRIN lens 1110, which can alternately focus the imaging light and directs it to a final prism 1115 that directs the imaging beam 1125 upward. The angle of the prisms 1105 and 1115 may be such that the beams are made to overlap at the appropriate distance from the device.

Figure 22:
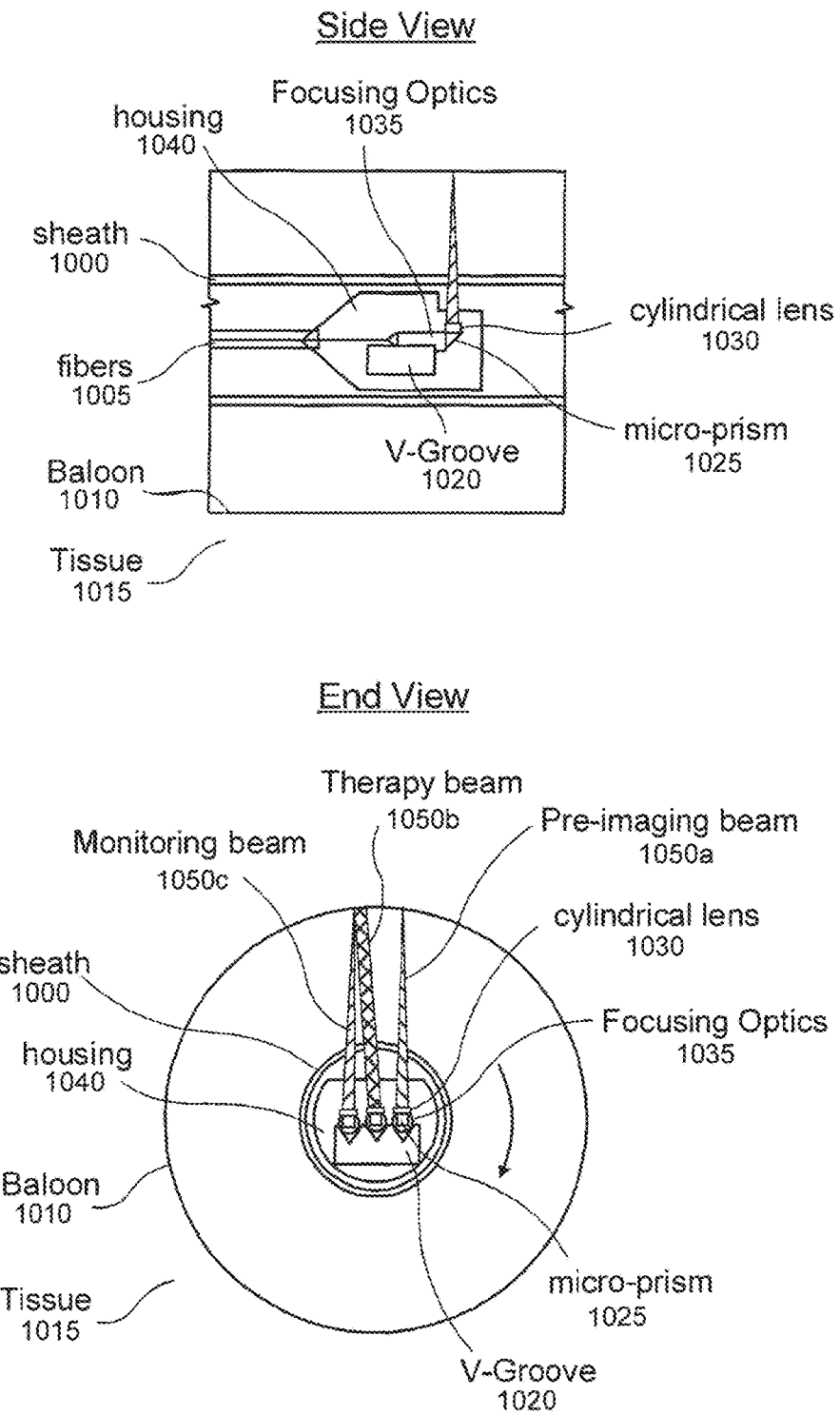
FIG. 22 are front and side illustrations of a three-beam catheter probe and balloon catheter in accordance with an exemplary embodiment of the present invention.

FIG. 22 shows side and front views of an exemplary embodiment of a three-port catheter in accordance with the present invention. The exemplary catheter can include three fibers 1005 that connect to three sets of focusing optics 1035 contained in a V-groove 1020 inside a housing 1040. The focusing optics can provide beam focusing. Micro-prisms 1025 can redirect the optical beam upward through a cylindrical lens 1030 that corrects for astigmatism induced by the transparent sheath 1000. A balloon 1010 centration mechanism may be used to maintain centering of the optics 1035 within the luminal tissue 1015. In the end-view, the monitoring beam 1050c, therapy beam 1050b, and pre-imaging beam 1050a can be seen. The housing 1040 can be adapted to rotate by a multichannel rotary coupler such as one shown in FIG. 13.

Figure 23:
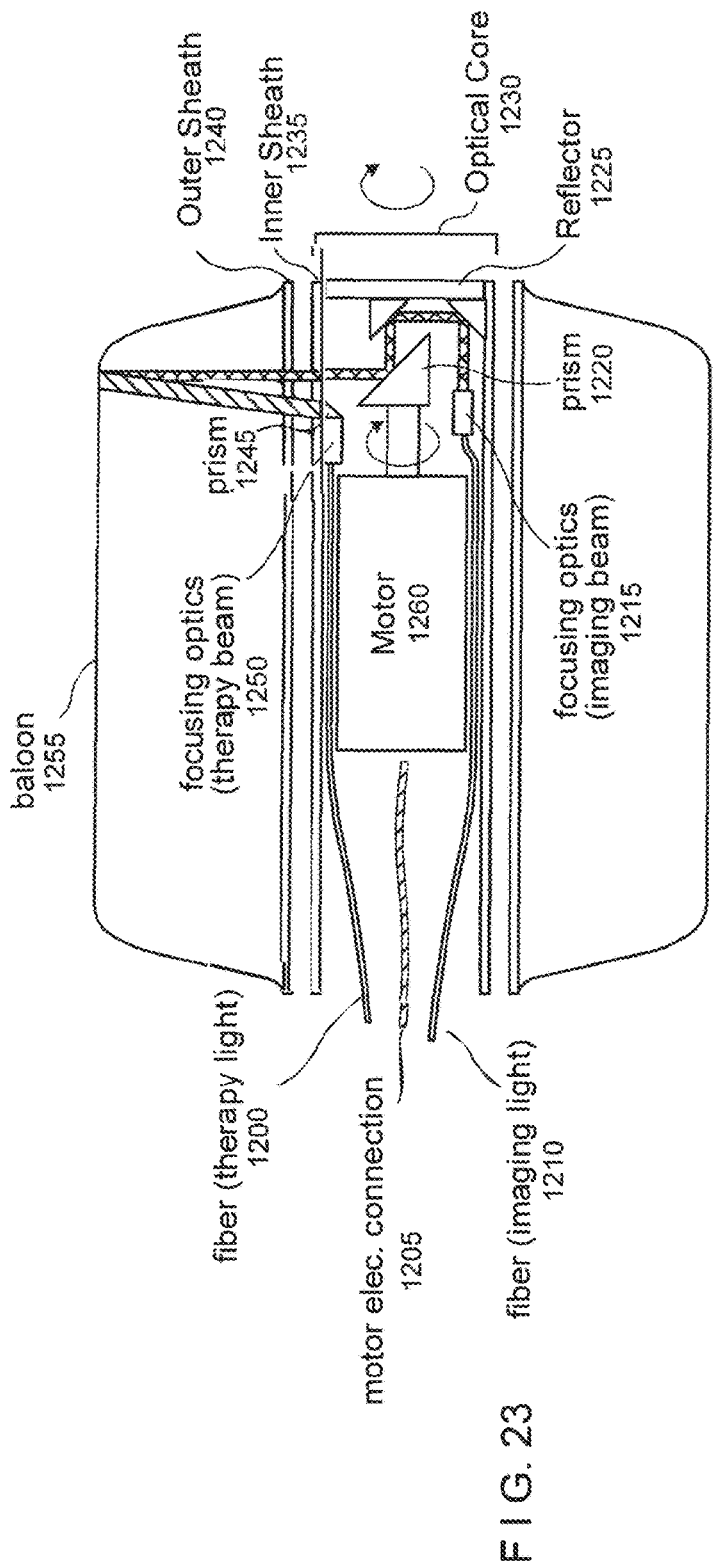
FIG. 23 is a side view of a micro-motor-based arrangement capable of generating a slowly rotatable therapy beam and fast scanning imaging beam in accordance with an exemplary embodiment of the present invention.

FIG. 23 shows a side view of an exemplary embodiment of a catheter in accordance with the present invention which can utilize a miniature motor 1260 to achieve rotation of the imaging beam. For example, the motor 1260 can be enclosed within a transparent sheath 1235. The rotation of the motor shaft can rotate a prism 1220. The imaging light can be coupled to the distal optics via a fiber 1210, where the light can be focused by focusing optics 1215, and reflected onto the prism 1220 by a reflector 1225. The rotation of the prism 1220 sweeps the imaging beam circumferentially. The motor electrical connections 1205 can be achieved through the same lumen as the fiber 1210. The therapy light is coupled to the distal optics on fiber 1200. This therapy light may be focused using focusing optics 1250, and directed sideways by prism 1245 at a fixed rotational angle relative to the inner sheath 1235. The imaging beam thus sweeps through the fixed therapy spot. The translation of the therapy spot is achieved by rotation of the entire inner sheath 1235 within the outer sheath 1240. This exemplary rotation can be achieved through the use of a multi-channel rotary coupler such as a coupler shown in FIG. 13. The catheter can use a balloon 1255 for centration of an optical core 1230.

Figure 24:
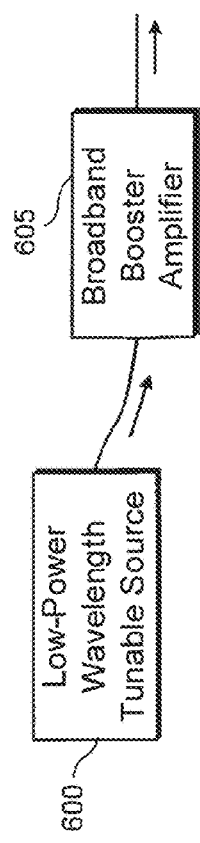
FIG. 24 is a block diagram of a therapy source incorporating a low power tunable source followed by a broadband booster amplifier in accordance with an exemplary embodiment of the present invention.

FIG. 24 shows a block diagram of an exemplary embodiment of a laser therapy source according to the present invention with wavelength tunability utilizing a low power wavelength tunable source 600, followed by a broadband booster amplifier 605 to increase the optical power.

Figure 25:
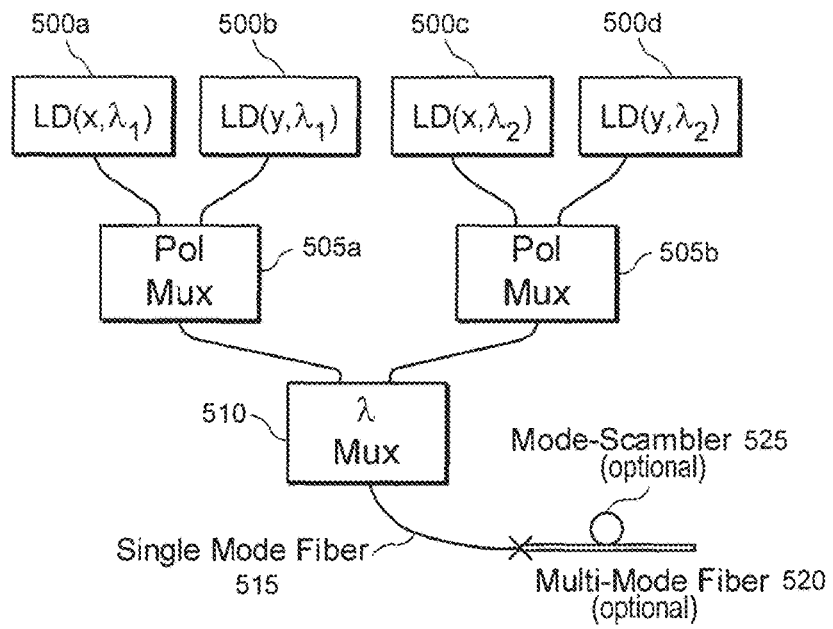
FIG. 25 is a block diagram of a therapy source incorporating multiple laser diodes (LDs) at difference wavelengths and polarizations in accordance with another exemplary embodiment of the present invention.

FIG. 25 shows a block and functional diagram of an exemplary embodiment of a laser therapy source incorporating multiple laser diodes 500a, 500b, 500c, 500d at difference wavelengths and polarizations, and the exemplary procedure to implement such arrangement. For example, the light can be combined by the polarization multiplexers 505a, 505b and wavelength division multiplexers 510 to a single mode fiber 515. Optionally, the light can be coupled to a multimode fiber 520. A fast mode scrambler 525 can be used to scramble the transverse mode pattern output from the multimode fiber at a fast rate. Other source arrangements which can output light on a single mode fiber can use a similar design to couple light to a multimode fiber.

Figure 26:
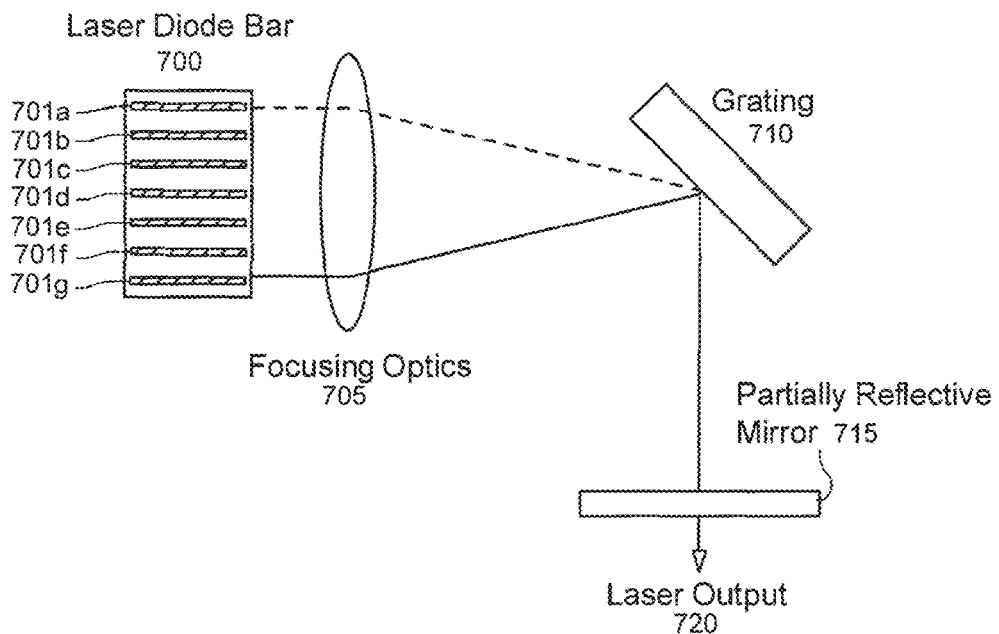
FIG. 26 is an illustration of a wavelength-tunable therapy source incorporating a laser diode bar and results generated thereby in accordance with an exemplary embodiment of the present invention.

FIG. 26 shows an exemplary embodiment of a therapy light source and use thereof according to the present invention. For example, a laser diode bar 700 can be used with multiple wavelengths 701*a-g*. Each waveguide can be coupled to a free-space laser cavity through a lens apparatus 705 and a grating 710 and a partially reflecting end mirror 715. Because of the wavelength dispersion of the grating, the laser formed by each waveguide lases at a different wavelength. Thus, by adjusting the drive current to each of the waveguides 701*a-g*, the laser output 720 power and spectral shape can be adjusted.

Figure 28:
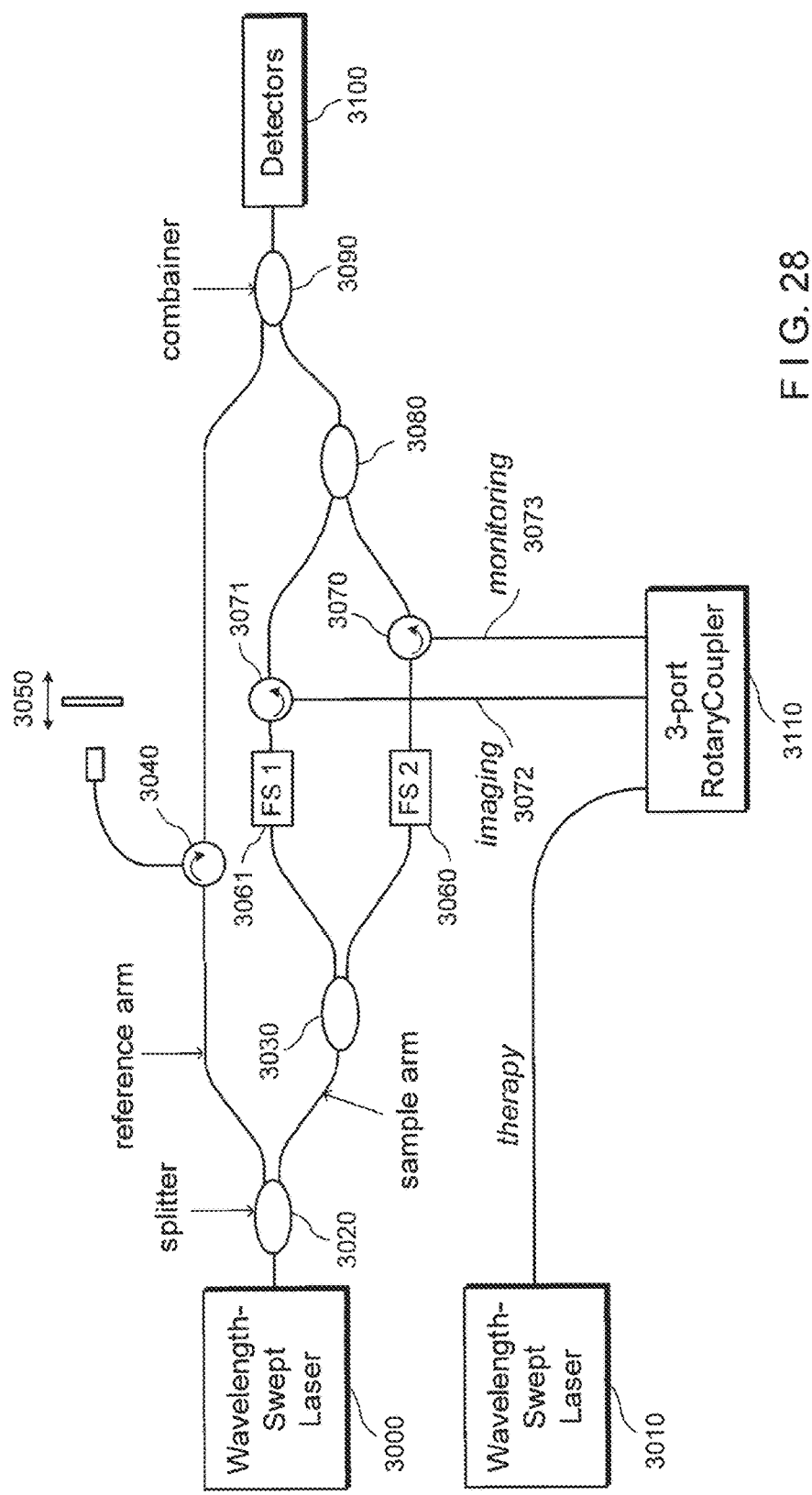
FIG. 28 is a schematic diagram of a further exemplary embodiment of the OFDI system according to the present invention which can be used to detect both the imaging and monitoring signals via acousto-optic frequency shifters.

In a further exemplary embodiment according to the present invention, a single OFDI system can be modified to facilitate a detection of both the imaging and monitoring signals through the use of acousto-optic frequency shifters as shown in FIG. 28. For example, a wavelength swept laser source 3000 can be separated by a first splitter 3020 to produce a sample arm path and reference arm path. The sample arm path is further separated by a second splitter 3030, with a first output of this splitter being directed to a first frequency shifter 3061 and a second output being directed to a second frequency shifter 3060. Each of the frequency shifters can be driven with a separate frequency. The light from the first frequency shifter 3061 can be coupled through an optical circulator 3071 to the imaging fiber 3072 of a three-fiber rotary coupler 3110 like that shown in FIG. 13. The light from the second frequency shifter 3060 may be coupled through a circulator 3070 to a monitoring fiber 3073 of the same rotary coupler.

A separate therapy laser 3010 can be coupled to the third therapy fiber. The returned light on the imaging fiber 3072 and monitoring fiber 3073 may be recombined at an optical combiner 2080, and mixed with the reference arm light at a second combiner 3090 with the output directed to a set of detectors 3100. Due to the frequency shifters, the interference signal due to the imaging light and the interference signal due to the monitoring light are encoded at separate carrier frequencies, e.g., using a computer 3095 which is part of an exemplary imaging system shown in FIGS. 15-20, and can be separated through conventional frequency domain techniques.

FIG. 29A shows a flow diagram of an exemplary embodiment of a method for obtaining information associated with at least one portion of a sample according to the present invention. For example, a temperature change can be caused in the portion of the sample in step 3105. At least one first electro-magnetic radiation can be forwarded to a section near or in the portion of the sample in step 3110. A deformation of the section can be identified at a plurality of depths as a function of (i) a phase of at least one second electro-magnetic radiation provided from the section, and/or (ii) a rate of change of the phase and/or an amplitude of the second electro-magnetic radiation in step 3120.

FIG. 29B shows a flow diagram of another exemplary embodiment of the method for controlling a temperature distribution in the sample according to the present invention. For example, an electromagnetic radiation can be provided to the section in the sample at a particular wavelength in step 3130. The temperature distribution can be controlled by modifying the particular wavelength of the electromagnetic radiation when the electromagnetic radiation can be provided to the section in step 3140.

FIG. 29C illustrates a flow diagram of yet another exemplary embodiment of the method for applying a laser radiation to at least one portion of a biological structure according to the present invention. For example, a beam of the laser radiation can be provided to the portion in step 3150, whereas a cross-sectional area of the beam is at most about $\frac{1}{10}^{th}$ of an entire area of the at least one portion. In step 3160, the beam can be applied to the portion (I) based on a predetermined pattern, (II) while modulating a wavelength of the laser radiation, and/or (III) while monitoring a depth of the application of the laser radiation.

EXEMPLARY REFERENCES

1. Devesa S S, Blot W J and Fraumeni J F, Jr. Changing patterns in the incidence of esophageal and gastric carcinoma in the United States. Cancer 1998; 83:2049-2053.
2. Barr H, Stone N and Rembacken B. Endoscopic therapy for Barrett's oesophagus. Gut 2005; 54:875-884.
3. Johnston M H. Technology insight: ablative techniques for Barrett's esophagus—current and emerging trends. Nature Clinical Practice Gastroenterology & Hepatology 2005; 2:323-330.
4. Falk G W, Chittajallu R, Goldblum J R, Biscotti C V, Geisinger K R, Petras R E, Birgisson S, Rice T W and Richter J E. Surveillance of patients with Barrett's esophagus for dysplasia and cancer with balloon cytology. Gastroenterology 1997; 112:1787-1797.
5. Spechler S J. Barrett's esophagus: should we brush off this ballooning problem? Gastroenterology 1997; 112:2138-2142.
6. Kubba A K, Poole N A and Watson A. Role of p 53 assessment in management of Barrett's esophagus. Dig Dis Sci 1999; 44:659-667.
7. Reid B J. p 53 and neoplastic progression in Barrett's esophagus. Am J Gastroenterol 2001; 96:1321-1323.
8. Sharma P, Weston A P, Topalovski M, Cheman R, Bhattacharyya A, Sampliner R E. Magnification chromoendoscopy for the detection of intestinal metaplasia and dysplasia in Barrett's oesophagus, GUT 2003; 52: 24-27.
9. Kuipers E J and Haringsma J. Diagnostic and therapeutic endoscopy. Journal of Surgical Oncology 2005; 92:203-209.
10. Georgakoudi I, Jacobson B C, Van Dam J, Backman V, Wallace M B, Muller M G, Zhang Q, Badizadegan K, Sun D, Thomas G A, Perelman L T and Feld M S. Fluorescence, reflectance, and light-scattering spectroscopy for evaluating dysplasia in patients with Barrett's esophagus. Gastroenterology 2001; 120:1620-1629.
11. Adrain A L, Ter H C, Cassidy M J, Schiano T D, Liu J B and Miller L S. High-resolution endoluminal sonography is a sensitive modality for the identification of Barrett's metaplasia. Gastrointest Endosc 1997; 46:147-151.
12. Canto M I. Vital staining and Barrett's esophagus. Gastrointest Endosc 1999; 49:S12-16.
13. Huang D, Swanson E A, Lin C P, Schuman J S, Stinson W G, Chang W, Hee M R, Flotte T, Gregory K, Puliafito C A and Fujimoto J G. Optical coherence tomography. Science 1991; 254:1178-1181.
14. Teamey G J, Brezinski M E, Bouma B E, Boppart S A, Pitvis C, Southern J F and Fujimoto J G. In vivo endoscopic optical biopsy with optical coherence tomography. Science 1997; 276:2037-2039.
15. Evans J A, Poneros J M, Bouma B E, Bressner J, Halpern E F, Shishkov M, Lauwers G Y, Mino-Kenudson M, Nishioka N S and Tearney G J. Optical Coherence Tomography to Identify Intramucosal Carcinoma and High Grade Dysplasia in Barrett's Esophagus. Clinical Gastroenterology and Hepatology 2005; 4:38-43.
16. Poneros J M, Brand S, Bouma B E, Tearney G J, Compton C C and Nishioka N S. Diagnosis of Specialized Intestinal Metaplasia by Optical Coherence Tomography. Gastroenterology 2001; 120:7-12.
17. Brand S, Poneros J M, Bouma B E, Tearney G J, Compton C C and Nishioka N S. Optical Coherent Tomography in the Gastrointestinal Tract. Endoscopy 2000; 32:796-803.
18. de Boer J F, Cense B, Park B H, Pierce M C, Tearney G J and Bouma B E. Improved signal-to-noise ratio in spectral-domain compared with time-domain optical coherence tomography. Optics Letters 2003; 28:2067-2069.
19. Choma M A, Sarunic M V, Changhuei Y and Izatt J A. Sensitivity advantage of swept source and Fourier domain optical coherence tomography. Optics Express 2003; 11:2183-2189.
20. Leitgeb R, Hitzenberger C K and Fercher A F. Performance of Fourier domain vs. time domain optical coherence tomography. Optics Express 2003; 11:889-894.
21. Yun S H, Tearney G J, de Boer J F, Iftimia N and Bouma B E. High-speed optical frequency-domain imaging. Optics Express 2003; 11:2953-2963.
22. Yun S H, Boudoux C, Tearney G J and Bouma B E. High-speed wavelength-swept semiconductor laser with a polygon-scanner-based wavelength filter. Optics Letters 2003; 28:1981-1983.
23. Oh W Y, Yun S H, Tearney G J and Bouma B E. 115 kHz tuning repetition rate ultrahigh-speed wavelength-swept semiconductor laser. Optics Letters 2005; 30:3159-3161.
24. Vakoc B J, Yun S H, de Boer J F, Tearney G J and Bouma B E. Phase-resolved optical frequency domain imaging. Optics Express 2005; 13:5483-5493.
25. Brown S B, Brown E A and Walker I. The present and future role of photodynamic therapy in cancer treatment. Lancet Oncol 2004; 5:497-508.
26. van den Boogert J, van Hillegersberg R, Siersema P D, de Bruin R W and Tilanus H W. Endoscopic ablation therapy for Barrett's esophagus with high-grade dysplasia: a review. Am J Gastroenterol 1999; 94:1153-1160.
27. Sampliner R E, Fennerty B and Garewal H S. Reversal of Barrett's esophagus with acid suppression and multipolar electrocoagulation: preliminary results. Gastrointest Endosc 1996; 44:532-535.
28. Sampliner R E. Endoscopic ablative therapy for Barrett's esophagus: current status. Gastrointest Endosc 2004; 59:66-69.
29. Soetikno R M, Gotoda T, Nakanishi Y and Soehendra N. Endoscopic mucosal resection. Gastrointest Endosc 2003; 57:567-579.
30. Ganz R A, Utley D S, Stem R A, Jackson J, Batts K P and Termin P. Complete ablation of esophageal epithelium with a balloon-based bipolar electrode: a phased evaluation in the porcine and in the human esophagus. Gastrointest Endosc 2004; 60:1002-1010.
31. Mark H. Johnston, Brooks D. Cash, Cathy A. Dykes, Halisha S. Mays and Lavonne R. Johnston Cryoablation of Dysplasia in Barrett's Esophagus (BE) and Early Stage Esophageal Cancer. Gastrointest Endosc 2006; 63: AB223.
32. Overholt B F, Panjehpour M and Haydek J M. Photodynamic therapy for Barrett's esophagus: follow-up in 100 patients. Gastrointest Endosc 1999; 49:1-7.
33. Vogel A and Venugopalan V. Mechanisms of pulsed laser ablation of biological tissues. Chemical Reviews 2003; 103:2079-2079.
34. McKenzie A L. Physics of thermal processes in laser-tissue interactions. Physics in Medicine & Biology 1990; 35:1175-1209.
35. Anderson R R and Parrish J A. Selective photothermolysis: precise microsurgery by selective absorption of pulsed radiation. Science 1983; 220:524-527.
36. Jacques S L. Role of tissue optics and pulse duration on tissue effects during high-power laser irradiation. Applied Optics 1993; 32:2447-2454.
37. Nahen K and Vogel A. Investigations on acoustic on-line monitoring of IR laser ablation of burned skin. Lasers in Surgery & Medicine 1999; 25:69-78.
38. Jerath M R, Kaisig D, Rylander H G, 3rd and Welch A J. Calibrated real-time control of lesion size based on reflectance images. Applied Optics 1993; 32:1200-1209.
39. Jerath M R, Gardner C M, Rylander H G, 3rd and Welch A J. Dynamic optical property changes: implications for reflectance feedback control of photocoagulation. Journal of Photochemistry & Photobiology B—Biology 1992; 16:113-126.
40. Deckelbaum L I. Coronary laser angioplasty. Lasers in Surgery & Medicine 1994; 14:101-110.
41. Kim B M, Feit M D, Rubenchik A M, Mammini B M and Da Silva L B. Optical feedback signal for ultra short laser pulse ablation of tissue. Applied Surface Science 1998; 127-129:857-862.
42. Brinkmann R, Hansen C, Mohrenstecher D, Scheu M and Birngruber R. Analysis of cavitation dynamics during pulsed laser tissue ablation by optical on-line monitoring. Selected Topics in Quantum Electronics, IEEE Journal of 1996; 2:826.
43. Whelan W M, Davidson S R H, Chin L C L and Vitkin I A. A Novel Strategy For Monitoring Laser Thermal Therapy Based on Changes in Optothermal Properties of Heated Tissues. International Journal of Thermophysics 2005; 26:233-241.
44. Boppart S A, Herrmann J, Pitris C, Stamper D L, Brezinski M E and Fujimoto J G. High-resolution optical coherence tomography-guided laser ablation of surgical tissue. Journal of Surgical Research 1999; 82:275-284.
45. Thomsen S L, Jacques S L and Flock S T. Microscopic correlates of macroscopic optical property changes during thermal coagulation of myocardium. Proceedings of the SPIE 1990; 1202:2-11.
46. Maitland D J and Walsh J T, Jr. Quantitative measurements of linear birefringence during heating of native collagen. Lasers Surg Med 1997; 20:310-318.
47. Kimel S, Svaasand L O, Hammer-Wilson M, Schell M J, Milner T E, Nelson J S and Berns M W. Differential vascular response to laser photothermolysis. Journal of Investigative Dermatology 1994; 103:693-700.
48. Khan M H, Sink R K, Manstein D, Eimerl D and Anderson R R. Intradermally focused infrared laser pulses: Thermal effects at defined tissue depths. Lasers in Surgery and Medicine 2005; 36:270-280.
49. Neumann R A, Knobler R M, Pieczkowski F and Gebhart W. Enzyme histochemical analysis of cell viability after argon laser-induced coagulation necrosis of the skin. Journal of the American Academy of Dermatology 1991; 25:991-998.
50. Nadkarni S, Helg T, Bouma B E, Chan R C, Minsky M S, Chau A H, Motz J, Houser S L and Tearney G J. Characterization of atherosclerotic plaques by laser speckle analysis. Circulation 2005; 112:885-892.

51. Zimnyakov D A, Agafonov D N, Sviridov A P, Omel'chenko A I, Kuznetsova L V and Bagratashvili V N. Speckle-contrast monitoring of tissue thermal modification. Appl Opt 2002; 41:5989-5996.
52. Pierce M C, Sheridan R L, Park B H, Cense B and de Boer J F. Collagen denaturation can be quantified in burned human skin using polarization-sensitive optical coherence tomography. Burns 2004; 30:511-517.
53. de Boer J F, Milner T E, van Gemert M J C and Nelson J S. Two-dimensional birefringence imaging in biological tissue using polarization sensitive optical coherence tomography. Optics Letters 1997; 22:934-936.
54. Morelli J G, Tan O T, Garden J, Margolis R, Seki Y, Boll J, Carney J M, Anderson R R, Furumoto H and Parrish J A. Tunable dye laser (577 nm) treatment of port wine stains. Lasers Surg Med 1986; 6:94-99.
55. Chen Z P, Milner T E, Dave D and Nelson J S. Optical Doppler tomographic imaging of fluid flow velocity in highly scattering media. Optics Letters 1997; 22:64-66.
56. Izatt J A, Kulkarni M D, Yazdanfar S, Barton J K and Welch A J. In vivo bidirectional color Doppler flow imaging of picoliter blood volumes using optical coherence tomography. Optics Letters 1997; 22:1439.
57. Barton J K, Welch A J and Izatt J A. Investigating pulsed dye laser-blood vessel interaction with color Doppler optical coherence tomography. Optics Express 1998; 3:251-256.
58. French P M W, Rizvi N H, Taylor J R and Shestakov A V. Continuous-wave mode-locked Cr4+:YAG laser. Optics Letters 1993; 18:39-41.
59. Sennaroglu A, Pollock C R and Nathel H. Efficient continuous-wave chromium-doped YAG laser. Journal of the Optical Society of America B 1995; 12:930-937.
60. Bouma B, Gouveia-Neto A, Izatt J A, Russell J, Sierra R, Keller U and Fujimoto J G. Hybrid mode locking of a flash-lamp-pumped Ti:Al$_2$O$_3$ laser. Optics Letters 1994; 19:1858-1860.
61. Bouma B, Tearney G J, Boppart S A, Hee M R, Brezinski M E and Fujimoto J G. High-resolution optical coherence tomographic imaging using a mode-locked Ti:Al$_2$O$_3$ laser source. Optics Letters 1995; 20:1486-1488.
62. Bouma B E and Fujimoto J G. Compact Kerr-lens mode-locked resonators. Optics Letters 1996; 21:134-136.
63. Bouma B E, Nelson L E, Teamey G J, Jones D J, Brezinski M E and Fujimoto J G. Optical coherence tomographic imaging of human tissue at 1.55 µm and 1.81 µm using Er and Tm-doped fiber sources. Journal of Biomedical Optics 1998; 3:76-79.
64. Bouma B E, Ramaswamy-Paye M and Fujimoto J G. Compact resonator designs for mode-locked solid-state lasers. Applied Physics B (Lasers and Optics) 1997; 65:213-220.
65. Bouma B E, Tearney G J, Bilinsky I P, Golubovic B and Fujimoto J G. Self-phase-modulated Kerr-lens mode-locked Cr:forsterite laser source for optical coherence tomography. Optics Letters 1996; 21:1839-1841.

The foregoing merely illustrates the principles of the invention. Various modifications and alterations to the described embodiments will be apparent to those skilled in the art in view of the teachings herein. Indeed, the arrangements, systems and methods according to the exemplary embodiments of the present invention can be used with any OCT system, OFDI system, spectral domain OCT (SD-OCT) system or other imaging systems, and for example with those described in International Patent Application PCT/US2004/029148, filed Sep. 8, 2004, U.S. patent application Ser. No. 11/266,779, filed Nov. 2, 2005, and U.S. patent application Ser. No. 10/501,276, filed Jul. 9, 2004, the disclosures of which are incorporated by reference herein in their entireties. It will thus be appreciated that those skilled in the art will be able to devise numerous systems, arrangements and methods which, although not explicitly shown or described herein, embody the principles of the invention and are thus within the spirit and scope of the present invention. In addition, to the extent that the prior art knowledge has not been explicitly incorporated by reference herein above, it is explicitly being incorporated herein in its entirety. All publications referenced herein above are incorporated herein by reference in their entireties.

What is claimed is:

1. A process for applying a laser radiation to at least one portion of a biological structure, comprising:
   a) providing a beam of the laser radiation to the at least one portion, wherein a cross-sectional area of the beam is at most about 1/10th of an entire area of the at least one portion;
   b) applying the beam to the at least one portion (i) while modulating a wavelength of the laser radiation and (ii) while monitoring a depth of the application of the laser radiation;
   c) receiving at least one return radiation from the at least one portion;
   d) determining speckle information related to the at least one return radiation;
   e) determining a laser damage depth within the biological structure based on the speckle information; and
   f) adjusting a penetration depth of the beam by changing the wavelength of the laser radiation.

2. The process according to claim 1, wherein the laser radiation is provided to the at least one portion of the biological structure at the wavelength; and further comprising:
   g) during step (a), controlling a temperature distribution in the sample by modulating the wavelength of the laser radiation.

3. The process according to claim 1, wherein the beam is applied to the at least one portion while modulating at least one of a scanning speed or a power of the laser radiation.

4. The process according to claim 1,
   wherein the beam has a first cross-sectional width of a first area of the biological structure in which at least 50% of power of the laser radiation is contained,
   wherein, when the beam is applied to the biological structure along a predetermined path in the at least one portion, the beam of the laser radiation applied to a second area of the biological structure which has a second width and includes the predetermined path, wherein the second area is different from the first area, and
   wherein the first and second widths are the same and are measured transverse to a translation direction of the beam.

5. The process according to claim 4, wherein the predetermined path is at least one of (i) helical, (ii) circular, or (iii) includes a set of parallel lines.

6. The process according to claim 1, wherein the beam has a shape such that an integration of a power of the laser radiation in a direction that is parallel to a scanning direction of the laser radiation is constant.

7. The process according to claim 1, further comprising shaping the beam using at least one aperture.

8. The process according to claim 1, further comprising modifying a shape of the beam to be non-circular.

9. The process according to claim 1, wherein the biological structure has a tubular shape.

10. The process according to claim 1, further comprising identifying at least one deformation in the at least one portion using the speckle information as a function of depth within the at least one portion.

11. A process for applying a laser radiation to at least one portion of a biological structure, comprising:
a) providing a beam of the laser radiation to the at least one portion, wherein a cross-sectional area of the beam is at most about 1/10th of an entire area of the at least one portion;
b) applying the beam to the at least one portion (i) while modulating a wavelength of the laser radiation and (ii) while monitoring a depth of the application of the laser radiation;
c) with the beam, causing a temperature change in a section of the biological structure which is near or in the at least one portion of the biological structure;
d) determining a phase-shift of at least one return radiation provided from the section;
e) identifying a deformation of the section at a plurality of depths as a function of the phase-shift of the at least one return radiation provided from the section;
f) determining a laser damage depth within the biological structure based on the deformation of the section at the plurality of depths; and
g) adjusting a penetration depth of the beam by changing the wavelength of the laser radiation.

12. A system for applying a laser radiation to at least one portion of a biological structure, comprising:
an optical configuration comprising an optical fiber configured to provide a beam of the laser radiation to the at least one portion, wherein a cross-sectional area of the beam is at most about 1/10th of an entire area of the at least one portion;
a beam configuration configured to apply the beam to the at least one portion (i) while modulating a wavelength of the laser radiation, and (ii) while monitoring a depth of the application of the laser radiation;
the optical configuration further configured to receive at least one return radiation from the at least one portion; and
a processor configured to:
determine a phase-shift of the at least one return radiation,
identify a deformation within the at least one portion at a plurality of depths as a function of the phase-shift of the at least one return radiation,
determine a laser damage depth within the biological structure based on the deformation within the at least one portion at the plurality of depths, and
adjust a penetration depth of the beam by changing the wavelength of the laser radiation.

13. The system according to claim 12, wherein the laser radiation is provided to the at least one portion of the sample at the wavelength; and
the optical configuration being further configured to modulate the wavelength of the laser radiation when the beam is provided to the at least one portion to control a temperature distribution in the biological structure.

14. The system according to claim 12, wherein the beam is applied to the at least one portion while modulating at least one of a scanning speed or a power of the laser radiation.

15. The system according to claim 12,
wherein the beam has a first cross-sectional width of a first area of the biological structure in which at least 50% of power of the laser radiation is contained,
wherein, when the beam is applied to the biological structure along a predetermined path in the at least one portion, the beam of the laser radiation applied to a second area of the biological structure which has a second width and includes the predetermined path, wherein the second area is different from the first area, and
wherein the first and second widths are the same and are measured transverse to a translation direction of the beam.

16. The system according to claim 15, wherein the predetermined path is at least one of (i) helical, (ii) circular, or (iii) includes a set of parallel lines.

17. The system according to claim 12, wherein the beam has a shape such that an integration of a power of the laser radiation in a direction that is parallel to a scanning direction of the laser radiation is constant.

18. The system according to claim 12, further comprising an aperture to shape the beam.

19. The system according to claim 18, wherein the aperture shapes the beam to be noncircular.

20. The system according to claim 12, wherein the biological structure has a tubular shape.

21. A system for applying a laser radiation to at least one portion of a biological structure, comprising:
an optical configuration comprising an optical fiber configured to provide a beam of the laser radiation to the at least one portion, wherein a cross-sectional area of the beam is at most about 1/10th of an entire area of the at least one portion;
a beam configuration configured to apply the beam to the at least one portion (i) while modulating a wavelength of the laser radiation, and (ii) while monitoring a depth of the application of the laser radiation,
applying the beam causing a temperature change in a section of the sample which is near or in the at least one portion of the biological structure; and
a processor configured to:
determine a phase-shift of at least one return radiation provided from the section,
identify a deformation of the section at a plurality of depths as a function of the phase-shift of the at least one return radiation provided from the section,
determine a laser damage depth within the biological structure based on the deformation of the section at the plurality of depths, and
adjust a penetration depth of the beam by changing the wavelength of the laser radiation.

* * * * *

UNITED STATES PATENT AND TRADEMARK OFFICE
CERTIFICATE OF CORRECTION

PATENT NO. : 10,426,548 B2  
APPLICATION NO. : 11/670043  
DATED : October 1, 2019  
INVENTOR(S) : Guillermo J. Tearney et al.

Page 1 of 1

It is certified that error appears in the above-identified patent and that said Letters Patent is hereby corrected as shown below:

In the Specification

Column 21, Lines 45-47, "frequencies, e.g., using a computer 3095 which is part of an exemplary imaging system shown in FIGS. 15-20 and" should be --frequencies and--.

Column 22, Line 39, "Cheman" should be --Cherian--.

Column 22, Line 62, "Teamey" should be --Tearney--.

Column 23, Line 1, "Teamey" should be --Tearney--.

Column 23, Line 5, "Teamey" should be --Tearney--.

Column 23, Line 9, "Teamey" should be --Tearney--.

Signed and Sealed this  
Twelfth Day of November, 2019

Andrei Iancu  
*Director of the United States Patent and Trademark Office*